United States Patent
Sordella et al.

(10) Patent No.: US 10,501,741 B2
(45) Date of Patent: Dec. 10, 2019

(54) METHODS AND COMPOSITIONS FOR INHIBITING GROWTH AND EPITHELIAL TO MESENCHYMAL TRANSITION (EMT) IN CANCER CELLS

(71) Applicants: Cold Spring Harbor Laboratory, Cold Spring Harbor, NY (US); Rutgers, The State University of New Jersey, New Brunswick, NJ (US)

(72) Inventors: Raffaella Sordella, Cold Spring Harbor, NY (US); Serif Senturk, Cold Spring Harbor, NY (US); Luca Cartegni, New York, NY (US); Zhan Yao, New York, NY (US)

(73) Assignees: Cold Spring Harbor Laboratory, Cold Spring Harbor, NY (US); Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 15/321,561

(22) PCT Filed: Jun. 25, 2015

(86) PCT No.: PCT/US2015/037830
§ 371 (c)(1),
(2) Date: Dec. 22, 2016

(87) PCT Pub. No.: WO2015/200725
PCT Pub. Date: Dec. 30, 2015

(65) Prior Publication Data
US 2017/0211072 A1 Jul. 27, 2017

Related U.S. Application Data

(60) Provisional application No. 62/016,894, filed on Jun. 25, 2014.

(51) Int. Cl.
| | | |
|---|---|---|
| A61K 38/13 | (2006.01) |
| C12N 15/113 | (2010.01) |
| A61K 31/445 | (2006.01) |
| G01N 33/574 | (2006.01) |
| A61K 31/198 | (2006.01) |
| A61K 31/713 | (2006.01) |
| A61K 45/06 | (2006.01) |

(52) U.S. Cl.
CPC ........ *C12N 15/1137* (2013.01); *A61K 31/198* (2013.01); *A61K 31/445* (2013.01); *A61K 31/713* (2013.01); *A61K 38/13* (2013.01); *A61K 45/06* (2013.01); *C12Y 502/01008* (2013.01); *G01N 33/574* (2013.01); *G01N 33/57407* (2013.01); *G01N 33/57496* (2013.01); *C12N 2310/11* (2013.01); *C12N 2310/14* (2013.01); *C12N 2310/20* (2017.05); *C12N 2320/30* (2013.01); *C12N 2320/31* (2013.01); *G01N 2333/4748* (2013.01); *G01N 2800/52* (2013.01)

(58) Field of Classification Search
None
See application file for complete search history.

(56) References Cited

FOREIGN PATENT DOCUMENTS

WO    WO 00/22127 A1    4/2000

OTHER PUBLICATIONS

Chambers et al., "Phase I trial of intravenous carboplatin and cyclosporin A in refractory gynecological cancer patients", Clin Cancer Res, 1996, pp. 1699-1704 (Year: 1996).*
Kazakov et al., "Expression of p53 and TP53 Mutational Analysis in Malignant Neoplasms Arising in Preexisting Spiradenoma, Cylindroma, and Spiradenocylindroma, Sporadic or Associated with Brooke—Spiegler Syndrome", Am J Dermatopathol, 2010, pp. 215-221 (Year: 2010).*
Boffa et al., "Rapamycin Inhibits the Growth and Metastatic Progression of Non-Small Cell Lung Cancer", Clinical Cancer Research, 2004, pp. 293-300 (Year: 2004).*
Senturk et al., "p53ψ is a transcriptionally inactive p53 isoform able to reprogram cells toward a metastatic-like state", PNAS, Jul. 2014, pp. E3287-E3296 (Year: 2014).*
International Search Report and Written Opinion for Application No. PCT/US2015/037830 dated Oct. 8, 2015.
International Preliminary Report on Patentability for Application No. PCT/US2015/037830 dated Jan. 5, 2017.
Ghosh et al., Regulation of human p53 activity and cell localization by alternative splicing. Mol Cell Biol. Sep. 2004;24(18):7987-97.
Goldschneider et al., Expression of C-terminal deleted p53 isoforms in neuroblastoma. Nucleic Acids Res. 2006;34(19):5603-12. Epub Oct. 5, 2006.
Roger et al., Gain of oncogenic function of p53 mutants regulates E-cadherin expression uncoupled from cell invasion in colon cancer cells. J Cell Sci. Apr. 15, 2010;123(Pt 8):1295-305. doi: 10.1242/jcs.061002. Epub Mar. 23, 2010.
Senturk et al., p53Ψ is a transcriptionally inactive p53 isoform able to reprogram cells toward a metastatic-like state. Proc Natl Acad Sci U S A. Aug. 12, 2014;111(32):E3287-96. doi: 10.1073/pnas.1321640111. Epub Jul. 29, 2014.
Walsh et al., Cyclosporine a mediates pathogenesis of aggressive cutaneous squamous cell carcinoma by augmenting epithelial-mesenchymal transition: role of TGFβ signaling pathway. Mol Carcinog. Jul. 2011;50(7):516-27. doi: 10.1002/mc.20744. Epub Feb. 9, 2011.
Supplementary European Search Report for Application No. EP 15812701.9, dated Nov. 14, 2017.
Huang et al. Mutations in exon 7 and 8 of p53 as poor prognostic factors in patients with non-small cell lung cancer. Oncogene 16 (19), Jan. 1998, 2469-2477.
Lehman et al. Elevated Frequency and Functional Activity of a Specific Germ-Line p53 Intron Mutation in Familial Breast Cancer 1. Cancer Research 60 (4), Feb. 2000, 1062-1069.
Sakurai et al. Novel p53 splicing site mutation in Li-Fraumeni-like syndrome with osteosarcoma: Novel p53 splicing site mutation in LFL. Pediatrics International 55 (1), Feb. 2013, 107-111.
Weghorst et al. Cloning and sequence of a processed p53 pseudogene from rat: a potential source of false 'mutations' in PCR fragments of tumor DNA. Gene 166 (2) Jan. 1995, 317-322.

* cited by examiner

Primary Examiner — Lianko G Garyu
(74) Attorney, Agent, or Firm — Wolf, Greenfield & Sacks, P.C.

(57) ABSTRACT

Provided herein are methods and compositions for inhibiting epithelial to mesenchymal transition of a cell.

25 Claims, 49 Drawing Sheets
Specification includes a Sequence Listing.

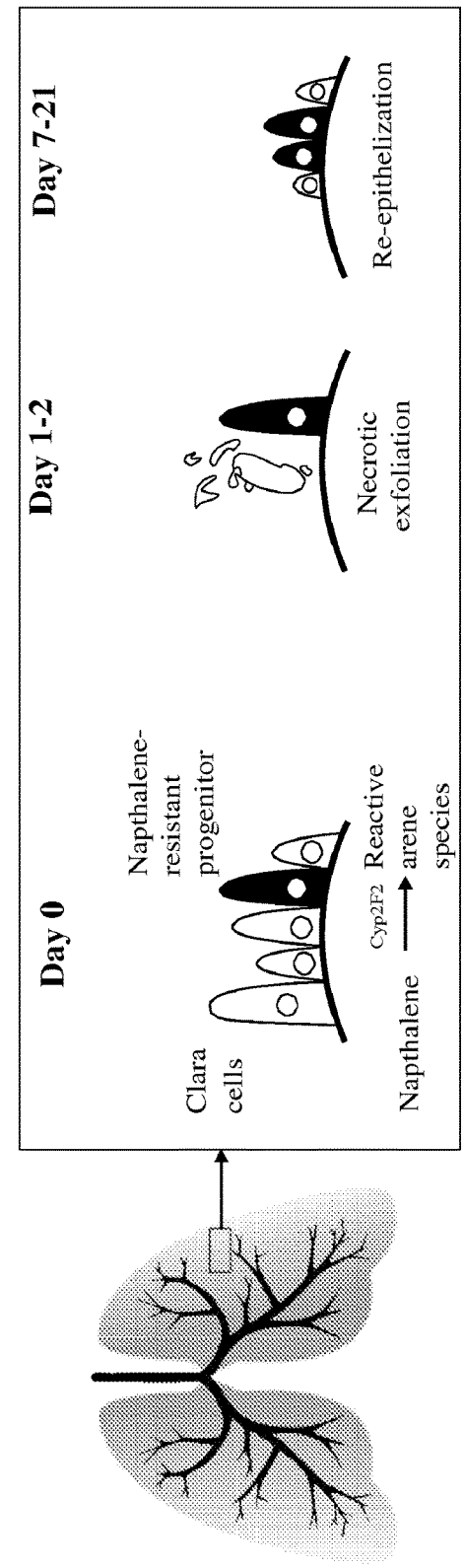

Fold change

| GENE | GENE SYMBOL | CD44L vs CD44H |
|---|---|---|
| Cell surface glycoprotein CD44 | CD44 | -2.7 |
| Cycline-dependent kinase inhibitor 1A (p21, Cip1) | CDKN1A | 2.5 |
| TP53-regulated inhibitor of apoptosis 1 | Triap1 | 6.4 |
| Sestrin 1 | Sesn1 | 8.9 |
| Sestrin 2 | Sesn2 | 2.0 |
| Phosphoglycerate mutase 1 | Pgam1 | 9.4 |
| Phosphoglycerate mutase 2 | Pgam2 | 9.1 |
| SCO cytochrome oxidase deficient 1 | Sco1 | 1.3 |
| SCO cytochrome oxidase deficient 2 | Sco2 | 6.2 |
| p53 E3 ubiquitin-protein ligase | Mdm2 | 6.4 |
| TP53-induced glycolysis and apoptosis regulator, C12orf5 | Tigar | 2.2 |
| Glutathione perioxidase 1 | Gpx1 | 19.3 |

Figure 2 (continued)
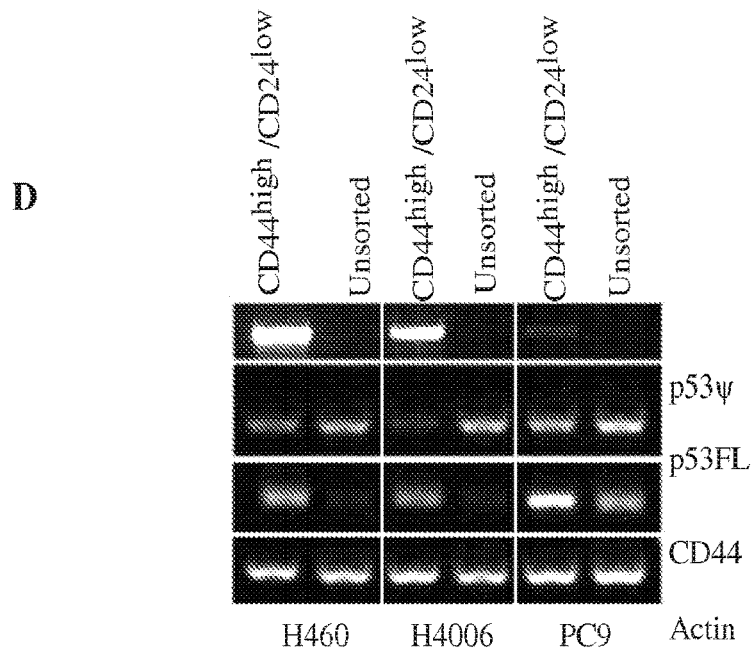
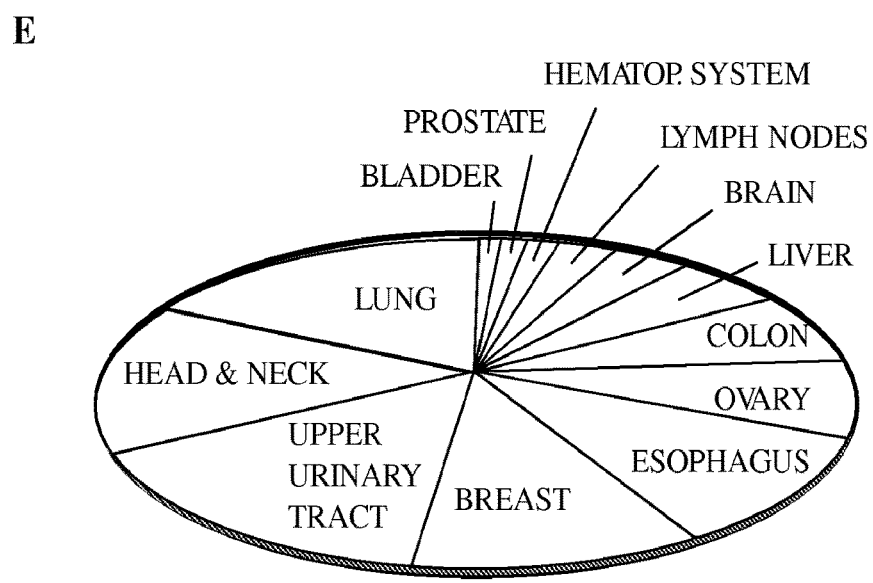

Figure 2 (continued)
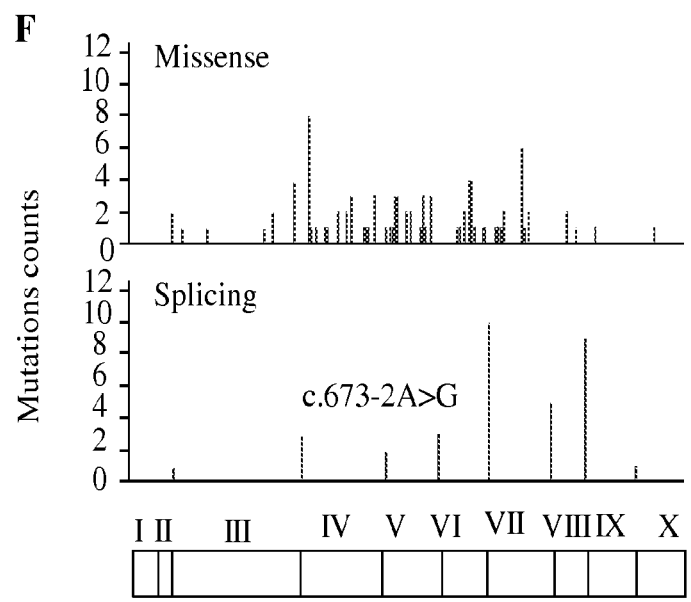
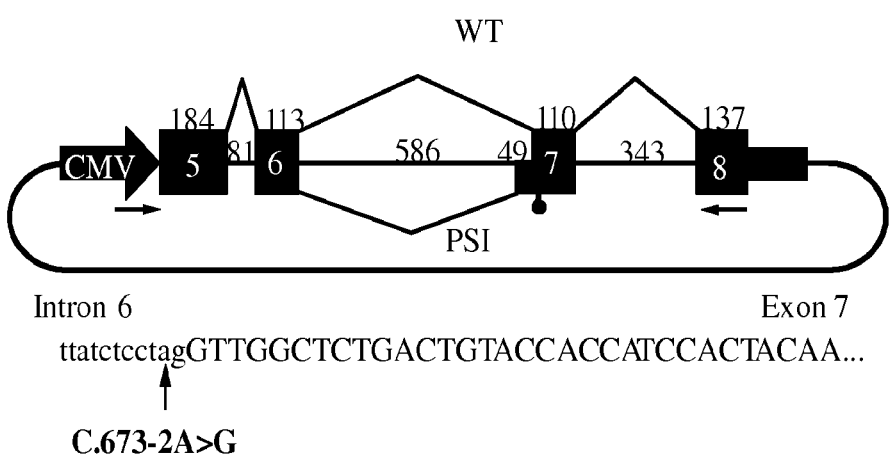

Figure 2 (continued)
H
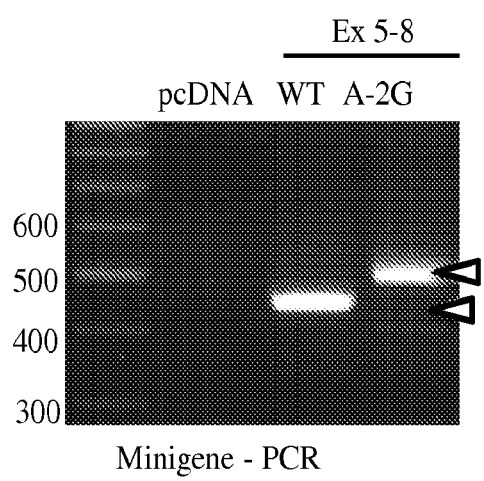
Minigene - PCR
I
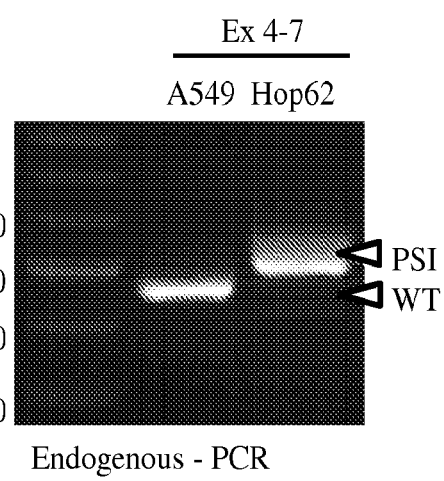
Endogenous - PCR
L
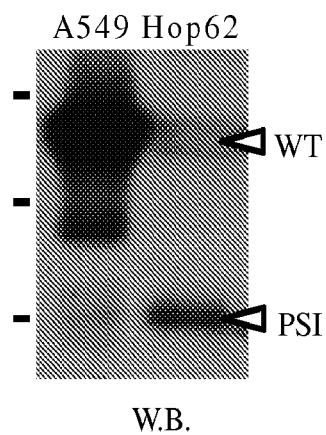
W.B.

Figure 3
A
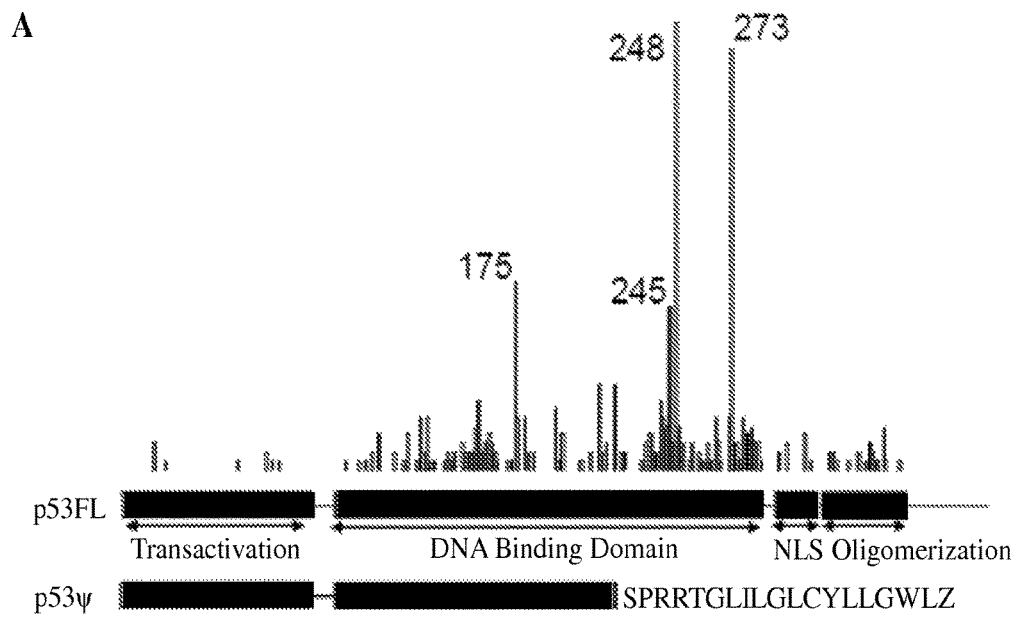
B
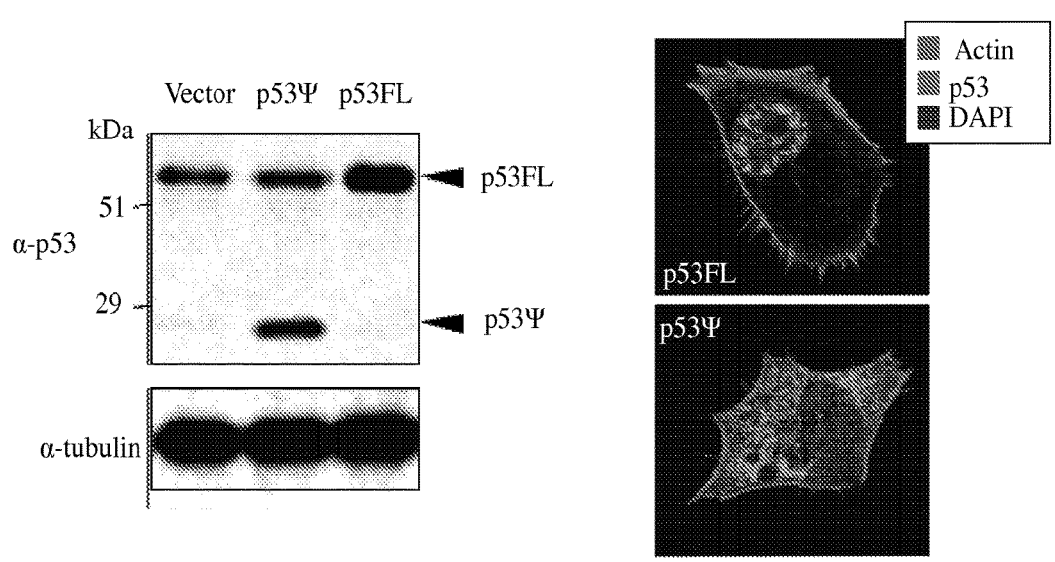

Figure 4 (continued)
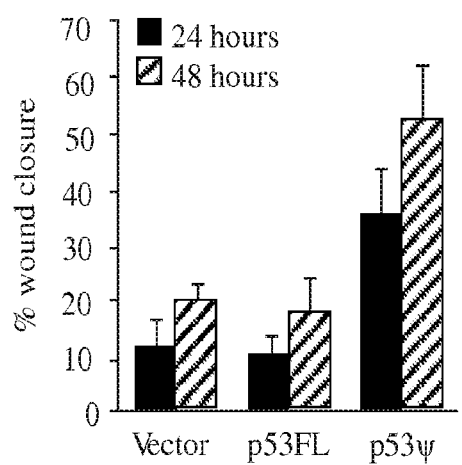
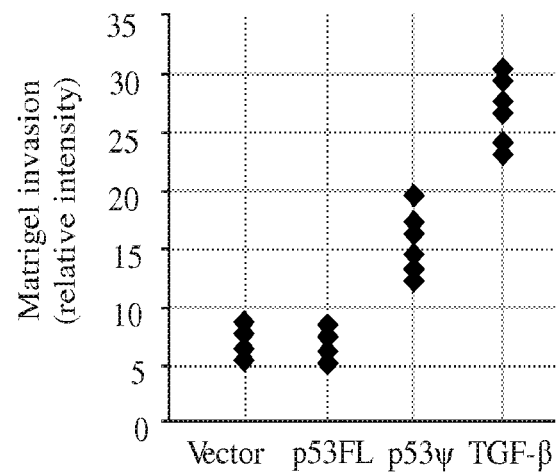

Figure 5
A
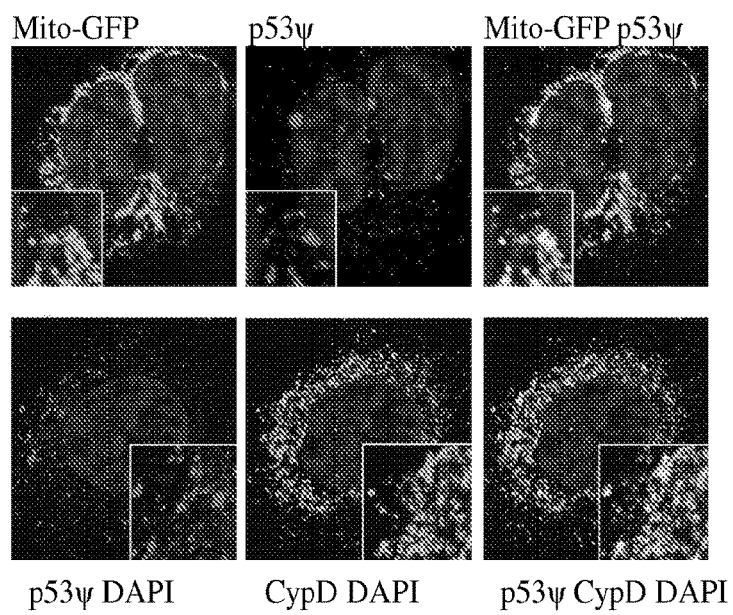
B
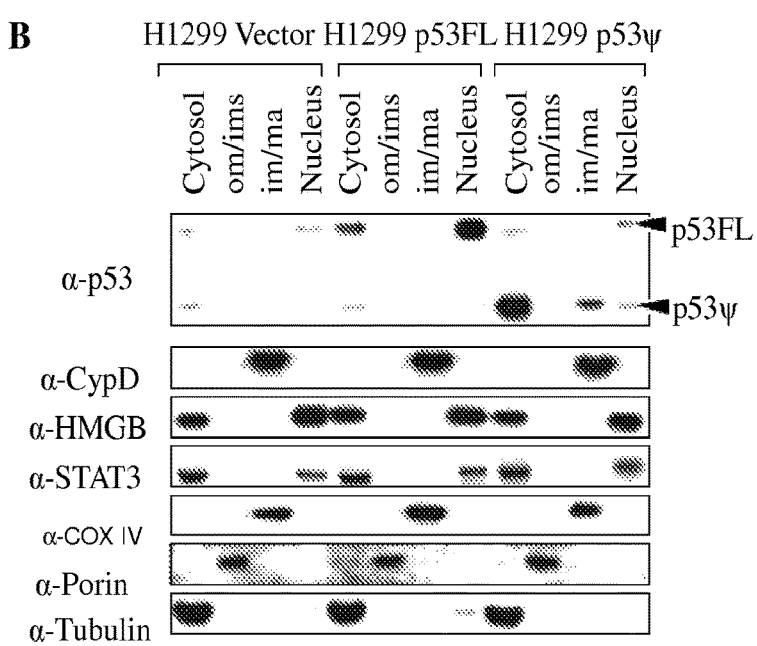

Figure 6
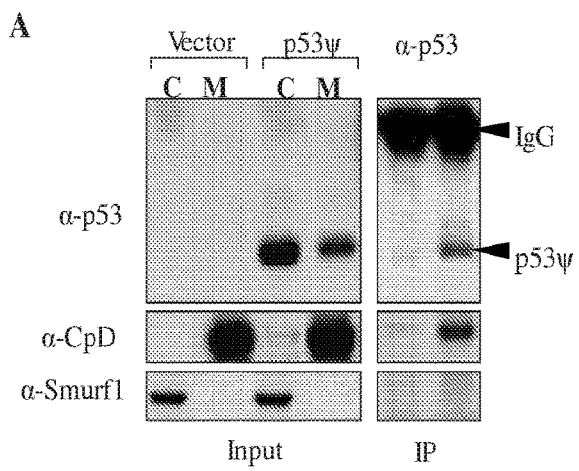
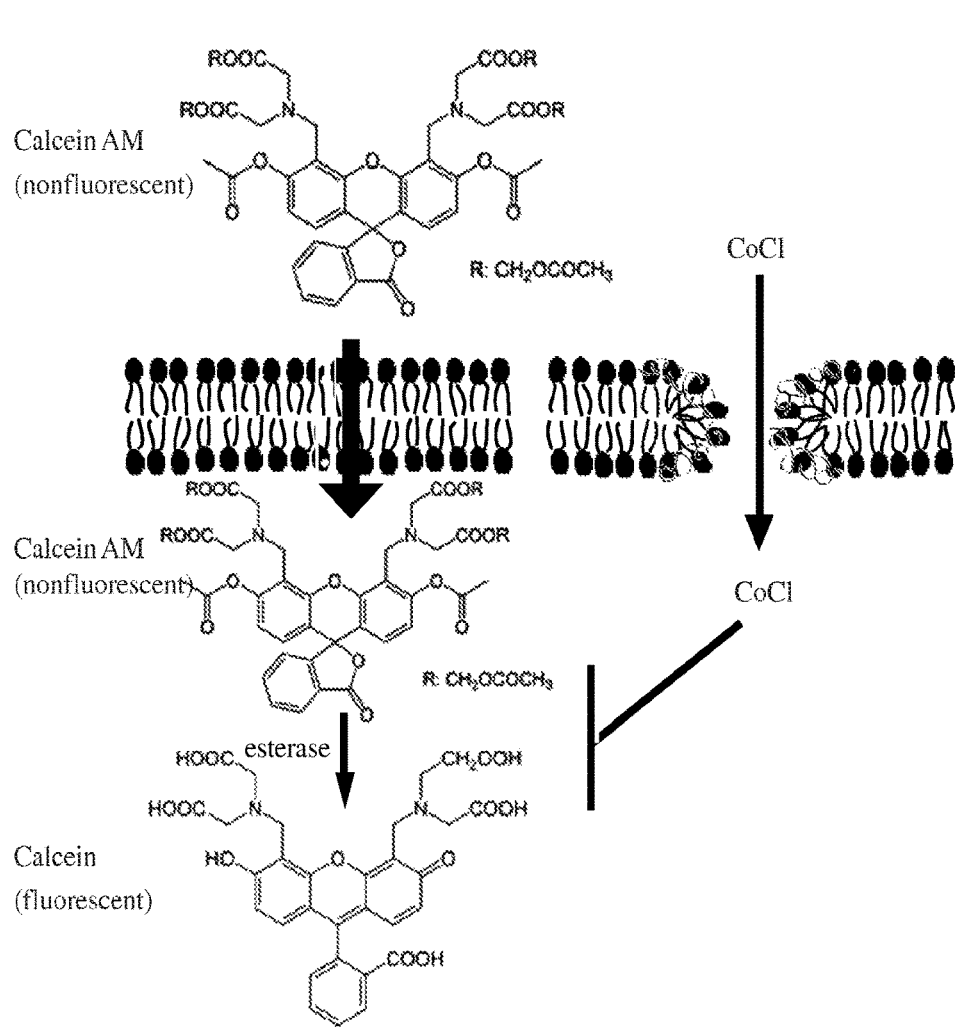

Figure 6 (continued)
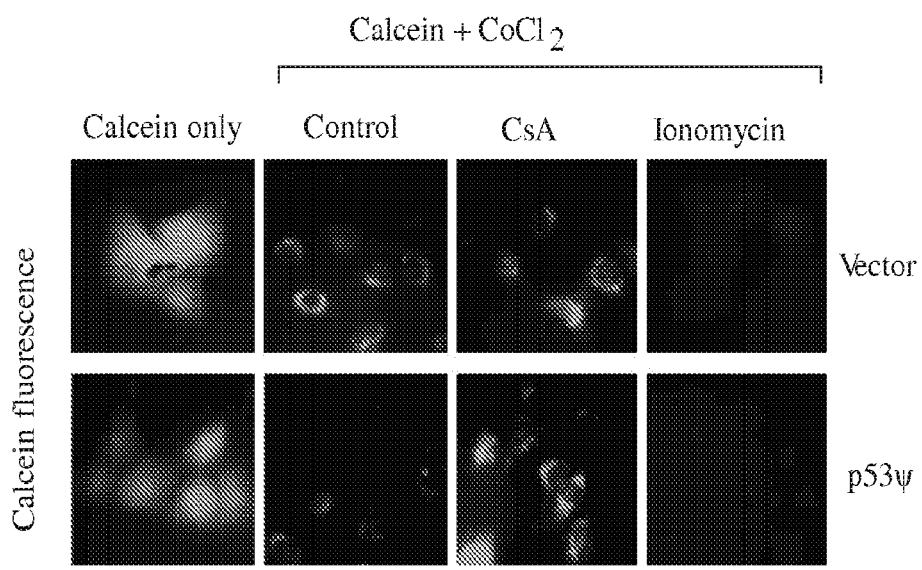
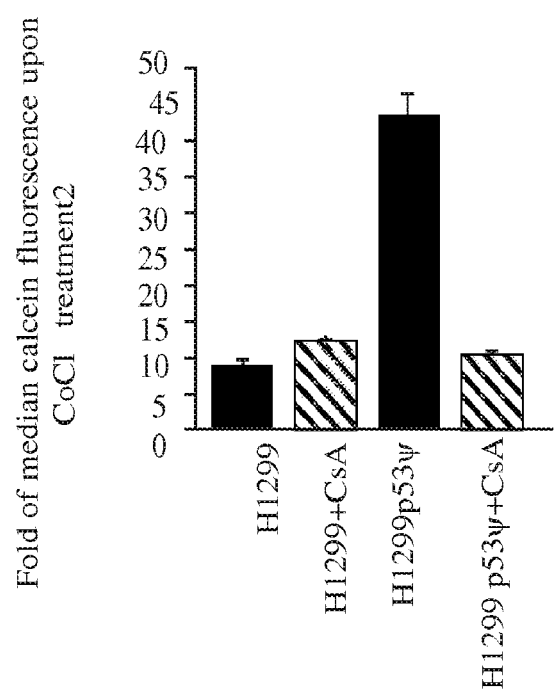

Figure 6 (continued)
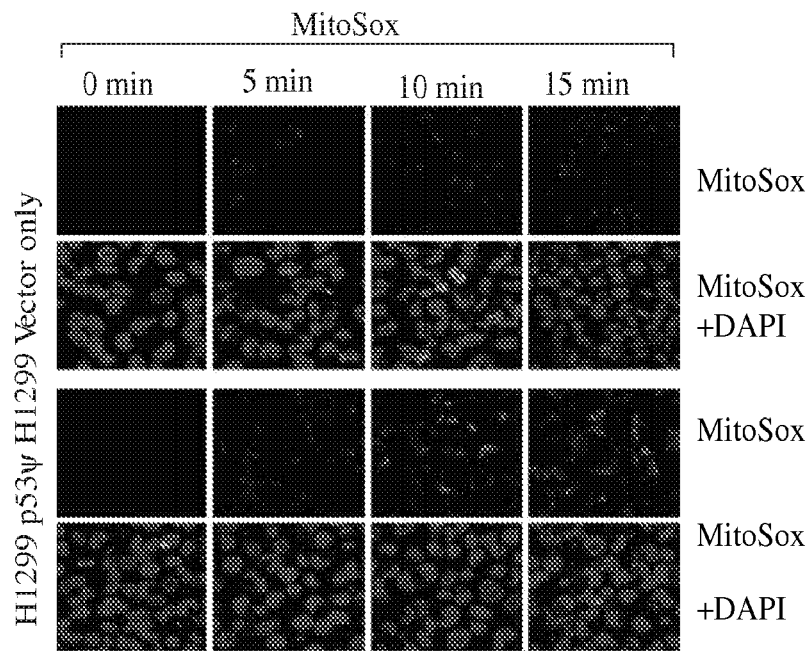
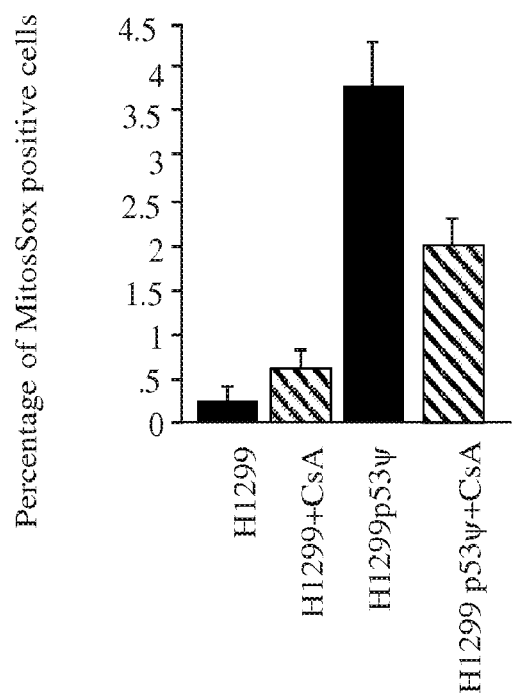

Figure 7
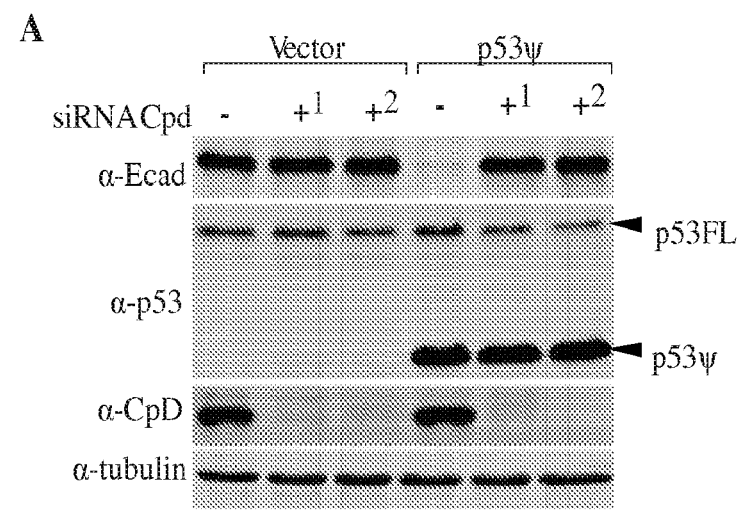
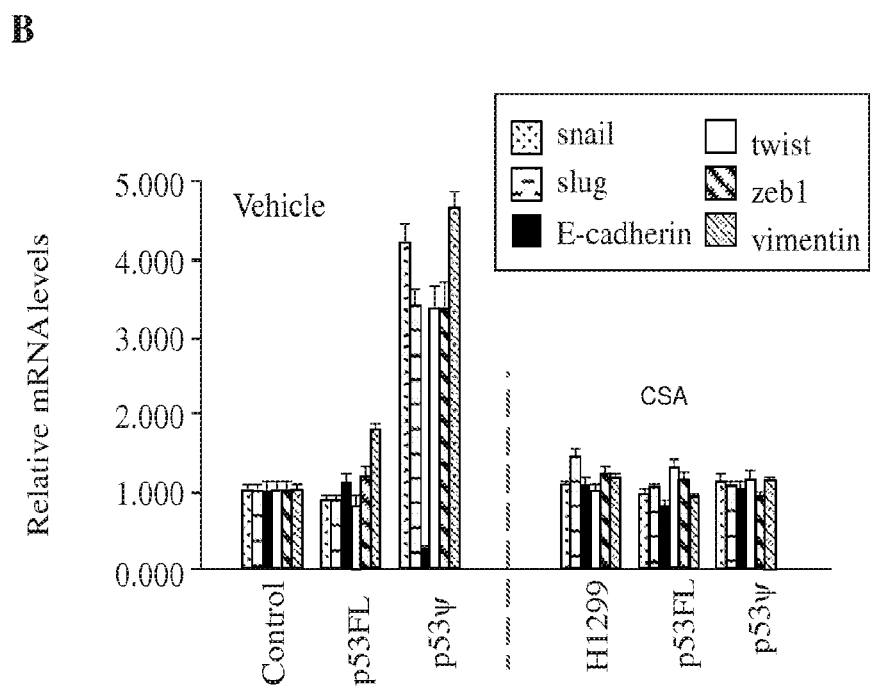

Figure 8

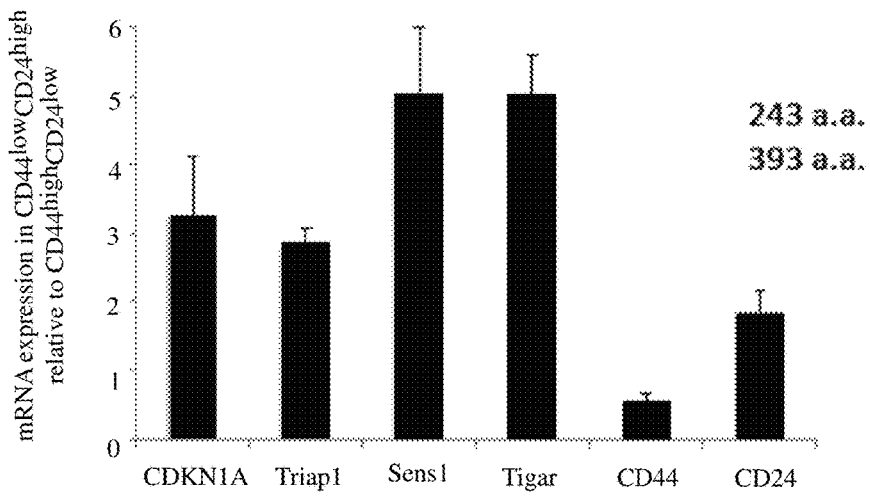

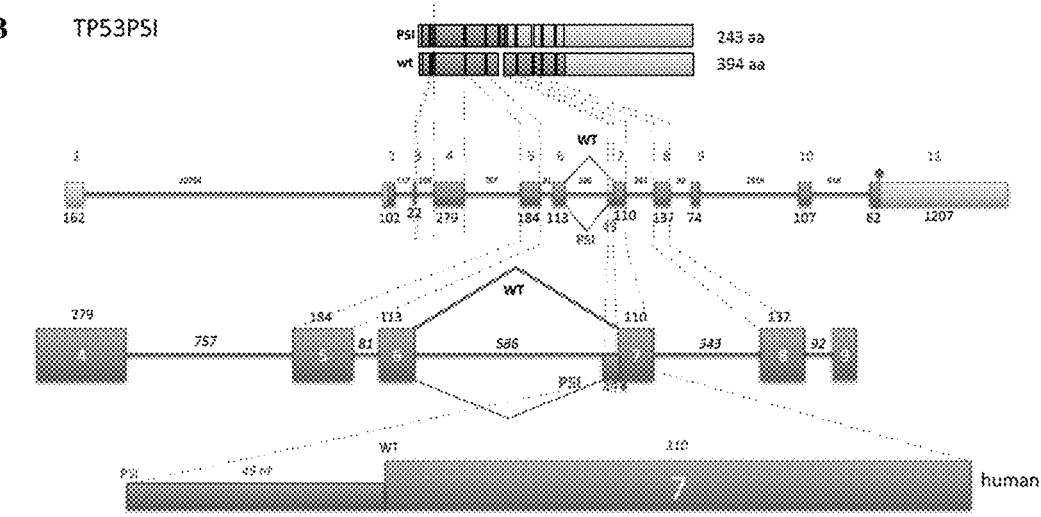

ggcctcccctgcttgccacaggtctctcccaaggcgcactggcctcatcttgggcctgtgttatctcctagGTTGGCTCTGACTGT
ACCACCATCCACTACAACTACATGTGTAACAGTTCCTGCATGGGCGGCATGAACCGGA
GGCCCATCCTCACCATCATCACACTGGAAGACTCCAGgtcaggagcc tcccggctgctgcaggtcacctgtagtgaggtagggagcgacttcacctggatcctgtgtcttcccccagGCCGGCTCTGAGTA
TACCACCATCCACTACAAGTACATGTGTAATAGCTCCTGCATGGGGGGCATGAACCGC
CGACCTATCCTTACCATCATCACACTGGAAGACTCCAGgtaggaaggc

Figure 8 (continued)
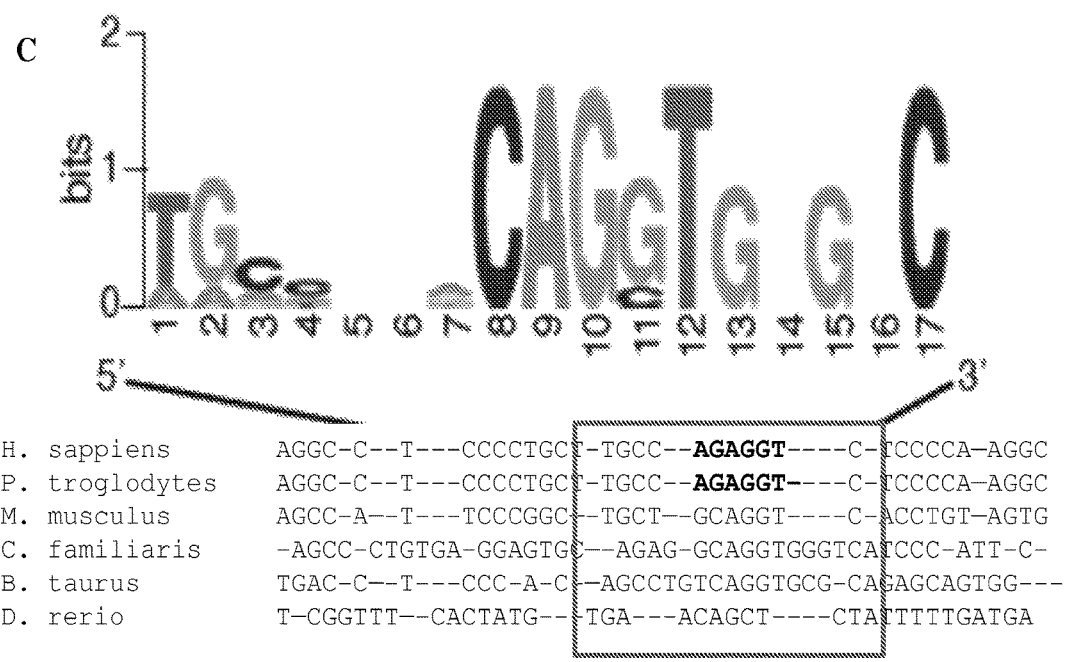

Figure 8 (continued)
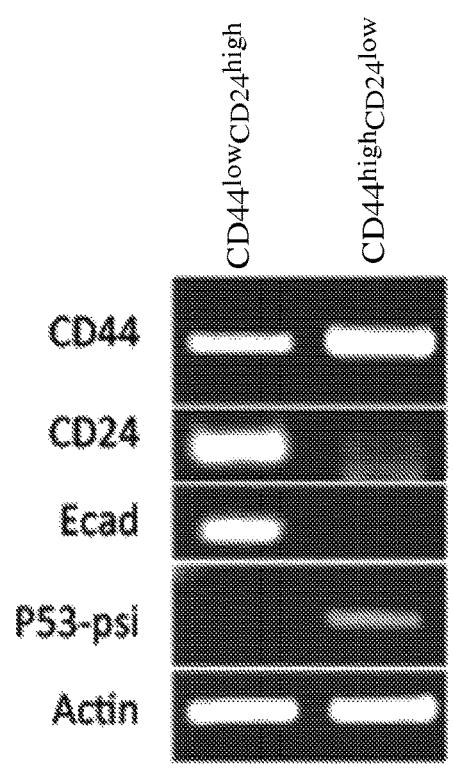
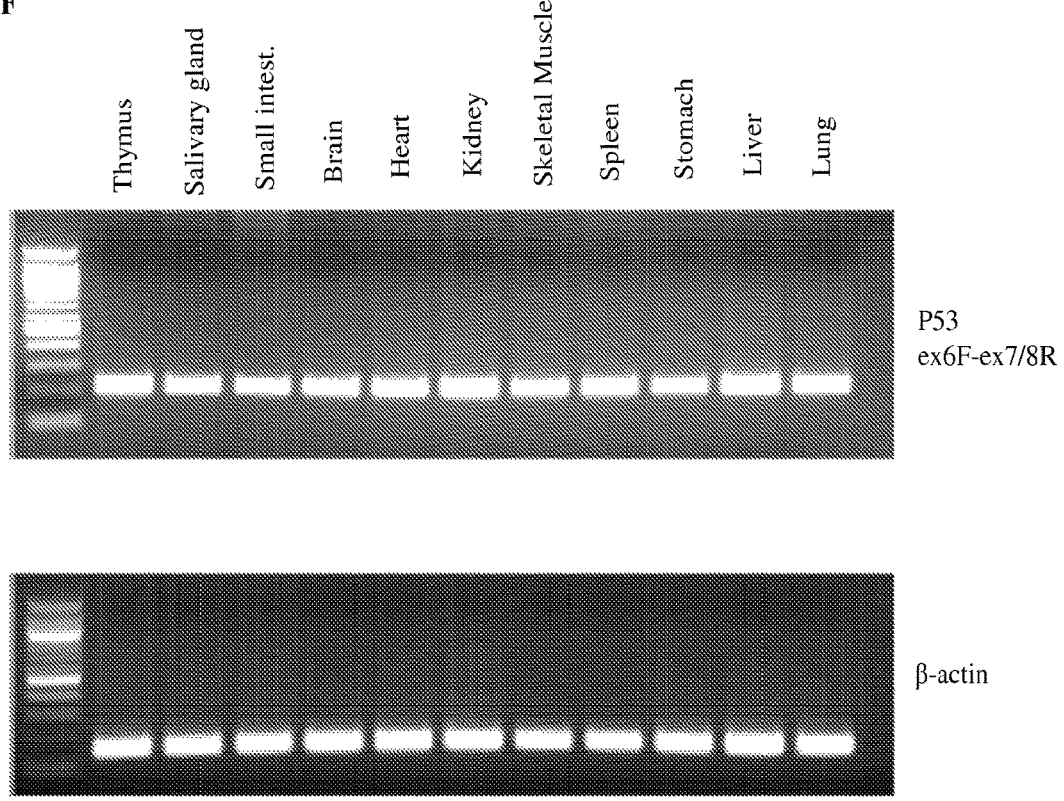

A

B  Patient demographics

| Variable | | Number (%) |
|---|---|---|
| Median age | | 69 (46-90) |
| Gender | Male | 88 (37%) |
| | Female | 145 (62%) |
| Smoking status | Current/former | 169 (72%) |
| | Never | 28 (12%) |
| | Unknown | 36 (15%) |
| Histology | Adenocarcinoma | 223 (96%) |
| | Adeno-Squamous | 10 (4%) |
| Stage | IA | 122 (52%) |
| | IB | 59 (25%) |
| | IIA | 5 (2%) |
| | IIB | 25 (11%) |
| | IIIA | 23 (10%) |
| | unknown | 22 (11%) |
| Outcome | Alive: no recurrence | 160 (68%) |
| | Alive: recurrence | 22 (9%) |
| | Dead: documented recurrence | 35 (15%) |
| | Dead: no documented recurrence | 16 (7%) |

C     P53 (DO1)     P53-ψ

D

CD44 and CD24 staining frequency

| Phenotype | Number of patients | Percent of cohort |
|---|---|---|
| CD44+/CD24- | 39 | 17% |
| All others | 194 | 83% |

E    p53ψ CD44+/CD24- frequency

| Phenotype | Number of patients p53ψ positive | Number of patients p53ψ negative | p53ψ positive Percent of cohort |
|---|---|---|---|
| Total | 52 | 181 | 22.3 % |
| CD44+/CD24- | 29 | 10 | 74% |
| All others | 23 | 171 | 11% |

Figure 9 (continued)

F  p53Ψ stage frequency

| Phenotype | Number of patients p53Ψ positive | Number of patients p53Ψ negative | p53Ψ positive percent of cohort |
|---|---|---|---|
| IA-IB | 30 | 109 | 13% |
| IIA-IIB | 8 | 13 | 3% |
| IIIA-IIIB | 9 | 30 | 4% |
| IV | 2 | 10 | 0.08% |
| Unknown | 3 | 19 | 0.01% |

G  p53Ψ status as predictor of survival

| Phenotype | Mean disease free survival time | Standard deviation | Lower bound (95%) | Upper bound (95%) |
|---|---|---|---|---|
| P53-psi positive | 903.291 | 75.851 | 754 | 1051.9 |
| P53-psi negative | 2437.845 | 119.235 | 2204.150 | 2671.5 |

Figure 9 (continued)

| Variable | | Number (%) |
|---|---|---|
| Total number | | 172 |
| Geographic origin | Croatia (Danube River) | 22 (13%) |
| | Southern Europe | 23 (14%) |
| | Chinese Taipei | 127 (73%) |
| Mutations | Missense | 99 (57%) |
| | Non sense | 28 (16%) |
| | Intronic | 20 (15%) |

N

Figure 10
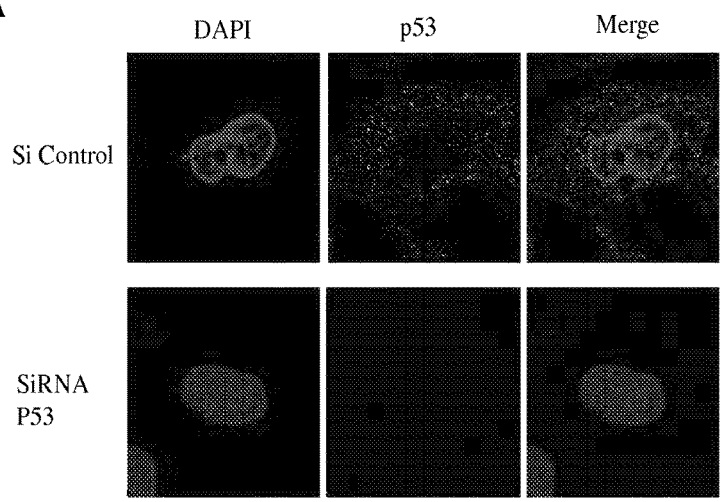
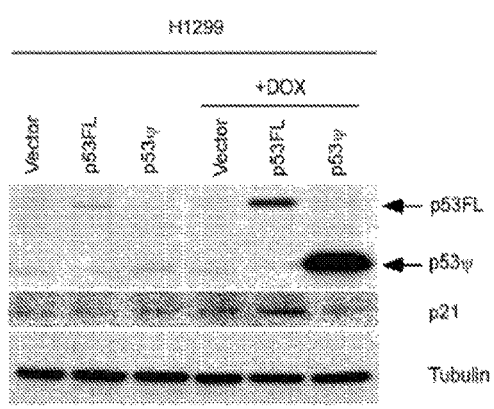
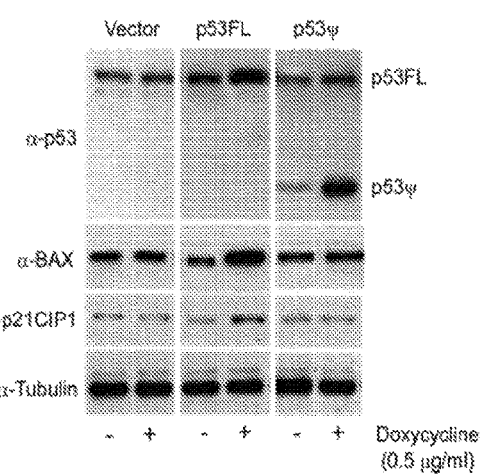

Figure 13
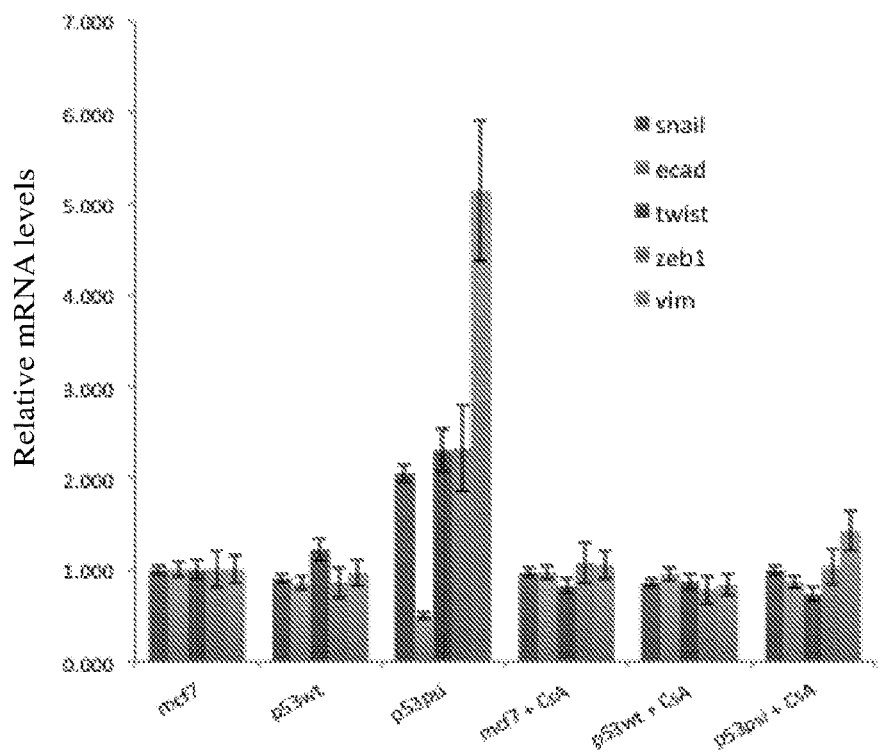
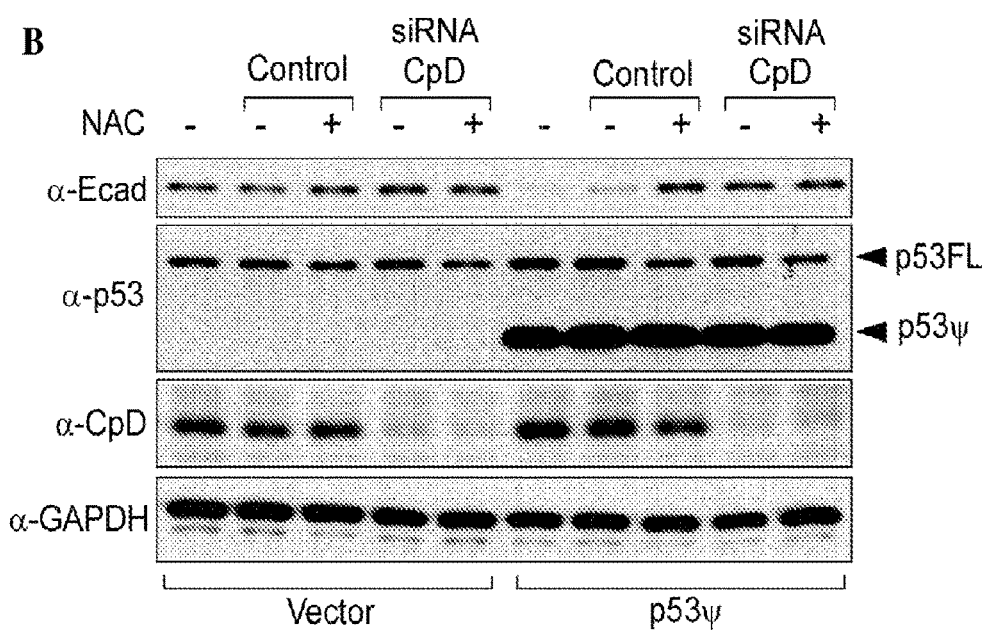

Figure 13 (continued)
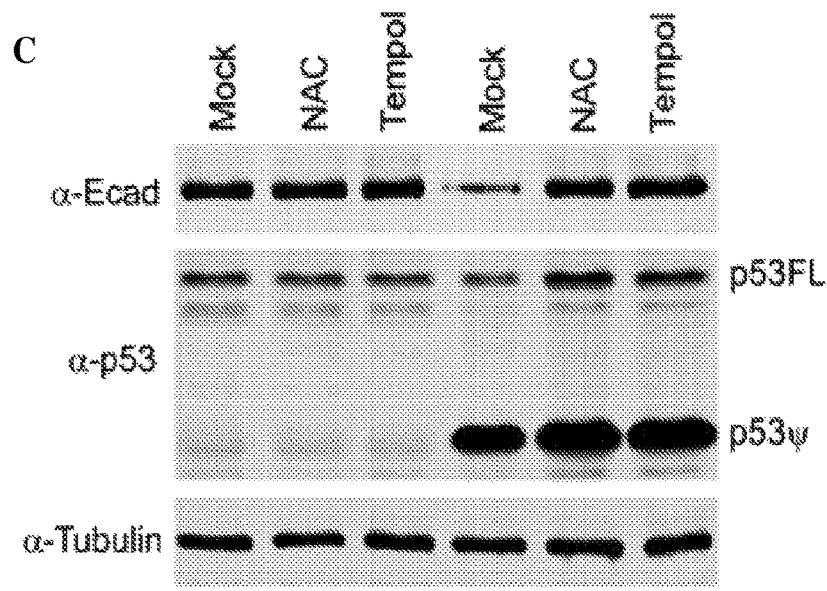
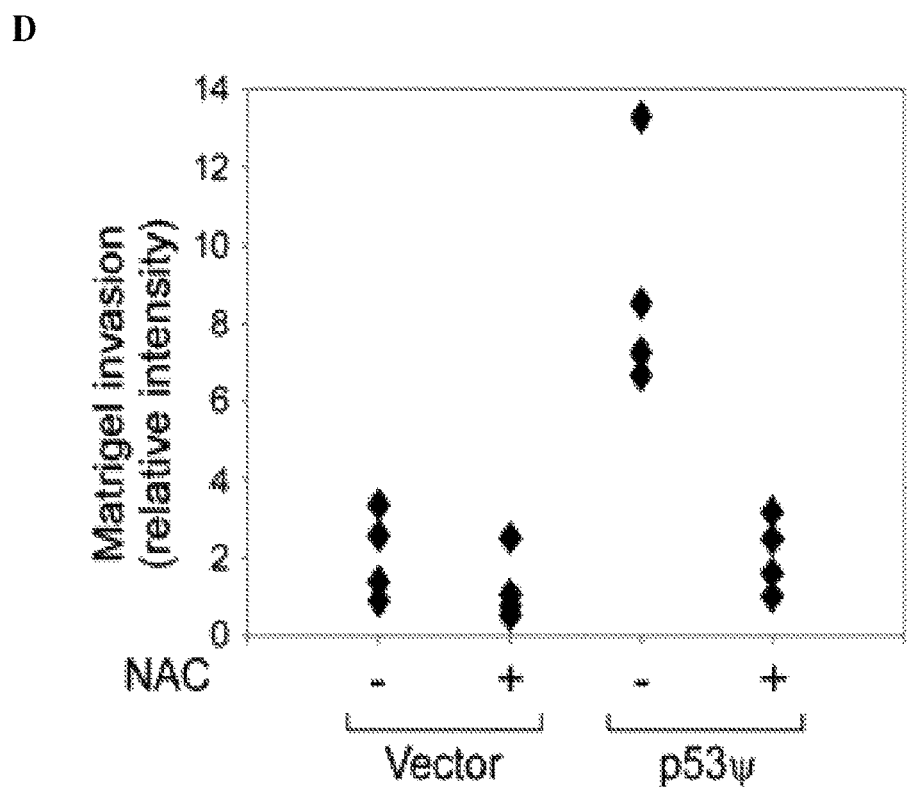

Figure 16
A.
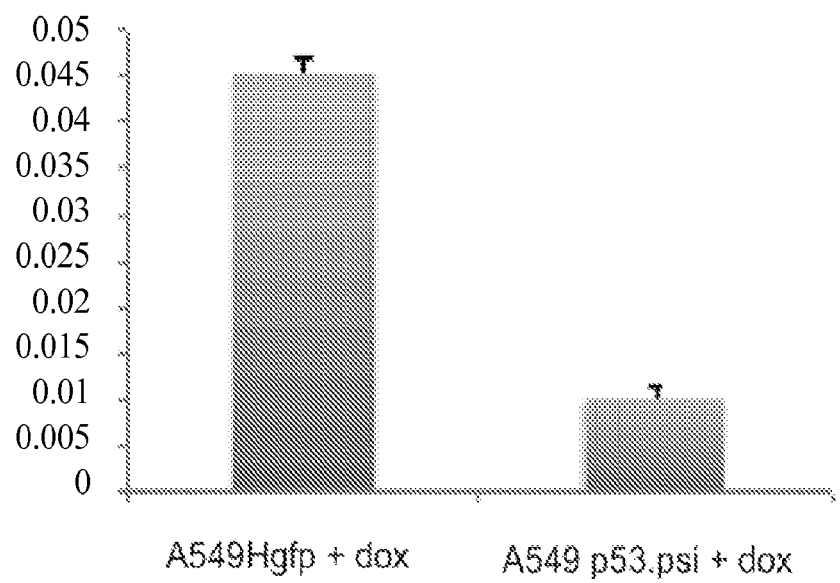
B.
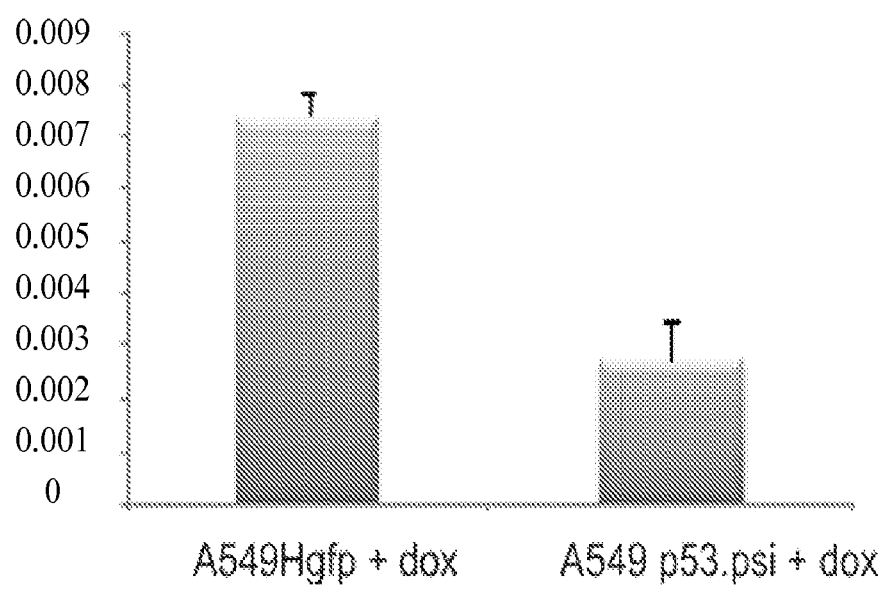

Figure 16 (continued)
C.
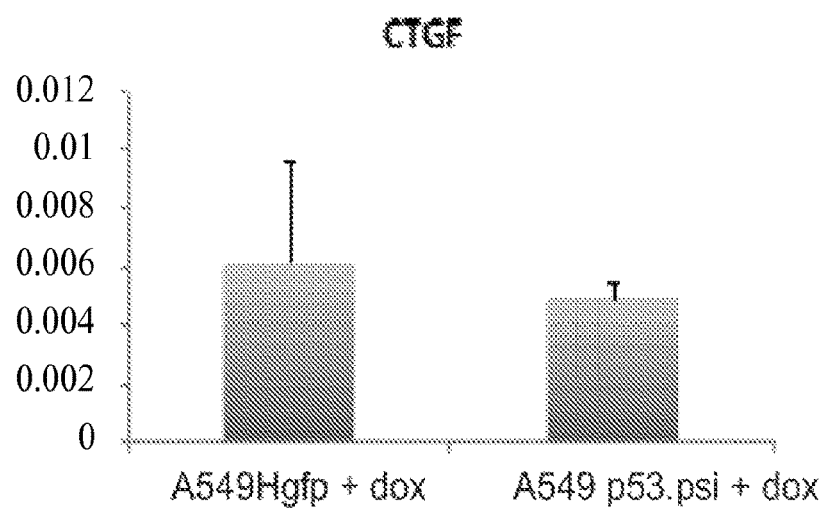
D.
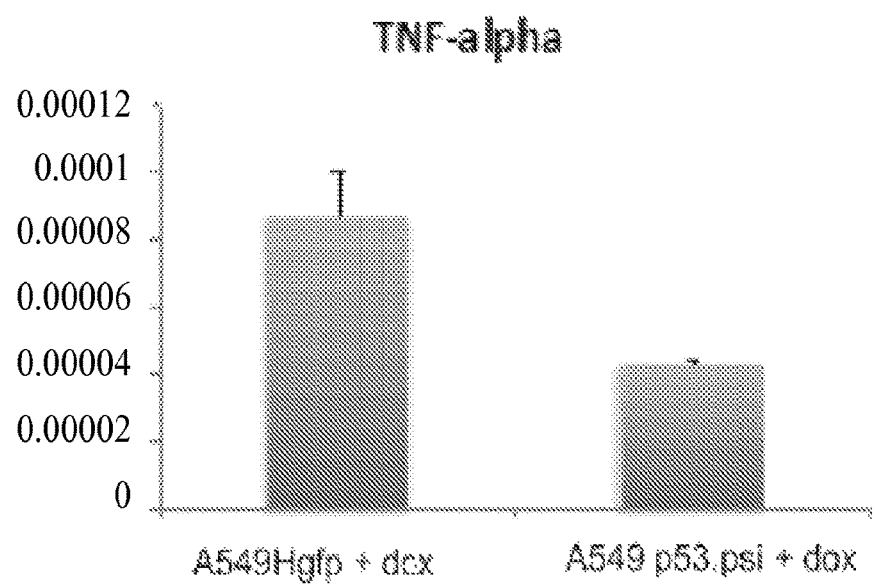

Figure 16 (continued)
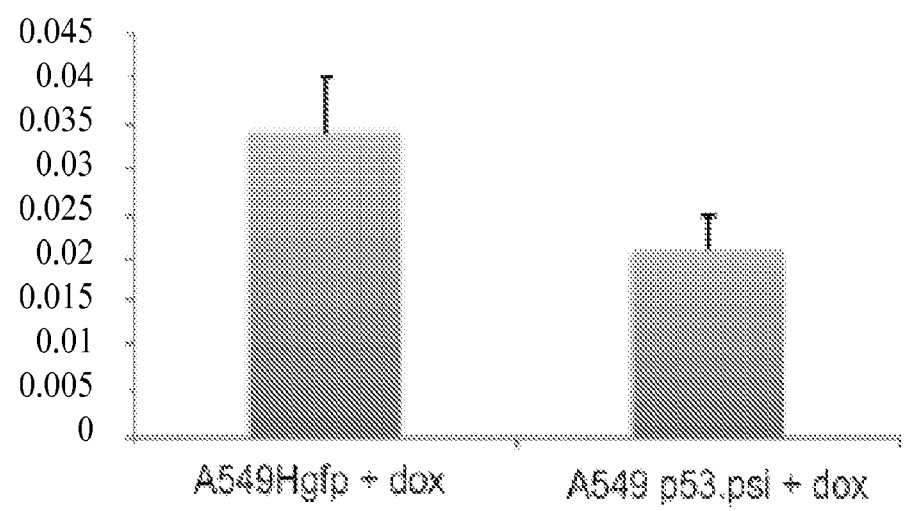
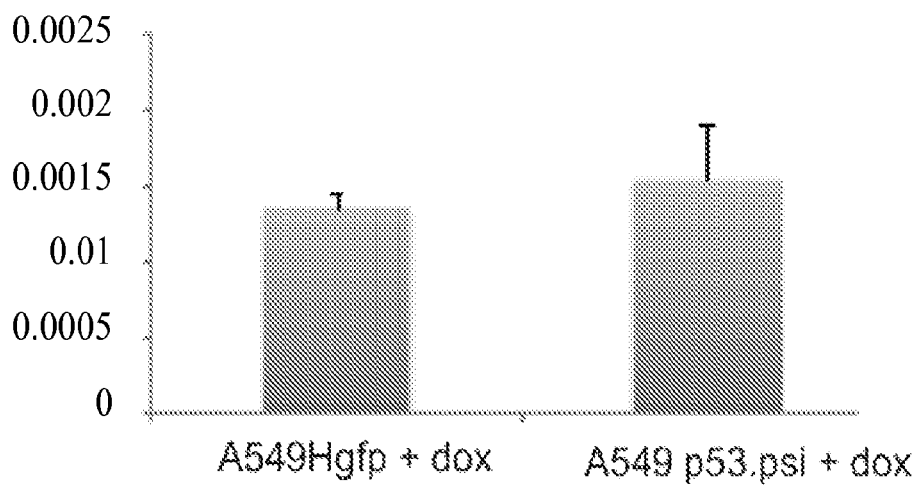

Figure 16 (continued)
G.
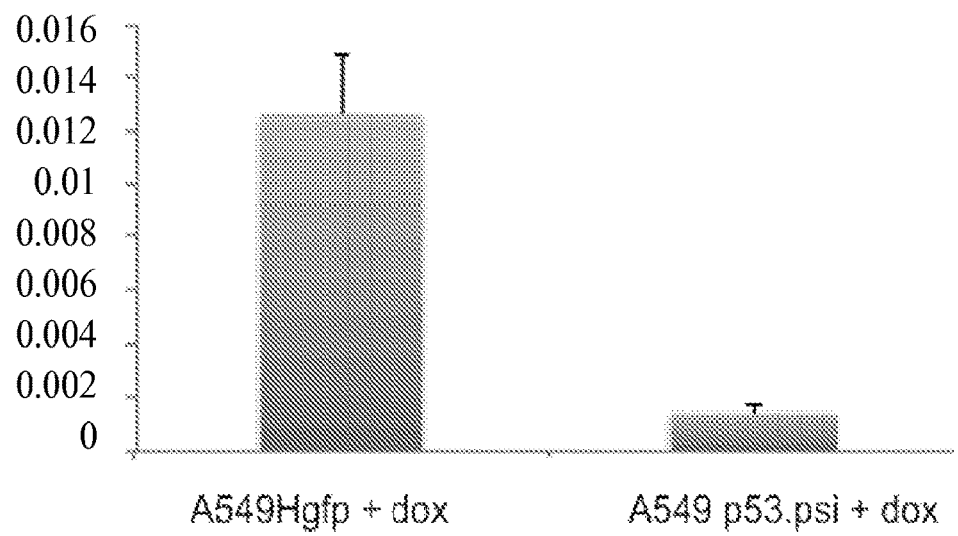
H.
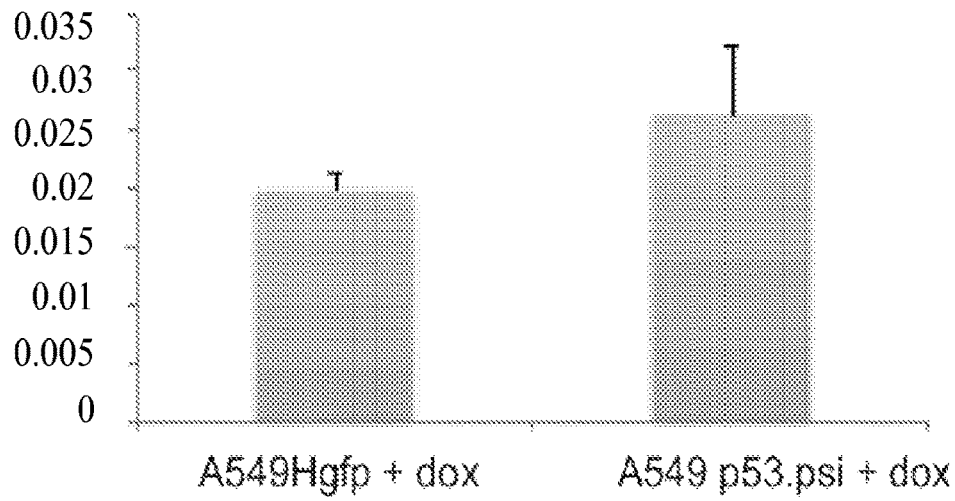

METHODS AND COMPOSITIONS FOR INHIBITING GROWTH AND EPITHELIAL TO MESENCHYMAL TRANSITION (EMT) IN CANCER CELLS

RELATED APPLICATIONS

This application is a national stage filing under 35 U.S.C. § 371 of international application number PCT/US2015/037830, filed Jun. 25, 2015, which was published under PCT Article 21(2) in English and claims the benefit under 35 U.S.C. § 119(e) of U.S. provisional application Ser. No. 62/016,894, filed Jun. 25, 2014. The entire teachings of each of International Application PCT/US2015/037830 and U.S. provisional application Ser. No. 62/016,894 are incorporated herein by reference in their entirety.

BACKGROUND

P53 is an evolutionarily conserved transcription factor with origins that can be traced back to the early metazoans, approximately 700 million years ago [1]. This transcription factor plays a critical role in regulating many fundamental aspects of reversible and irreversible cellular stress responses, genome surveillance, and suppression of oncogenic transformation [1]. In response to strong cellular stresses such as DNA damage or oncogenic signals, p53 regulates the expression of a large cohort of genes that affect cell-cycle arrest, senescence, and apoptosis [1]. Recent work has uncovered additional roles for p53 under basal physiological conditions. These include regulation of development, reproduction, metabolism, and self-renewal capacity [2], [3], [4], [5]. The factors that influence the diversity and duration of p53 responses are not well understood.

SUMMARY

Described is a method of inhibiting (partially or completely) epithelial to mesenchymal transition (EMT) of a cell that expresses an alternative splicing isoform of the TP53 gene or harbors a mutation in a p53-encoding gene in the TP53 gene, at position c.673−2A (e.g., c.673−2A>T) or at a position corresponding to c.673−2A, as designated with reference to the TP53 gene. The p53 variant, whether a result of alternative splicing or of mutation of the TP53 gene, is referred to as p53Ψ. The term p53Ψ or p53Ψ gene refers to the TP53 gene with mutation at c.673−2A (e.g., c.673−2A>T), as well as to other TP53 gene sequences that comprise the same mutation or an equivalent mutation, such as a mutation at a position corresponding to c.673−2, c.672+1, c.672+2, c.673−1, c.673−2, c.574, c.585_586, c.586, c.591_592, c.592, c.602, c.609_610, c.610, c.615, c.617, c.625, c.637, c.660, c.658_659, c.660, c.661, or c.670, as designated with reference to the TP53 gene. All such p53 variants are referred to as p53Ψ or p53Ψ gene. In specific embodiments, described further herein, a p53 variant comprises a splicing mutation in intron 6 selected from the group consisting of: c.672+1G>A; c.672+1G>C; c.672+1G>T; c.672+2T>A; c.672+2T>C; c.672+2T>G; c.673−1G>A; c.673−1G>C; c.673−1G>T; c.673−2A>C; c.673−2A>G; and c.673−2A>T or a non-sense mutation selected from the group consisting of: c.574C>T; c.585_586CC>TT; c.586C>T; c.591_592GG>TT; c.592G>T; c.602T>A; c.609_610GG>TT; c.610G>T; c.615T>A; c.617T>A; c.625A>T; c.637C>T; c.660T>G; c.658_659ins1; c.660T>A; c.661G>T; and c.670G>T. The product of the mutations described generate p53Ψ isoforms that are transcriptionally inactive isoforms of p53 protein and, as described, reprogram epithelial cells such that they undergo EMT (toward mesenchymal cell status) and toward a metastatic-like state.

Also described are methods of inhibiting (partially or completely) growth or acquisition of mesenchymal features of a (at least one, one or more) cell, particularly cancer cell(s), that expresses p53Ψ. Such phrases as "inhibiting p53Ψ," "inhibition of p53Ψ," and "result in inhibition of p53Ψ" include inhibiting (partially or completely) p53Ψ gene expression, p53Ψ protein activity or both, directly (e.g., by inhibiting or acting directly on p53Ψ gene and/or encoded p53Ψ protein) or indirectly (e.g., by inhibiting or acting on a gene other than p53Ψ gene, a protein other than encoded p53Ψ protein or other cell component with the result that p53Ψ gene expression, p53Ψ protein activity or both are inhibited). In this embodiment, the method of inhibiting (partially or completely) epithelial to mesenchymal transition (EMT) of cells comprises contacting a (at least one, one or more) cyclophilin D (CypD) inhibitor with cell(s) undergoing or likely to undergo EMT, in sufficient concentration and under conditions under which the CypD inhibitor enters the cell(s) in an effective amount and inhibits EMT of the cell(s) or affects growth of the cell(s). In some embodiments, the method further comprises contacting the cell(s) with a reactive oxygen species (ROS) inhibitor. In a specific embodiment, the mutation at nucleotide position c.673−2A (or at an equivalent position) is a substitution of adenine at position c.673−2A of TP53 gene with a guanosine, a cytosine, or a thymine. In another embodiment, the mutation is a substitution mutation at a nucleotide position selected from the group consisting of: c.673−2, c.672+1, c.672+2, c.673−1, and c.673−2 of TP53 gene. In another embodiment, the mutation is a nonsense mutation at a nucleotide position selected from the group consisting of: c.574, c.585_586, c.586, c.591_592, c.592, c.602, c.609_610, c.610, c.615, c.617, c.625, c.637, c.660, c.658_659, c.660, c.661, and c.670 of the TP53 gene. In some embodiments, the methods provided inhibit cell growth (proliferation, survival). In specific embodiments, described further herein, a p53 variant comprises a splicing mutation in intron 6 selected from the group consisting of: c.672+1G>A; c.672+1G>C; c.672+1G>T; c.672+2T>A; c.672+2T>C; c.672+2T>G; c.673−1G>A; c.673−1G>C; c.673−1G>T; c.673−2A>C; c.673−2A>G; and c.673−2A>T or a non-sense mutation selected from the group consisting of: c.574C>T; c.585_586CC>TT; c.586C>T; c.591_592GG>TT; c.592G>T; c.602T>A; c.609_610GG>TT; c.610G>T; c.615T>A; c.617T>A; c.625A>T; c.637C>T; c.660T>G; c.658_659ins1; c.660T>A; c.661G>T; and c.670G>T.

In some embodiments, the method of inhibiting (partially or completely) epithelial to mesenchymal transition (EMT) of cells further comprises contacting cells with an inhibitor of p53Ψ expression or activity. In some embodiments, the method of inhibiting growth of cells further comprises contacting cells with an inhibitor of p53Ψ expression or activity. For example, the method further comprises contacting the cells with an (at least one, one or more) inhibitor of p53Ψ gene expression, an (at least one, one or more) inhibitor of p53Ψ protein activity or a combination of an inhibitor of p53Ψ gene expression and an inhibitor of p53Ψ protein activity, under conditions under which the inhibitor of p53Ψ gene expression, the inhibitor of p53Ψ protein activity or the combination of an inhibitor of p53Ψ gene expression and an inhibitor of p53Ψ protein activity enters the cells. The inhibitor of p53Ψ gene expression, inhibitor of p53Ψ protein activity or combination of an inhibitor of p53Ψ gene expression and an inhibitor of p53Ψ protein activity can be contacted with cells at the same time, before or after the cells are contacted with the CypD inhibitor. In some embodiments, the cells are also contacted with a ROS inhibitor. In some embodiments, the cell is in an individual, such as a human.

A further embodiment is a method of inhibiting (partially or completely) epithelial to mesenchymal transition (EMT) of cells expressing p53Ψ in an individual (e.g., a human), comprising administering to the individual a CypD inhibitor in an effective amount and by a route that results in entry of the CypD inhibitor into cells expressing p53Ψ in sufficient amount to inhibit EMT and inhibition of EMT of the cells. In some embodiments, the method further comprises administering a ROS inhibitor to the individual.

One embodiment is a method of inhibiting (partially or completely) epithelial to mesenchymal transition (EMT) in an individual (e.g., a human) of epithelial cells that comprise a mutation in the TP53 gene at nucleotide position c.673–2A, comprising administering a CypD inhibitor in an effective amount and by a route that results in entry of the CypD inhibitor into cells expressing p53Ψ and inhibition of EMT of the cells. In another embodiment, the mutation is a substitution mutation at a nucleotide position selected from the group consisting of c.673–2, c.672+1, c.672+2, c.673–1, and c.673–2 of TP53 gene. In another embodiment, the mutation is a nonsense mutation at the nucleotide position selected from the group consisting of: c.574, c.585_586, c.586, c.591_592, c.592, c.602, c.609_610, c.610, c.615, c.617, c.625, c.637, c.660, c.658_659, c.660, c.661, and c.670 of the TP53 gene. In specific embodiments, described further herein, a p53 variant comprises a splicing mutation in intron 6 selected from the group consisting of: c.672+1G>A; c.672+1G>C; c.672+1G>T; c.672+2T>A; c.672+2T>C; c.672+2T>G; c.673–1G>A; c.673–1G>C; c.673–1G>T; c.673–2A>C; c.673–2A>G; and c.673–2A>T or a non-sense mutation selected from the group consisting of: c.574C>T; c.585_586CC>TT; c.586C>T; c.591_592GG>TT; c.592G>T; c.602T>A; c.609_610GG>TT; c.610G>T; c.615T>A; c.617T>A; c.625A>T; c.637C>T; c.660T>G; c.658_659ins1; c.660T>A; c.661G>T; and c.670G>T.

In some embodiments, the method further comprises administering to the individual a ROS inhibitor. In some embodiments, the method further comprises administering to the individual an inhibitor of p53Ψ expression or activity (p53Ψ). For example, the method further comprises administering to the individual an inhibitor of p53Ψ gene expression, an inhibitor of p53Ψ protein activity or a combination of an inhibitor of p53Ψ gene expression and an inhibitor of p53Ψ protein activity, in an effective amount and by a route that results in entry of the inhibitor of p53Ψ gene expression, the inhibitor of p53Ψ protein activity or the combination of an inhibitor of p53Ψ gene expression and an inhibitor of p53Ψ protein activity into the cells. The inhibitor of p53Ψ gene expression, inhibitor of p53Ψ protein activity or combination of an inhibitor of p53Ψ gene expression and an inhibitor of p53Ψ protein activity can be administered to the individual at the same time, before or after administration of the CypD inhibitor and/or ROS inhibitor.

Also disclosed is a method of inhibiting (partially or completely) reprogramming of epithelial cells that comprise a mutation in the TP53 gene at position c.673–2A or at a position corresponding to c.673–2A as designated with reference to the TP53 gene and express p53Ψ toward a metastatic-like state in an individual (e.g., a human), comprising administering to the individual a CypD inhibitor in an effective amount and by a route that results in entry of the CypD inhibitor into the epithelial cells and inhibition of reprogramming of the epithelial cells. In specific embodiments, the mutation at nucleotide position c.673–2A is a substitution of an adenine at position c.673–2A with a guanosine, a cytosine, or a thymine. In another embodiment, the mutation is a substitution mutation at a nucleotide position selected from the group consisting of: c.673–2, c.672+1, c.672+2, c.673–1, c.673–2 of TP53 gene. In another embodiment, the mutation is a nonsense mutation at the nucleotide position selected from the group consisting of: c.574, c.585_586, c.586, c.591_592, c.592, c.602, c.609_610, c.610, c.615, c.617, c.625, c.637, c.660, c.658_659, c.660, c.661, and c.670 of the TP53 gene. In specific embodiments, described further herein, a p53 variant comprises a splicing mutation in intron 6 selected from the group consisting of: c.672+1G>A; c.672+1G>C; c.672+1G>T; c.672+2T>A; c.672+2T>C; c.672+2T>G; c.673–1G>A; c.673–1G>C; c.673–1G>T; c.673–2A>C; c.673–2A>G; and c.673–2A>T or a non-sense mutation selected from the group consisting of: c.574C>T; c.585_586CC>TT; c.586C>T; c.591_592GG>TT; c.592G>T; c.602T>A; c.609_610GG>TT; c.610G>T; c.615T>A; c.617T>A; c.625A>T; c.637C>T; c.660T>G; c.658_659ins1; c.660T>A; c.661G>T; and c.670G>T. In some embodiments, the method of inhibiting (partially or completely) reprogramming of such epithelial cells further comprises administering to the individual a ROS inhibitor.

In a further embodiment, the method of inhibiting (partially or completely) reprogramming of such epithelial cells comprises administering to the individual (e.g., a human) an inhibitor of p53Ψ in an effective amount (p53Ψ inhibitor). For example, the method further comprises administering to the individual an inhibitor of p53Ψ gene expression, an inhibitor of p53Ψ protein activity or a combination of an inhibitor of p53Ψ gene expression and an inhibitor of p53Ψ protein activity, in an effective amount and by a route that results in entry of the inhibitor of p53Ψ gene expression, the inhibitor of p53Ψ protein activity or the combination of an inhibitor of p53Ψ gene expression and an inhibitor of p53Ψ protein activity into the cells. The inhibitor of p53Ψ gene expression, inhibitor of p53Ψ protein activity or combination of an inhibitor of p53Ψ gene expression and an inhibitor of p53Ψ protein activity can be administered to the individual at the same time, before or after administration of the CypD inhibitor and/or ROS inhibitor. An effective amount of an inhibitor is an amount that reduces (partially or completely) expression of p53Ψ or reduces activity of p53Ψ.

Also described is a method of treating cancer characterized by p53Ψ expression, comprising administering to an individual (e.g., a human) in need of treatment a CypD inhibitor in an effective amount and by a route that results in entry of the CypD inhibitor into cells that express p53Ψ in a sufficient amount and inhibition of p53Ψ expression and/or inhibition of p53Ψ activity. The method is applicable to treating any cancer in which p53Ψ is expressed. In specific embodiments, the method is useful to treat upper urinary tract transitional cell carcinoma (UUTCC), a non-small-cell lung carcinoma (NSCLC), a cancer of the head and neck, liver cancer, a soft tissue cancer, a hematopoietic cancer, brain cancer, colon cancer, a skin cancer (e.g., melanoma), pancreatic cancer or bladder cancer breast cancer. In some embodiments, the method of treating cancer characterized by p53Ψ expression further comprises administering to the individual a ROS inhibitor. In a further embodiment, the method of treating cancer characterized by p53Ψ expression further comprises administering to the individual (e.g., a human) an inhibitor of p53Ψ in an effective amount. For example, the method further comprises administering to the individual an inhibitor of p53Ψ gene expression, an inhibitor of p53Ψ protein activity or a combination of an inhibitor of p53Ψ gene expression and an inhibitor of p53Ψ protein activity, in an effective amount and by a route that results in entry of the inhibitor of p53Ψ gene expression, the inhibitor of p53Ψ protein activity or the combination of an inhibitor of p53Ψ gene expression and an inhibitor of p53Ψ protein activity into the cells. The inhibitor of p53Ψ gene expression, inhibitor of p53Ψ protein activity or combination of an inhibitor of p53Ψ gene expression and an inhibitor of p53Ψ protein activity can be administered to the individual at the same time, before or after administration of the CypD inhibitor and/or ROS inhibitor. In this embodiment and any other embodiments described herein, in which more than one inhibitor is administered, each inhibitor (e.g., one or more of a CypD inhibitor; a ROS inhibitor; a p53Ψ inhibitor) is administered in an amount, under appropriate conditions (e.g., under conditions under which each inhibitor enters cells comprising p53Ψ) and for sufficient time that the combination is effective in inhibiting (partially or completely) p53Ψ expression, p53Ψ activity or both.

In a specific embodiment, the method of treating cancer that expresses p53Ψ comprises assessing p53Ψ expression in cancer cells obtained from an individual (e.g., a human) in need of cancer treatment; determining whether the cancer cells from the individual express p53Ψ; if cancer cells from the individual express p53Ψ, administering to the individual a CypD inhibitor in an effective amount and by a route that results in entry of the CypD inhibitor into cells that express p53Ψ in sufficient amount and inhibition of p53Ψ expression and inhibition of p53Ψ activity. In some embodiments, the method further comprises administering to the individual a ROS inhibitor.

In an alternative embodiment, the method of treating cancer in an individual (e.g., a human) in need thereof comprises assessing cancer cells obtained from an individual who has received treatment for cancer for expression of p53Ψ; determining whether the cancer cells from the individual express p53Ψ; and, if cancer cells from the individual express p53Ψ, administering to the individual a CypD inhibitor in an effective amount and by a route that results in entry of a sufficient amount of the CypD inhibitor into cells that express p53Ψ and inhibition of p53Ψ expression and inhibition of p53Ψ activity. In some embodiments, the method further comprises administering to the individual a ROS inhibitor.

In another embodiment, the method further comprises administering to the individual an inhibitor of p53Ψ in an effective amount. For example, the method further comprises administering to the individual an inhibitor of p53Ψ gene expression, an inhibitor of p53Ψ protein activity or a combination of an inhibitor of p53Ψ gene expression and an inhibitor of p53Ψ protein activity, in an effective amount and by a route that results in entry of the inhibitor of p53Ψ gene expression, the inhibitor of p53Ψ protein activity or the combination of an inhibitor of p53Ψ gene expression and an inhibitor of p53Ψ protein activity into the cells. The inhibitor of p53Ψ gene expression, inhibitor of p53Ψ protein activity or combination of an inhibitor of p53Ψ gene expression and an inhibitor of p53Ψ protein activity can be administered to the individual at the same time as, before or after administration of the CypD inhibitor and/or ROS inhibitor. An effective amount of an inhibitor is an amount that reduces (partially or completely) expression of p53Ψ or reduces activity of p53Ψ. The CypD inhibitor is a pharmacologic inhibitor or a RNA interference (RNAi) molecule. In specific embodiments, the pharmacologic inhibitor is cyclosporine (e.g., cyclosporine A; CsA), SCY-465, SYC-635, SYC-641, NIM811, Debio 025 (Alisporivir), sanglifehrin A, or a derivative of any of the foregoing molecules. The ROS inhibitor is, for example, a ROS scavenger, such as N-acetyl cysteine or Tempol, or an inhibitor that reduces production of ROS.

Another embodiment is a method of inhibiting in an individual (e.g., a human) epithelial to mesenchymal transition (EMT) of cells that comprise a mutation in the TP53 gene at nucleotide position c.673-2A, comprising administering to the individual an inhibitor of p53Ψ in an effective amount and by a route that results in entry of a sufficient amount of the inhibitor of p53Ψ into cells and inhibition of EMT of the cells. In specific embodiments, the mutation at nucleotide position c.673-2A is substitution of an adenine at position c.673-2A with a guanosine, a cytosine, or a thymine. In another embodiment, the mutation is a substitution mutation at a nucleotide position selected from the group consisting of: c.673-2, c.672+1, c.672+2, c.673-1, c.673-2 of TP53 gene. In another embodiment, the mutation is a nonsense mutation at the nucleotide position selected from the group consisting of: c.574, c.585_586, c.586, c.591_592, c.592, c.602, c.609_610, c.610, c.615, c.617, c.625, c.637, c.660, c.658_659, c.660, c.661, or c.670 of the TP53 gene. In specific embodiments, described further herein, a p53 variant comprises a splicing mutation in intron 6 selected from the group consisting of: c.672+1G>A; c.672+1G>C; c.672+1G>T; c.672+2T>A; c.672+2T>C; c.672+2T>G; c.673−1G>A; c.673−1G>C; c.673−1G>T; c.673−2A>C; c.673−2A>G; and c.673−2A>T or a non-sense mutation selected from the group consisting of: c.574C>T; c.585_586CC>TT; c.586C>T; c.591_592GG>TT; c.592G>T; c.602T>A; c.609_610GG>TT; c.610G>T; c.615T>A; c.617T>A; c.625A>T; c.637C>T; c.660T>G; c.658_659ins1; c.660T>A; c.661G>T; and c.670G>T. The effective amount of the inhibitor of p53Ψ is an amount that reduces expression of p53Ψ or reduces activity of p53Ψ (wherein activity is, for example, increasing mitochondrial pore permeability or inducing production of ROS). An effective amount of the inhibitor of p53Ψ is an amount that reduces expression of p53Ψ in the cells or reduces activity of p53Ψ in the cells. The method can further comprise determining whether cells from the individual express p53Ψ; and, if cancer cells from the individual express p53Ψ, administering to the individual an inhibitor of p53Ψ. Either of these embodiments can further comprise administering (in addition to an inhibitor of p53Ψ) a CypD inhibitor by a route that results in entry of the CypD inhibitor into the cell. In some embodiments, the method further comprises administering to the individual a ROS inhibitor. In those embodiments in which more than one inhibitor is administered, each inhibitor (e.g., one or more of a CypD inhibitor; a ROS inhibitor; a p53Ψ inhibitor) is administered in an amount and for sufficient time that the combination is effective in inhibiting (partially or completely) p53Ψ expression, p53Ψ activity or both. Alternatively, an inhibitor or p53Ψ can be administered to cells that comprise p53Ψ but do not express detectable amounts of p53Ψ protein. For example, the inhibitor can be RNAi. It can be administered in combination with a CypD inhibitor and/or a ROS inhibitor.

Another embodiment is a method of identifying an individual (e.g., a human) suffering from cancer as a candidate for treatment with a CypD inhibitor, comprising determining whether cancer cells from the individual express p53Ψ and identifying the individual as a candidate if cancer cells express p53Ψ. For example, the method comprises assessing p53Ψ expression in cancer cells obtained from an individual (e.g., a human) in need of cancer treatment and determining whether the cancer cells assessed express p53Ψ; if the cancer cells assessed express p53Ψ, the individual is a candidate for treatment with a CypD inhibitor, alone or in combination with another inhibitor or more than one additional inhibitor, such as a ROS inhibitor, a p53Ψ inhibitor or both. The method of identifying an individual suffering from cancer as a candidate for treatment with a CypD inhibitor can further comprise administering to the individual a CypD inhibitor in an effective amount and by a route that results in entry of a sufficient amount of the CypD inhibitor into cells that express p53Ψ to inhibit (partially or completely) p53Ψ expression, p53Ψ activity or both. In some embodiments, the method further comprises administering a ROS inhibitor, an inhibitor of p53Ψ or a combination of a ROS inhibitor and an inhibitor of p53Ψ to the individual, under conditions (e.g., route of administration) under which the ROS inhibitor, the inhibitor of p53Ψ or the combination enter cells that express p53Ψ in amount(s) effective to inhibit (partially or completely) p53Ψ expression, p53Ψ activity or both. In those embodiments in which more than one inhibitor is administered, each inhibitor (e.g., one or more of a CypD inhibitor; a ROS inhibitor; a p53Ψ inhibitor) is administered in an amount and for sufficient time that the combination is effective in inhibiting (partially or completely) p53Ψ expression, p53Ψ activity or both.

In any of the embodiments described, the CypD inhibitor is a pharmacologic inhibitor or a RNA interference (RNAi) molecule. The pharmacologic inhibitor is, for example, cyclosporine (e.g., cyclosporine A; CsA), SCY-465, SYC-635, SYC-641, NIM811, Debio 025 (Alisporivir), sanglifehrin A, or a derivative of any of the foregoing molecules.

One or more CypD inhibitors can be used, alone or in combination with a different type of inhibitor (e.g., one or more CypD inhibitor(s); one or more CypD inhibitors and one or more additional types of inhibitors, such as one or more ROS inhibitor(s) and/or one or more p53Ψ inhibitor(s)).

In any of the embodiments described, the ROS inhibitor is a ROS scavenger or an inhibitor that reduces production of ROS. For example, the ROS inhibitor is alpha-1-microglobulin, superoxide dismutase, catalase, lactoperoxidases, glutathione peroxidases and peroxiredoxins, ascorbic acid (vitamin C), tocopherol (vitamin E), uric acid, glutathione, polyphenol antioxidants, N-actey1 cysteine, Tempol, sodium pyruvate, mannitol, carboxyl-PTIO, Ebselen, sodium azide, MnTBAP, Tiron, Edaravone, catalase, polyethylene glycol-superoxide dismutase (PEG-SOD), manganese (III) tetrakis (1-methyl-4-pyridyl)porphyrin (MnTMPyP), 6-hydroxy-2,5,7,8-tetramethylchroman-2-carboxylic acid (Trolox), deferoxamine, or U-74389G. One or more ROS inhibitors can be used, alone or in combination with a different type of inhibitor (e.g., one or more ROS inhibitor(s); one or more ROS inhibitors and one or more additional types of inhibitors, such as one or more CypD inhibitor(s) and/or one or more p53Ψ inhibitor(s)).

In any of the embodiments described the p53Ψ inhibitor is a pharmacologic inhibitor, a RNA interference (RNAi) molecule and antisense oligonucleotide (ASO) or a CRISPR/Cas9 system that mediates gene editing. One or more p53Ψ inhibitors can be used, alone or in combination with a different type of inhibitor (e.g., one or more p53Ψ inhibitor(s); one or more p53Ψ inhibitors and one or more additional types of inhibitors, such as one or more CypD inhibitor(s) and/or one or more ROS inhibitor(s)).

In any of the embodiments, the method can further comprise evaluating one or more features of the cell(s), in order to assess the effects of an inhibitor on cells expressing p53Ψ. For example, the method can further comprise assessing characteristics such as morphology, invasive ability, motility, or expression of the canonical EMT markers, E-cadherin and Vimentin or of the EMT master regulators Zeb1, Twist, or Slug prior to, during, or after an inhibitor is contacted with a cell or administered to an individual. In some embodiments, decreased invasive ability or motility are indicative of epithelial-like cells.

In some embodiments, expression of cell surface markers or other molecules is assessed. For example, any one or more of the following cell surface molecules is assessed: E-cadherin, CD24, CD104, CD44, CD45, N-cadherin, MUC-1, MUC16, A33, CD43, CD166, PD-L1, B7-H2, B7-H3, Laminin-1, Nectin-1, Nectin-2, Nectin-3, or Nectin-4. In some embodiments, other molecules that may be assessed include Vimentin, Zeb1, Twist, Entactin, collagen, or miR200 family microRNAs. In some embodiments, increased expression of E-cadherin, CD24, CD104, MUC-1, MUC-4, MUC16, A33, CD143, CD166, PD-L1, B7-H2, B7-H3, laminin-1, Nectin-1, Nectin-2, Nectin-3, Nectin-4, cytokeratin, ZO-1, Laminin-1, Entactin, collagen, miR200 family microRNAs, or mir-335 is indicative that a cell is epithelial cell-like. For example, expression of CD44, CD45, N-cadherin, Vimentin, Zeb1, Twist, Slug, or Fibronectin can be assessed; decreased expression of one or more of these markers (relative to expression in control cells, which are, for example, cells, such as cells of the same type, that do not express p53Ψ), is indicative that a cell is epithelial cell-like.

Also described is a method of identifying a cell, such as a human cell, that will undergo epithelial to mesenchymal transition (EMT), comprising determining whether the cell expresses p53Ψ and identifying the cell as a cell that will undergo EMT if p53Ψ is expressed in the cell.

In specific embodiments, a method is provided for identifying a (at least one, one or more) cancer cell, obtained from a human, that will acquire a metastatic-like state, comprising: (a) determining whether cancer cells obtained from a human expresses p53Ψ and (b) if p53Ψ is expressed in the cancer cell, identifying the cancer cell as a cell that will acquire a metastatic-like state.

Another embodiment is a method of predicting that an individual (e.g., a human) will develop cancer, comprising determining whether cells obtained from the individual express p53Ψ and identifying the individual as at increased risk of cancer if the cells comprised express p53Ψ. In this embodiment, cells obtained from a variety of tissues, such as but not limited to, lung, intestine, liver, breast, prostate, kidney, and blood can be assessed.

In a specific embodiment of the method of predicting that an individual will develop cancer, the method further comprises administering to the individual who has been identified as at increased risk of cancer a CypD inhibitor in an effective amount and by a route that results in entry of a sufficient amount of the CypD inhibitor into cells expressing p53Ψ and inhibition of p53Ψ activity. The method can further or alternatively comprise administering an inhibitor of p53Ψ in an effective amount by a route that results in entry of the p53Ψ inhibitor into cells expressing p53Ψ in sufficient concentration and inhibits p53Ψ. In some embodiments, the method further comprises administering to the individual a ROS inhibitor.

Also described here is a method of predicting that an individual (e.g., a human) with cancer in which cancer cells comprise a mutation in the TP53 gene at position c.673−2A or at a position corresponding to c.673−2A as designated with reference to the TP53 gene and express p53Ψ will relapse, comprising determining whether cancer cells of the individual express p53Ψ and, if cells of the individual express p53Ψ, identifying the individual as more likely to relapse than if cells of the individual do not express p53Ψ. In another embodiment, the mutation is a substitution mutation at a nucleotide position selected from the group consisting of c.673−2, c.672+1, c.672+2, c.673−1, c.673−2 of TP53 gene. In another embodiment, the mutation is a nonsense mutation at the nucleotide position selected from the group consisting of c.574, c.585_586, c.586, c.591_592, c.592, c.602, c.609_610, c.610, c.615, c.617, c.625, c.637, c.660, c.658_659, c.660, c.661, or c.670 of the TP53 gene. In specific embodiments, described further herein, a p53 variant comprises a splicing mutation in intron 6 selected from the group consisting of: c.672+1G>A; c.672+1G>C; c.672+1G>T; c.672+2T>A; c.672+2T>C; c.672+2T>G; c.673−1G>A; c.673−1G>C; c.673−1G>T; c.673−2A>C; c.673−2A>G; and c.673−2A>T or a non-sense mutation selected from the group consisting of: c.574C>T; c.585_586CC>TT; c.586C>T; c.591_592GG>TT; c.592G>T; c.602T>A; c.609_610GG>TT; c.610G>T; c.615T>A; c.617T>A; c.625A>T; c.637C>T; c.660T>G; c.658_659ins1; c.660T>A; c.661G>T; and c.670G>T. The method can further comprise administering to the individual who has been identified a CypD inhibitor in an effective amount and by a route that results in entry of the CypD inhibitor into cells expressing p53Ψ and inhibition of p53Ψ. The CypD inhibitor is a pharmacologic inhibitor or a RNA interference (RNAi) molecule, an antisense oligonucleotide (ASO) or a CRISPR/Cas9 system that mediates gene editing. In specific embodiments, the pharmacologic inhibitor is cyclosporine (e.g., cyclosporine A; CsA), SCY-465, SYC-635, SYC-641, NIM811, Debio 025 (Alisporivir), sanglifehrin A, or a derivative of any of the foregoing molecules. An ASO can be, for example, a p53Ψ modified oligonucleotide that targets at least a region of the TP53 sequence between g. 12627 and g. 13900, based on the TP53 NC-000017.10 genome sequence reference The ROS inhibitor is, for example, a ROS scavenger, such as N-acetyl cysteine or Tempol, or an inhibitor that reduces production of ROS. In a further embodiment, the method comprises administering an inhibitor of p53Ψ in an effective amount.

Another embodiment is a method of identifying an individual (e.g., a human) diagnosed with/suffering from cancer who is likely to respond to treatment with a CypD inhibitor, a ROS inhibitor, a p53Ψ inhibitor or a combination of two or three of a CypD inhibitor, a ROS inhibitor and a p53Ψ inhibitor, comprising determining whether the individual has consumed aristolochic acid, thus identifying the individual as more likely to respond to such treatment than if the individual had not consumed aristolochic acid and determining whether cancer cells of the identified individual [comprise a mutation in the TP53 gene at position c.673−2A or at a position corresponding to c.673−2A as designated with reference to the TP53 gene and] express p53Ψ. If the cancer cells comprise a mutation in the TP53 gene at position c.673−2A or at a position corresponding to c.673−2A as designated with reference to the TP53 gene and express p53Ψ, the individual is likely to respond to such treatment. In another embodiment, the mutation is a substitution mutation at a nucleotide position selected from the group consisting of: c.673−2, c.672+1, c.672+2, c.673−1, c.673−2 of TP53 gene. In another embodiment, the mutation is a nonsense mutation at the nucleotide position selected from the group consisting of: c.574, c.585_586, c.586, c.591_592, c.592, c.602, c.609_610, c.610, c.615, c.617, c.625, c.637, c.660, c.658_659, c.660, c.661, or c.670 of the TP53 gene. The cancer can be any type in which p53Ψ is expressed and, in specific embodiments, upper urinary tract transitional cell carcinoma (UUTCC) or a non-small-cell lung carcinoma (NSCLC).

The method of identifying an individual diagnosed with/suffering from cancer who is likely to respond to treatment with a CypD inhibitor, a ROS inhibitor, a p53Ψ inhibitor or a combination of two or three of a CypD inhibitor, a ROS inhibitor and a p53Ψ inhibitor can further comprise administering to the individual a CypD inhibitor, a ROS inhibitor, a p53Ψ inhibitor or a combination of two or three of a CypD inhibitor, a ROS inhibitor and a p53Ψ inhibitor in an effective amount by a route that results in entry of the CypD inhibitor, the ROS inhibitor, the p53Ψ inhibitor or the combination of two or three of a CypD inhibitor, a ROS and a p53Ψ inhibitor into cells expressing p53Ψ and inhibition of p53Ψ activity. In those embodiments in which more than one inhibitor is administered, each inhibitor (e.g., one or more of a CypD inhibitor; a ROS inhibitor; a p53Ψ inhibitor) is administered in an amount and for sufficient time that the combination is effective in inhibiting (partially or completely) p53Ψ expression, p53Ψ activity or both.

In any embodiments in which expression of p53Ψ in cells is assessed or determined, the presence and/or amount of p53Ψ, the activity of p53Ψ, or localization of p53Ψ in the cell can be determined.

Also described are pharmaceutical compositions that comprise at least two of the following: a CypD inhibitor, a ROS inhibitor, a p53Ψ inhibitor and a ROS signaling inhibitor. In one embodiment, the pharmaceutical composition comprises at least two CypD inhibitors; at least two ROS inhibitors; at least two p53Ψ inhibitors; or at least two ROS signaling inhibitors. In a further embodiment, the pharmaceutical composition comprises at least a (one or more, at least one) CypD inhibitor and a (one or more, at least one) ROS inhibitor; a (one or more, at least one) CypD inhibitor and a (one or more, at least one) p53Ψ inhibitor; a (one or more, at least one) ROS inhibitor and a (one or more, at least one) p53Ψ inhibitor; at least a (one or more, at least one) CypD inhibitor and a (one or more, at least one) ROS signaling inhibitor; at least a (one or more, at least one) ROS inhibitor and a (one or more, at least one) ROS signaling inhibitor; or at least a (one or more, at least one) ROS signaling inhibitor and a (one or more, at least one) p53Ψ inhibitor. A pharmaceutical composition can comprise a (one or more, at least one) CypD inhibitor; a (one or more, at least one) ROS inhibitor; and a (one or more, at least one) p53Ψ inhibitor. In each embodiment, the pharmaceutical composition also comprises an acceptable carrier, such as water, saline, or physiologically acceptable buffer and, optionally, some or all of stabilizing agents, excipients, and solubilizing agents.

Also described is use of a CypD inhibitor, a p53Ψ inhibitor, a ROS inhibitor, a ROS signaling inhibitor or a combination of two, three or four of the inhibitors (e.g., CypD inhibitor and a p53Ψ inhibitor; a CypD inhibitor and a ROS inhibitor; a p53Ψ inhibitor and a ROS inhibitor; a CypD inhibitor and a ROS signaling inhibitor; a p53Ψ inhibitor and a ROS signaling inhibitor; a ROS inhibitor and a ROS signaling inhibitor; a CypD inhibitor, a p53Ψ inhibitor and a ROS signaling inhibitor; a p53Ψ inhibitor, a ROS inhibitor and a ROS signaling inhibitor; a CypD inhibitor, a ROS inhibitor and a ROS signaling inhibitor; a CypD inhibitor, a p53Ψ inhibitor, and a ROS inhibitor; a CypD inhibitor and a ROS signaling inhibitor; a p53Ψ inhibitor and a ROS signaling inhibitor) in the treatment of cancer in which cancer cells express p53Ψ. Specific embodiments are use of a CypD inhibitor such as an RNA interference (RNAi) molecule that targets CypD mRNA and use of a pharmacologic inhibitor of cyclophilin, such as, but not limited to, cyclosporine, cyclosporine A (CsA), SYC-635, SYC-465, SYC-641, NIM811, Debio 025 (Alisporivir), sanglifehrin A, and derivatives of any of the foregoing molecules in the treatment of cancer in which cancer cells express p53Ψ. Further specific embodiments are use of a ROS inhibitor that is a ROS scavenger or an inhibitor that reduces production of ROS. For example, the ROS inhibitor is alpha-1-microglobulin, superoxide dismutase, catalase, lactoperoxidases, glutathione peroxidases and peroxiredoxins, ascorbic acid (vitamin C), tocopherol (vitamin E), uric acid, glutathione, polyphenol antioxidants, N-acteyl cysteine, Tempol, sodium pyruvate, mannitol, carboxyl-PTIO, Ebselen, sodium azide, MnTBAP, Tiron, Edaravone, catalase, polyethylene glycol-superoxide dismutase (PEG-SOD), manganese (III) tetrakis (1-methyl-4-pyridyl)porphyrin (MnTMPyP), 6-hydroxy-2,5,7,8-tetramethylchroman-2-carboxylic acid (Trolox), deferoxamine, or U-74389G.

Further described is use of a CypD inhibitor, a p53Ψ inhibitor, a ROS inhibitor, a ROS signaling inhibitor or a combination of two, three or four of the inhibitors (e.g., CypD inhibitor and a p53Ψ inhibitor; a CypD inhibitor and a ROS inhibitor; a p53Ψ inhibitor and a ROS inhibitor; a CypD inhibitor and a ROS signaling inhibitor; a p53Ψ inhibitor and a ROS signaling inhibitor; a ROS inhibitor and a ROS signaling inhibitor; a CypD inhibitor, a p53Ψ inhibitor and a ROS signaling inhibitor; a p53Ψ inhibitor, a ROS inhibitor and a ROS signaling inhibitor; a CypD inhibitor, a ROS inhibitor and a ROS signaling inhibitor; a CypD inhibitor, a p53Ψ inhibitor, and a ROS inhibitor; a CypD inhibitor and a ROS signaling inhibitor; a p53Ψ inhibitor and a ROS signaling inhibitor) in the treatment of cancer characterized by expression of one or more cell biomarkers of the mesenchymal state. Such cells are characterized, for example, by increased expression of one or more mesenchymal protein, such as CD44, CD45, N-cadherin, Fibronectin, Snail, Slug, Twist, Zeb1, CD44, and Vimentin and/or by phenotypic properties of a mesenchymal cell, such as cellular morphology; resistance to chemotherapeutic agents. They can also be characterized by decreased expression of one or more proteins associated with the epithelial state, such as E-cadherin or CD24, or a reduction in any phenotype, morphology, of functional property associated with epithelial cells. In specific embodiments, the cancer cells are characterized by high expression of CD44 (CD44$^{high}$) and low expression of CD24 (CD24$^{low}$). Specific embodiments are use of a CypD inhibitor such as an RNA interference (RNAi) molecule that targets CypD mRNA and use of a pharmacologic inhibitor of cyclophilin, such as, but not limited to, cyclosporine, cyclosporine A (CsA), SYC-635, SYC-465, SYC-641, NIM811, Debio 025 (Alisporivir), sanglifehrin A, and derivatives of any of the foregoing molecules in the treatment of cancer characterized by expression of one or more cell biomarkers of the mesenchymal state. Further specific embodiments are use of a ROS inhibitor that is a ROS scavenger or an inhibitor that reduces production of ROS. For example, the ROS inhibitor is alpha-1-microglobulin, superoxide dismutase, catalase, lactoperoxidases, glutathione peroxidases and peroxiredoxins, ascorbic acid (vitamin C), tocopherol (vitamin E), uric acid, glutathione, polyphenol antioxidants, N-acteyl cysteine, Tempol, sodium pyruvate, mannitol, carboxyl-PTIO, Ebselen, sodium azide, MnTBAP, Tiron, Edaravone, catalase, polyethylene glycol-superoxide dismutase (PEG-SOD), manganese (III) tetrakis (1-methyl-4-pyridyl)porphyrin (MnTMPyP), 6-hydroxy-2,5,7,8-tetramethylchroman-2-carboxylic acid (Trolox), deferoxamine, or U-74389G.

Further described is use of a CypD inhibitor, a p53Ψ inhibitor, a ROS inhibitor a ROS signaling inhibitor or a combination of two, three or four of the (e.g., CypD inhibitor and a p53Ψ inhibitor; a CypD inhibitor and a ROS inhibitor; a p53Ψ inhibitor and a ROS inhibitor; a CypD inhibitor and a ROS signaling inhibitor; a p53Ψ inhibitor and a ROS signaling inhibitor; a ROS inhibitor and a ROS signaling inhibitor; a CypD inhibitor, a p53Ψ inhibitor and a ROS signaling inhibitor; a p53Ψ inhibitor, a ROS inhibitor and a ROS signaling inhibitor; a CypD inhibitor, a ROS inhibitor and a ROS signaling inhibitor; a CypD inhibitor, a p53Ψ inhibitor, and a ROS inhibitor; a CypD inhibitor and a ROS signaling inhibitor; a p53Ψ inhibitor and a ROS signaling inhibitor) in inhibiting in an individual epithelial to mesenchymal transition (EMT) of cells that comprise a mutation in the TP53 gene at nucleotide position c.673–2A., as described herein. Specific embodiments are use of a CypD inhibitor, a p53Ψ inhibitor, a ROS inhibitor or a combination of two or three of the inhibitors (e.g., CypD inhibitor and a p53Ψ inhibitor; a CypD inhibitor and a ROS inhibitor; a p53Ψ inhibitor and a ROS inhibitor; a CypD inhibitor, a p53Ψ inhibitor, and a ROS inhibitor) in inhibiting EMT of cells that comprise a mutation at nucleotide position c.673–2A that is substitution of an adenine at position c.673–2A with a guanosine, a cytosine, or a thymine. In other embodiments, the mutation is a substitution mutation at a nucleotide position selected from the group consisting of: c.673–2, c.672+1, c.672+2, c.673–1, c.673–2 of TP53 gene. In another embodiment, the mutation is a nonsense mutation at the nucleotide position selected from the group consisting of: c.574, c.585_586, c.586, c.591_592, c.592, c.602, c.609_610, c.610, c.615, c.617, c.625, c.637, c.660, c.658_659, c.660, c.661, or c.670 of the TP53 gene. In specific embodiments, described further herein, a p53 variant comprises a splicing mutation in intron 6 selected from the group consisting of: c.672+1G>A; c.672+1G>C; c.672+1G>T; c.672+2T>A; c.672+2T>C; c.672+2T>G; c.673–1G>A; c.673–1G>C; c.673–1G>T; c.673–2A>C; c.673–2A>G; and c.673–2A>T or a non-sense mutation selected from the group consisting of: c.574C>T; c.585_586CC>TT; c.586C>T; c.591_592GG>TT; c.592G>T; c.602T>A; c.609_610GG>TT; c.610G>T; c.615T>A; c.617T>A; c.625A>T; c.637C>T; c.660T>G; c.658_659ins1; c.660T>A; c.661G>T; and c.670G>T.

Also described is a companion diagnostic, such as an assay of a marker that reflects or is indicative of the health status of an individual and provides information about the status of an individual. It can be used to help caregivers, such as physicians, identify or confirm appropriate treatment for the individual. For example, an assay can be carried out to determine if cancer cells obtained from an individual express p53Ψ or exhibit characteristics of cells likely to undergo EMT or become metastatic. If cancer cells obtained from an individual are characterized by p53Ψ expression, treatment using any combination of a CypD inhibitor, a ROS inhibitor and a p53Ψ inhibitor is indicated. Described herein are biomarkers that can be used in such a companion diagnostic and kits that comprise reagents that detect the biomarker(s). A physician can use information obtained from the combination diagnostic assay to determine if a particular therapy is appropriate for an individual and the amount per treatment, number of treatments or frequency of treatments to be administered to the individual.

BRIEF DESCRIPTION OF DRAWINGS

The accompanying drawings are not intended to be drawn to scale. The figures are illustrative only and are not required for enablement of the disclosure. For purposes of clarity, not every component may be labeled in every drawing. In the drawings:

FIG. 1A presents a schematic of the naphthalene lung injury model. FIG. 1B shows FACS analysis of lung cell suspensions at different time points after injury with naphthalene. CD31- and CD45- negative cells were utilized to remove endothelial cells and bone marrow derived cells, respectively. The right panel shows the accumulation of CD44high/CD24low cells over 21 days. Values in the right upper corners represent % of CD44high/CD24low cells relative to CD31-/CD45- cells. FIG. 1C presents relative expression of multiple p53 targets in CD44low/CD24high (CD44L) cells sorted from naphthalene-injured mice compared to levels in CD44high/CD24low (CD44H) cells. FIG. 1D shows RT-PCR analysis of lung tissue extracts obtained at the indicated time points after naphthalene treatment using oligonucleotide primers to exons 6 and 8 (ex6-ex8, upper panel) and primers specific for p53Ψ (460-ex8, middle panel). Actin was used for normalization. FIG. 1E shows sequence analysis of the two PCR products amplified with p53 primers indicated the use of a novel splice junction between exon 6 and exon 8 in the shorter p53 transcript. The sequences in FIG. 1E, from left to right, correspond to SEQ ID NO: 12 and SEQ ID NO: 13. FIG. 1F shows RT-PCR analysis of lung tissue obtained after naphthalene treatment at the indicated time points using primers specific for p53FL and p53Ψ. FIG. 1G shows RT-PCR analysis of liver tissue after CCL4 treatment using oligonucleotide primers specific for p53FL and the p53Ψ isoform at the indicated time points. FIG. 1H shows tissue sections of CCL4-injured livers that were hybridized with RNA FISH probes specific for p53Ψ (left column), smooth muscle actin (SMA, middle column), and DNA (DAPI, right column).

FIG. 2A shows expression of p53Ψ in two representative lung adenocarcinoma tumor cores characterized by high percentages of CD44highCD24low cells (left) or CD44lowCD24high cells (right). Staining with p53Ψ sense (SE) and antisense (AS) probes are shown in the panels on the right. DAPI was used as a counterstain. FIG. 2B presents charts that show the distribution of p53Ψ mRNA expression in CD44highCD24low NSCLC tumors. FIG. 2C shows the Kaplan-Meyer distribution of p53Ψ-positive and -negative NSCL tumors. FIG. 2D shows semi-quantitative RT-PCR analysis of p53FL and p53Ψ in CD44high/CD24low cells sorted from multiple human cancer-derived cell lines. FIG. 2E presents a pie chart showing the distribution of mutations at position c.673-2A in 28,581 tumors as reported in the International Agency for Research on Cancer (IARC) p53 database. FIG. 2F shows results from TP53 gene mutation analysis of a collection of 172 upper urinary tract transitional carcinoma (UUTCC) cases. The number of missense mutations (top) and mutations predicted to affect the TP53 splicing pattern (bottom) is shown. FIG. 2G schematically presents a minigene that can be used to assess p53 splicing. The sequence in FIG. 2G corresponds to SEQ ID NO: 14. FIG. 2H shows RT-PCR analysis of transcripts from the minigene utilizing primers to the CMV promoter and exon 8. The presence of a G in position −2 relative to the first nucleotide in exon 7 resulted in the generation of an alternative transcript of the expected size of a p53Ψ-like transcript (PSI). Sequence analysis confirmed that this transcript was the result of the use of the same cryptic acceptor site in intron 6 that is utilized for the generation of p53Ψ. FIG. 2I shows RT-PCR analyses of cells expressing p53FL (A549) and a c.673-2A to G mutation in TP53 (HOP62) indicating that the latter induces the generation of a p53Ψ-like transcript. Primers spanning exons 4 to 7 were used for PCR-amplification of transcripts. FIG. 2L presents a representative Western blot of A549 and HOP62 cells extracts using an N-terminal p53 antibody indicating that the HOP62 cells inherently express a p53Ψ-like protein of the expected size.

FIG. 3A depicts a schematic representation of p53Ψ and p53FL. The sequence in FIG. 3A corresponds to SEQ ID NO: 15. FIG. 3B shows a representative Western blot analysis indicating that ectopic expression of the novel p53 isoform in A549 cells generated a protein approximately 27 kDa in size. FIG. 3C shows immunofluorescence micrographs revealing a predominantly cytoplasmic, partly punctate localization of p53Ψ (bottom panel). Phalloidin and DAPI were used as counterstains to highlight actin fibers and the nucleus, respectively. FIG. 3D presents sub-cellular fractionation of A549 cells expressing p53Ψ or a vector control. These results support a cytoplasmic distribution of the p53Ψ protein isoform. Equal amounts of whole cell lysate (T) and cytoplasmic (C) and nuclear (N) protein fractions were analyzed by Western blotting using an antibody directed against the N-terminal domain of p53 (DO1). Tubulin and uncleaved PARP were used as controls for cytoplasmic and nuclear fractions, respectively. FIG. 3E presents expression of known p53 targets p21, Puma, Tigar in H1299 cells ectopically expressing p53Ψ, p53FL, or a vector control. mRNA levels were quantified by SYBR-green-based real-time RT-PCR in tetracycline-inducible p53-null cells (H1299) ectopically expressing p53FL or p53Ψ upon induction with doxycycline (0.5 µg/ml) for 5 days. Columns represent relative expression values ($p<0.0001$, Student's t-test). FIG. 3F shows a dual luciferase reporter assay in H1299 cells in which ectopic expression of p53Ψ fails to activate the synthetic p53-responsive promoter p21Cip1-luc. Luciferase activity was normalized to *Renilla* activity. Data shown are representative of three independent experiments ($p=0.03241$). Cells were treated with doxycycline (0.5 µg/ml) for 3 days prior to the assay. FIG. 3G shows that ectopic expression of p53Ψ in cells expressing endogenous p53FL (A549 cells) did not induce expression of known p53 targets. In order to increase p53 activity, cells were treated with the DNA damaging agent doxorubicin for 24 hours. The graph represents relative mRNA levels of the indicated p53 targets upon treatment with doxorubicin (1 µM). Data represent relative expression levels compared to actin (mean±SD, n=6; $p<0.0001$, Student's t-test) as measured by SYBR-green-based real-time PCR.

FIG. 4A shows that silencing of p53Ψ in HOP62 cells that inherently and exclusively express p53Ψ resulted in loss of mesenchymal-like features and the acquisition of an epithelial morphology. Representative micrographs are presented showing cells 4 days after transfection with a mixture of two independent siRNA oligonucleotides targeting p53. FIG. 4B shows qRT-PCR analysis of the canonical EMT markers E-cadherin (ECAD) and vimentin (VIM), as well as the EMT master regulators Slug, Twist, and Zeb1 in HOP62 cells upon inhibition of p53 with two different siRNAs. No difference in Snail expression was observed. Data shown represent relative expression levels compared to actin (mean±SD, n=6; p<0.0001, Student's t-test) as measured by SYBR-green-based real-time RT-PCR. The HOP62 cells do not express p53FL. FIG. 4C shows representative scanning electron micrographs of MCF7 and A549 cells in which ectopic expression of p53Ψ resulted in the acquisition of morphological features characteristic of cells undergoing an EMT. Level of expression of p53FL and p53Ψ in MCF7 are provided in FIGS. 11B and 10E, respectively. FIG. 4D presents qRT-PCR analysis of the canonical EMT markers E-cadherin (ECAD) and vimentin (VIM) as well as the EMT master regulators Snail, Slug, Twist, and Zeb1, in H1299 cells ectopically expressing p53Ψ or p53FL. Data shown represent relative expression levels compared to actin (mean±SD, n=6; p<0.0001, Student's t-test) as measured by SYBR-green-based real-time RT-PCR. FIG. 4E depicts the percent wound closure at the indicated time points in a 2D monolayer of A549 cells expressing p53Ψ, p53FL, or vector control. Each bar shows the mean value from four wounds and the standard deviation from the mean (p≤0.0001 by Student's t-test). FIG. 4F shows the invasive potential of the indicated cells after induction for 5 days with doxycycline (0.5 μg/ml) in a standard Matrigel invasion assay. Filter chambers were coated with 40 μl Matrigel, and invasion was assessed after 30 hours. TGF-β treated cells were used as a positive control.

FIG. 5A presents representative immunostaining analysis of H1299 cells revealing a partial mitochondrial localization of p53Ψ. Mitochondrial GFP and cyclophilin D (CypD), a mitochondrial matrix protein were used as counterstains to highlight the mitochondria. The cell nuclei were stained with DAPI. FIG. 5B shows Western blot analysis of H1299 cells identifying the localization of p53FL and p53Ψ in different submitochondrial fractions. P53Ψ was primarily found within the inner membrane/matrix fraction (im/ma). Detection of CypD and COX IV were used to control for purity of the inner membrane/matrix fraction, high-mobility group box 1 (HMGB) for the nuclear fraction, PORIN for the outer membrane fraction, and TUBULIN for the cytosolic fraction. FIG. 5C shows Western blot analysis of fractionated cells to analyze the distribution of p53Ψ upon Tid-1 knockdown in A549 cells. FIG. 5D shows Western blot analysis of fractionated cells to analyze the distribution of mitochondrial bound p53Ψ (Mito-p53Ψ) upon TID-1 knockdown in A549 cells. p53Ψ mitochondrial localization was determined 72 hours after transfection with Tid-1-specific siRNA. Detection of CypD (a mitochondrial matrix protein) and p120 RasGAP (a cytoplasmic protein) were used as controls for purity of the mitochondrial fractions. FIG. 5E shows Western blot analysis of protein extracts from A549 cells ectopically expressing p53Ψ. FIG. 5F shows Western blot analysis of protein extracts from A549 cells ectopically expressing mito-p53Ψ, indicating that Tid-1 is required for p53Ψ-induced reduction of E-cadherin levels.

FIG. 6A-F shows that p53Ψ interaction with cyclophylin D is sufficient to increase the mPTP permeability and reactive oxygen production. FIG. 6A presents Western blot analysis of mitochondrial fractions of A549 cells ectopically expressing p53Ψ. The fractions were immunoprecipitated with a CypD-specific antibody and probed with a p53 N-terminal antibody, or CypD and Smurf1 antibodies as controls. This analysis demonstrates an interaction between p53Ψ and CypD in the mitochondrial fraction. FIG. 6B depicts a schematic of the calcein AM assay. FIG. 6C shows representative fluorescence microscopy images of A549 cells that were loaded with 10 nM calcein. The fluorescence was detected by laser confocal microscopy after 15 minutes. Non-mitochondrial calcein fluorescence was quenched by co-treatment with CoCl2. Treatment with the ionophore ionomycin (50 nM) was used as a control. Cyclosporin A (CsA) was used at 2 mM. FIG. 6D presents the % decrease in calcein fluorescence upon quenching of cytosolic calcein with CoCl2 in three independent experiments. The median calcein fluorescence was assessed by FACS. Calcein was loaded at 10 nM and detected after 15 minutes at 515 nm upon excitation with Red HeNe at 495 nm. Treatment with ionomycin was used as a control to estimate basal fluorescence. FIG. 6E presents representative fluorescence microscopy images of A549 cells loaded with MitoSOX (1 μM). Images show the fluorescence upon excitation at 390 nm, mainly from the hydroxyethidium derivative. DAPI was used as a counterstain. FIG. 6F presents the quantification of the MitoSox-positive fractions in three independent FACS experiments from FIG. 6E.

FIG. 7A presents Western blot analysis of A549 cells ectopically expressing p53Ψ upon transfection with two independent siRNA targeting cyclophilin D (CypD). FIG. 7B shows that treatment with CsA, a highly specific and potent pharmacological inhibitor of CypD, is sufficient to restore expression of E-cadherin to a level similar to that observed in control cells, and to reduce expression of EMT markers in cells ectopically expressing p53Ψ. The graph presents qRT-PCR analysis of the canonical EMT markers E-cadherin (ECAD) and vimentin (VIM) as well as the EMT master regulators Snail, Slug, Twist, and Zeb1 in H1299 cells ectopically expressing p53Ψ upon treatment with 2 mM CsA for 5 days. Data represent expression levels compared to actin (mean±SD, n=6; p<0.0001, Student's t-test) as measured by SYBR-green-based real-time RT-PCR. Similar results were observed in MCF7 cells. FIG. 7C shows motility of A549 cells ectopically expressing p53FL or p53Ψ after treatment with CsA for 5 days. Cell motility was measured in a standard wound healing experiment. The chart indicates the percentage of closure at 48 hours in the presence or absence of 2 mM CsA. Each bar represents the average of four individual wounds. The histogram shows the mean value+ SD (p≤0.0001 by Student's t-test). FIG. 7D shows that treatment with low but increasing concentrations of H2O2 is sufficient to decrease expression of E-cadherin to levels similar to those observed in cell lines ectopically expressing p53Ψ. mRNA levels of E-cadherin were assessed by SYBR-green real-time RT-PCR upon treatment with H2O2 for 5 days. Data represent relative expression compared to the vector control (mean±SD, n=6; p<0.0001, Student's t-test). FIG. 7E shows that reduction of ROS levels is sufficient to enhance expression of E-cadherin levels in cells expressing p53Ψ. Cells were treated for 5 days with 10 mM NAC. FIG. 7F presents a schematic of a proposed mechanism of the p53Ψ-induced EMT. Upon acute oxidative stress, p53FL was previously shown to interact with CypD and trigger necrotic cell death by opening mPTP pore (left panel).

FIG. 8A shows that CD44highCD24low cells sorted from naphthalene-injured lungs have decreased levels of expression of p53 target genes. Lung cell suspensions were sorted by FACS 15 days after naphthalene injury. CD31- and CD45-negative EPCAM+ cells were further sorted based on the surface expression of CD24 and CD44. SYBR-green-based real-time RT-PCR analysis of CD44highCD24low and CD44low CD24high cells was performed to determine expression levels of p53 targets. Each bar represents the relative mRNA level of the indicated gene in CD44low CD24high cells as compared to CD44highCD24low cells. FIG. 8B presents a schematic of the alternative-splicing event that leads to the generation of p53Ψ in humans and mice. The sequence of p53Ψ is in bold. TP53 has 11 exons. Use of a cryptic splicing site within intron 6 leads to production of an alternative transcript dubbed "p53Ψ" that is characterized by the insertion of an additional 49 bp in humans and 55 bp in mice. The sequences in FIG. 8B, from top to bottom, correspond to SEQ ID NO: 16 and SEQ ID NO: 17. FIG. 8C shows a cross-species comparison of the TP53 genomic sequence revealing there is a high level of homology at the alternative splicing site between species. The sequences in FIG. 8C, from top to bottom, correspond to SEQ ID NOs: 18-23. FIG. 8D presents a schematic of the PCR strategy utilized to specifically amplify p53Ψ. FIG. 8E shows differential expression of p53 Ψ in CD44highCD24low and CD44lowCD24high cells sorted from naphthalene-injure lung. Lung cells suspensions were sorted by FACS 15 days after naphthalene injury. CD31- and CD45-negative/EPCAM+ cells were further sorted based on the CD24 and CD44 surface markers. RT-PCR analysis of CD44highCD24low and CD44low CD24high cells was performed using oligonucleotide primers specific for p53Ψ and oligonucleotide primers for CD44, CD24 and E-cadherin were used as controls. Actin expression was used for normalization. FIG. 8F shows that p53Ψ is not expressed in mouse tissues under normal physiological conditions. RNA was extracted from the indicated murine tissues and amplified using oligonucleotides spanning the exon 6 to exon 8. FIG. 8G shows fluorescence micrographs validating the p53Ψ and p53FL probes. Cells inherently expressing p53FL (top) or p53Ψ (bottom) are probed by RNA hybridization with antisense and sense probes specific for p53FL and p53Ψ.

FIG. 9A presents a schematic of the probes utilized for RNA fluorescence in situ hybridization. FIG. 9N shows RT-PCR analysis using multiple primer pairs spanning the entire TP53 gene indicating p53Ψ in Hop62 cells is expressed as a TAp53-alpha isoform.

FIG. 10A presents fluorescence micrographs of HOP62 cells showing that p53Ψ is localized in the cell cytoplasm. The cell nuclei were stained with DAPI. FIG. 10B presents a Western blot analysis of H1299 cells ectopically expressing p53FL or p53Ψ. FIG. 10C presents a Western blot analysis of tetracycline-inducible expression of p53FL or p53Ψ in A549 cells. Expression of p53 and p53 targets (p21CIP1 and BAX) was assessed in the presence or absence of doxycycline induction (0.5 µg/ml) for 3 days. Alpha-tubulin was used as a loading control. FIG. 10D shows real-time PCR of RNA extracts obtained from A549 cells ectopically expressing p53FL or p53Ψ in the presence and absence of doxycycline induction (0.5 µg/ml). Cells were grown for 3 days in the presence of doxycycline. Expression of BAX and p21Cip1 are shown relative to actin expression.

FIG. 11A shows a Western blot analysis of E-cadherin levels in Hop62 cells upon p53Ψ siRNA knock-down. RAS-Gap was used as a normalization control. FIG. 11B shows Western blot analysis of MCF7 cells ectopically expressing p53Ψ. FIG. 11C shows real-time PCR of MCF7 and A549 cells ectopically expressing p53Ψ and p53FL. Data are represented as relative expression compared to vector control (mean±SD, n=6; p<0.0001, Student's t-test). FIG. 11D shows a Western blot analysis of tetracycline-inducible expression of p53Ψ or p53FL in A549 cells. Induction of p53Ψ and p53FL expression was achieved by stimulating the cells with doxycycline (0.5 µg/ml) for 5 days. Despite the very low p53Ψ levels (asterisks) observed in untreated cells, it was sufficient to decrease expression of E-cadherin. FIG. 11E shows sub-cellular localization of E-cadherin in A549 cells ectopically expressing p53Ψ or p53FL. Diminished E-cadherin at cell-cell junctions was observed in A549 cells expressing p53Ψ. Cells were immunostained following induction with doxycycline (0.5 μg/ml) for 5 days. Nuclei are shown with DAPI labeling.

Figure 12:
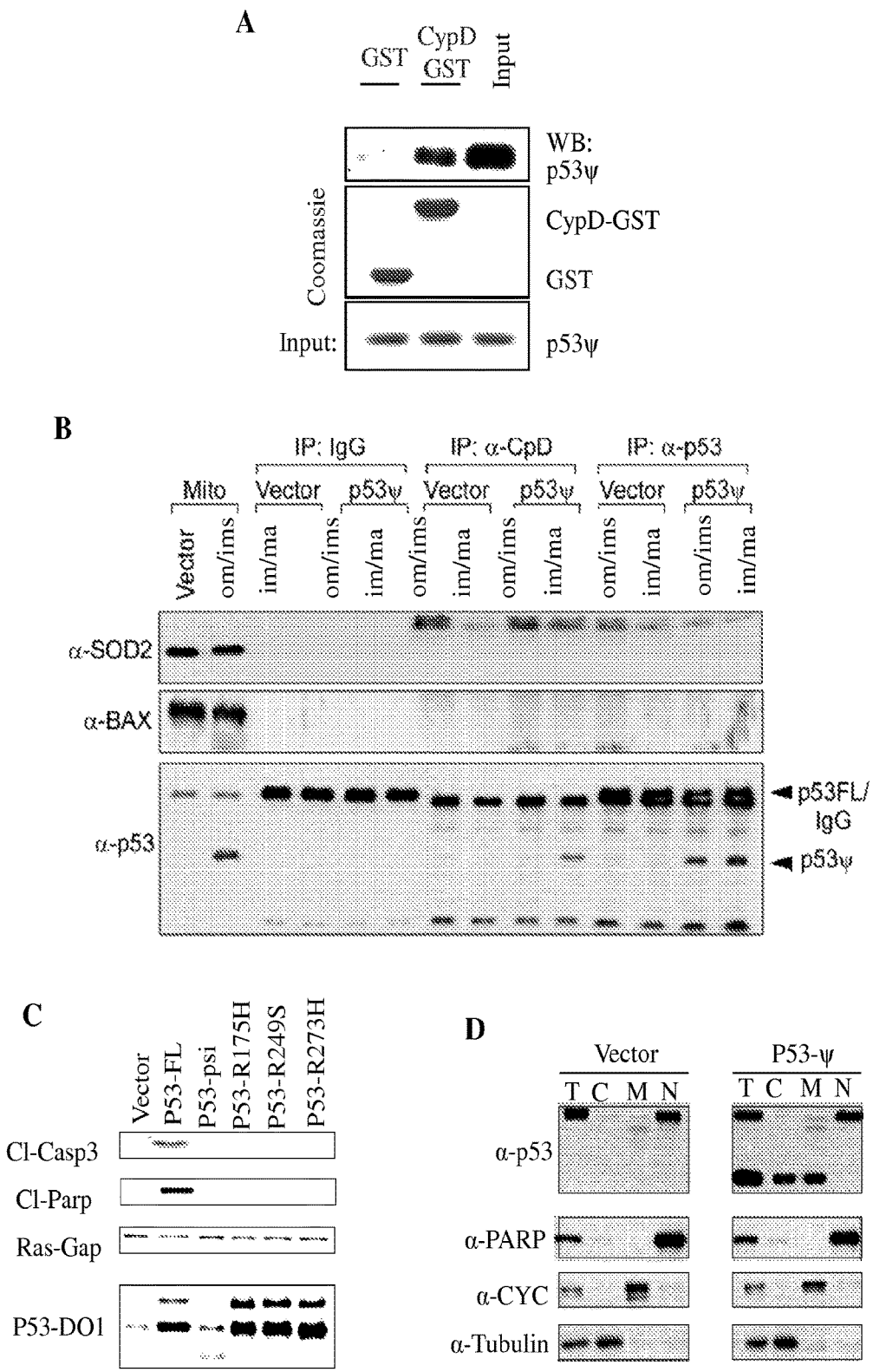
Figure 12:
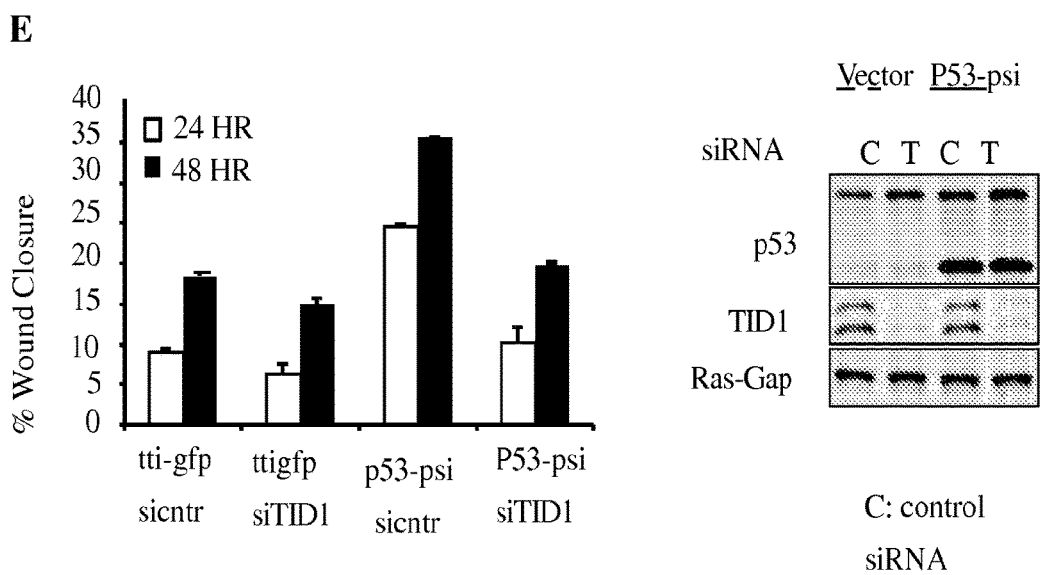

FIG. 12A-E shows that purified p53Ψ directly interacts with CypD. FIG. 12A shows the results of pull-down assays indicating direct binding of purified p53Ψ (aa 102-243) to purified CypD-GST but not empty GST proteins. FIG. 12B shows that p53Ψ fails to interact with SOD2 and BAX. Extracts from different submitochondrial fractions of A549 cells expressing p53Ψ or vector only were immunoprecipitated with an anti-p53 N-terminal antibody, then immunoblotted with anti-SOD2, -BAX, or -p53 antibodies. FIG. 12C shows a Western blot analysis evaluating cleaved caspase 3 and cleaved PARP in tetracycline-inducible A549 cells ectopically expressing mito-p53 FL, p53ψ and mito-p53 mutants upon induction with doxycycline for 3 days. Tubulin was used as a loading control. FIG. 12D shows a Western blot analysis of A549 cells ectopically expressing p53Ψ. Protein extracts were obtained from cells grown in the presence of doxycycline (0.5 μg/ml) for 5 days. p53Ψ-expressing cells have similar level of expression and subcellular localization of Cytochrome C (CYC). FIG. 12E shows that Tid-1 is required for p53-psi induced pro-metastatic features. In the left panel, the percentage of wound closure is presented at the indicated time. A549 cells ectopically expressing p53Ψ were induced with doxycycline for 3 days and then transfected with control (C) or tid-1-specific (T) siRNA. Standard wound healing experiments were performed 72 hours after transfection. In the right panel, a Western blot analysis is shown for protein extracts from A549 cells ectopically expressing p53Ψ following transfection with tid1-specific (T) or control (C) siRNA.

FIG. 13A-D shows that CypD is required for p53Ψ-induced EMT. FIG. 13A presents the relative mRNA expression of the indicated genes by real-time PCR of MCF7 cells ectopically expressing p53FL and p53Ψ upon treatment for 5 days with CsA [2 mM]. Treatment with CsA is sufficient to restore expression of E-cadherin to levels similar to parental cells, and conversely to reduce expression of EMT markers. Data shown represent relative expression compared to ectopic expression of a vector control (mean±SD, n=6; p<0.0001, Student's t-test). FIG. 13B shows a Western blot analysis of A549 cells expressing p53Ψ or an empty vector that were subsequently transfected with CypD siRNA. Cells were also treated with 10 mM NAC for 5 days. The cell extracts were probed for E-cadherin, p53, CypD, and as a control GAPDH. FIG. 13C shows a Western blot analysis of A549 cells ectopically expressing p53Ψ in the presence and absence of ROS scavengers. Cells were treated with 10 mM NAC or 500 μM Tempol for 5 days, then extracts were probed for E-cadherin, p53 and GAPDH as indicated. FIG. 13D shows that NAC treatment is sufficient to decrease the invasion capabilities of A549 cells ectopically expressing p53Ψ. Cells were grown in the presence or absence of NAC (10 mM). After 5 days, the invasive potential of cells was determined using a standard Matrigel invasion assay. Filter chambers were coated with 40 μl Matrigel and invasion was assessed after 30 hours.

Figure 14:
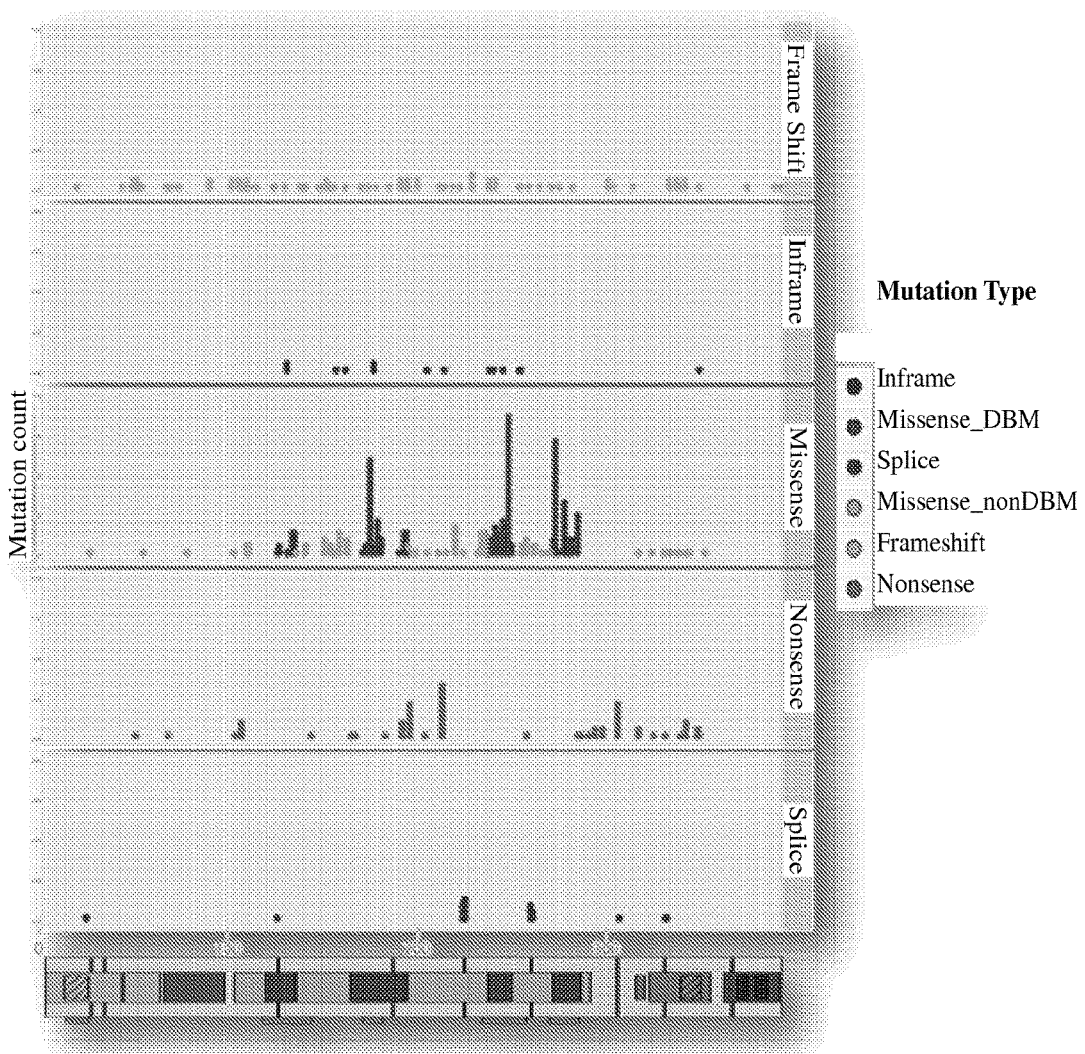

FIG. 14 shows the distribution of the indicated mutation types in breast cancer.

Figure 15:
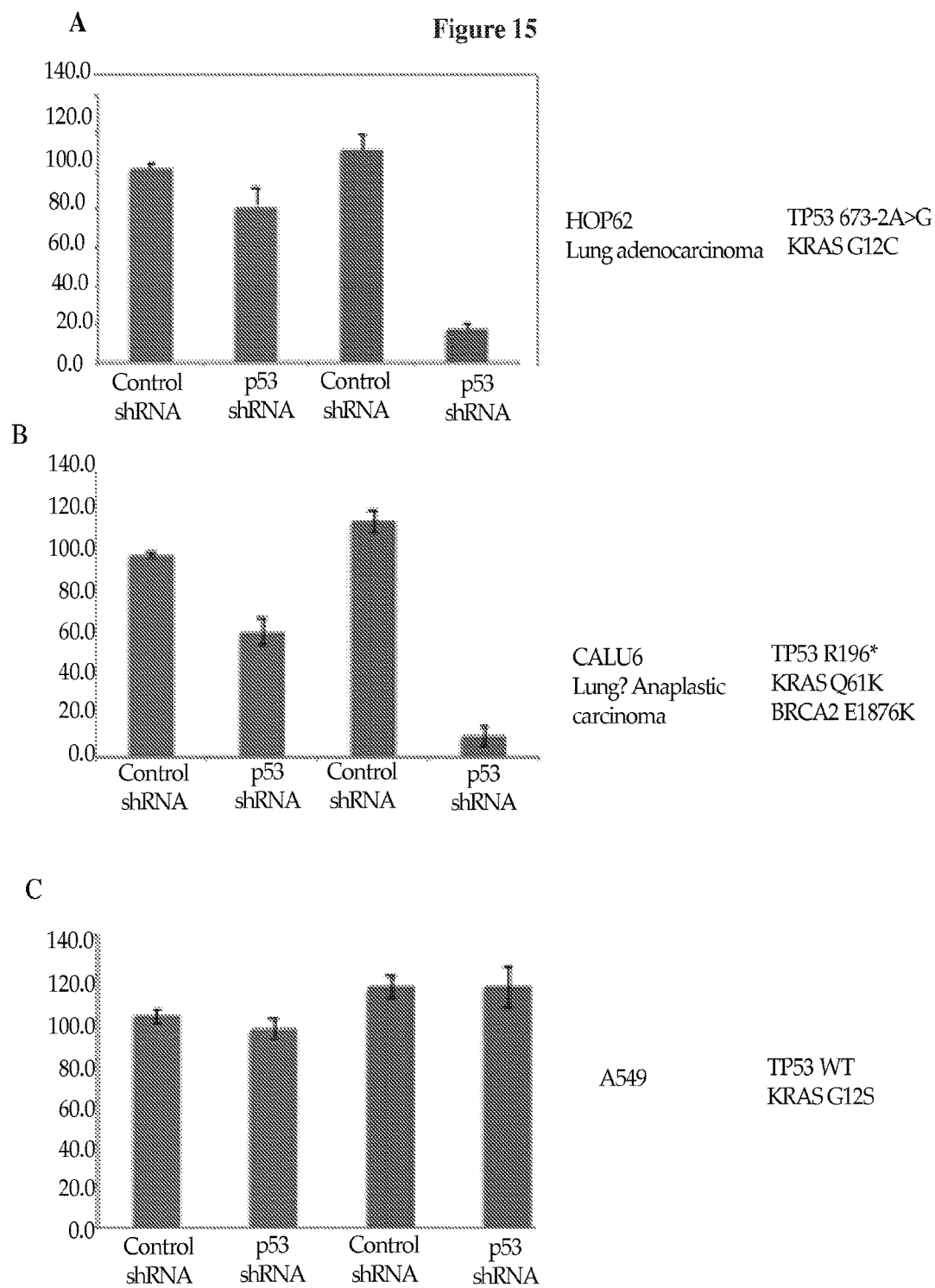

FIG. 15A-C shows that p53 is required for cell survival. FIG. 15A shows the percent cell survival following shRNA knockdown of p53 in HOP62 cells expressing p53FL or p53Ψ. FIG. 15B shows the percent cell survival following shRNA knockdown of p53 in CALU6 cells expressing p53FL or p53Ψ. FIG. 15C shows the percent cell survival following shRNA knockdown of p53 in A549 cells expressing p53FL.

FIG. 16A-H shows relative gene expression in A549 cells expressing GFP or p53Ψ. FIG. 16A shows expression of ANG. FIG. 16B shows expression of CYR61. FIG. 16C shows expression of CTGF. FIG. 16D shows expression of TNF-α. FIG. 16E shows expression of Endo. FIG. 16F shows expression of TGFβ2. FIG. 16G shows expression of thrombospondin. FIG. 16H shows expression of FGF2.

Figure 17:
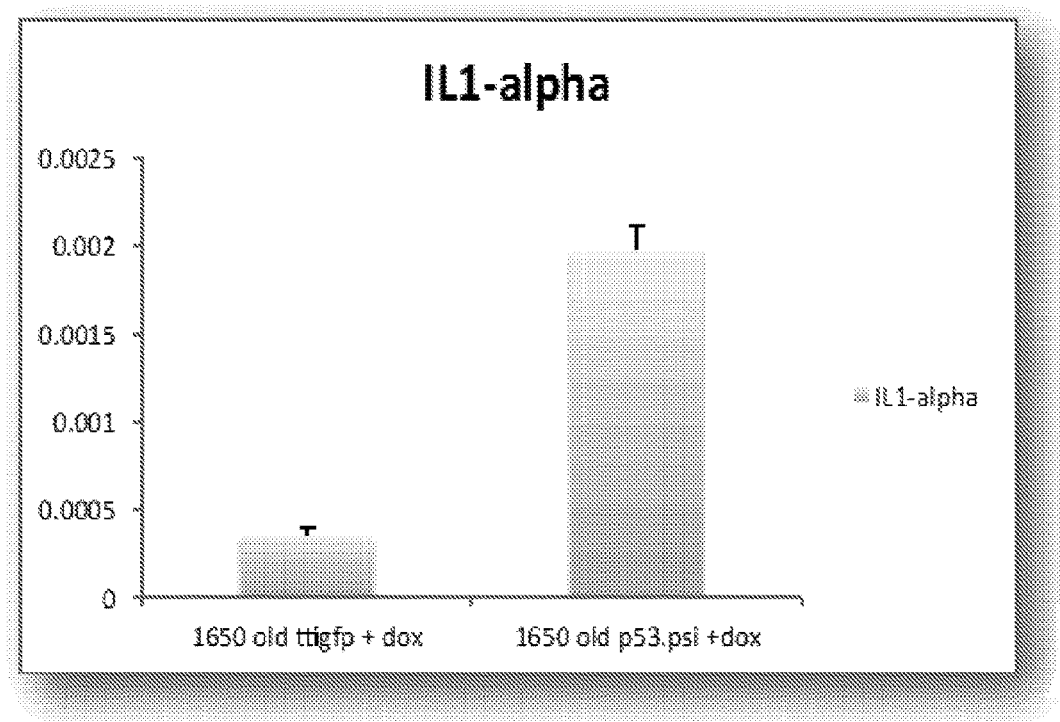

FIG. 17 shows relative expression of IL-1α in A549 cells expressing GFP or p53Ψ.

Figure 18:
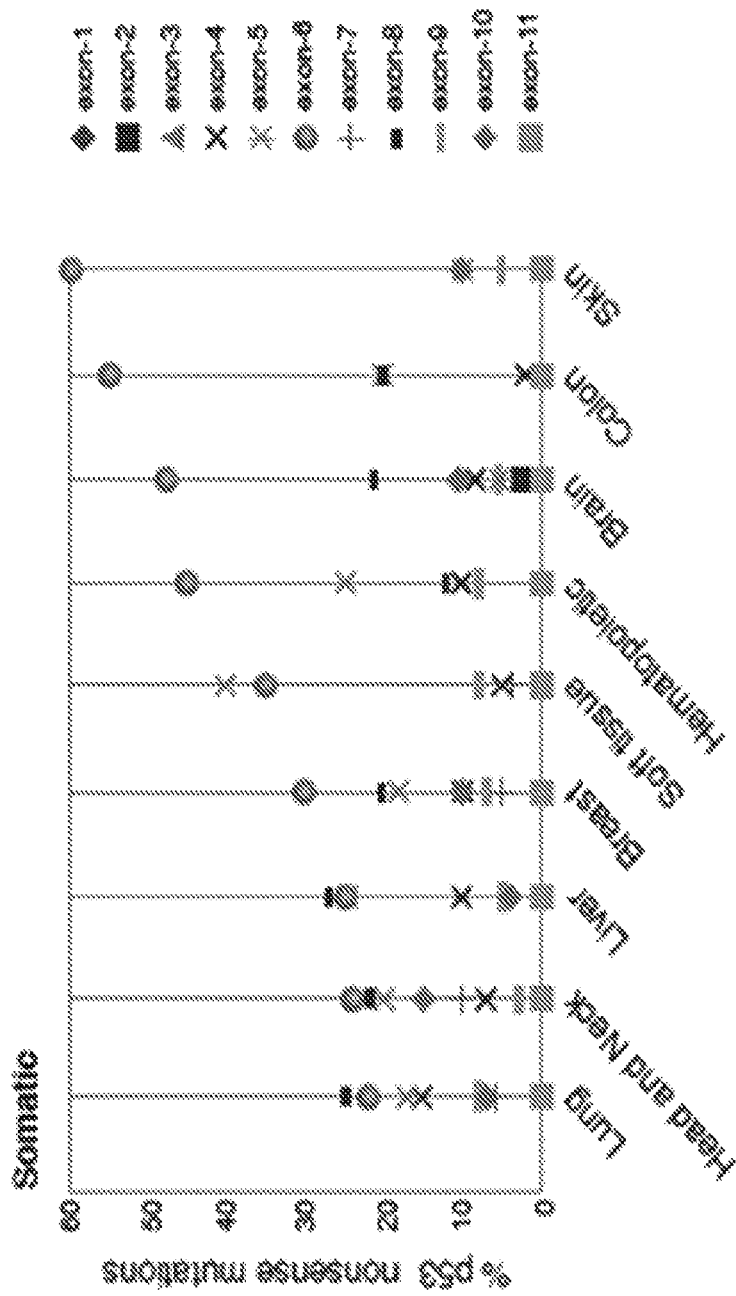

FIG. 18 is a chart that represents the distribution of TP53 non sense mutations in tumors (N=28,717). Each line in the chart indicates the percentage of a particular TP53 nonsense relative to all other TP53 nonsense mutations. P53 codons are labeled when the frequency of nonsense mutations at this position is higher than 2%. Exon-6 nonsense mutations are indicated in orange. In addition to these tumors, p53 mutations that lead to the generation of a p53-psi like isoform are present in melanoma, bladder cancer, prostate, ovarian and pancreatic cancers, osteosarcoma, esophagus, small intestine, stomach, thyroid, urinary tract, uterus, peritoneum, male and female genital organs.

DETAILED DESCRIPTION OF INVENTION

Described herein are p53 splice variants, referred to as p53Ψ, and additional p53Ψ variants that produce p53Ψ-like proteins that have a role in the development and/or progression of cancer. As demonstrated herein, p53Ψ increases the mitochondrial pore permeability of cells and increases production of reactive oxygen species (ROS) through an interaction with cyclophilin D (CypD). This results in promotion of epithelial to mesenchymal transition (EMT) of the cells. Disclosed herein are methods of inhibiting cancer cells or the growth of cancer cells that express one or more cell biomarkers of the mesenchymal state by administering a CypD inhibitor. Also described are methods of reverting the state of cancer cells that express one or more biomarkers of the mesenchymal state by administering a CypD inhibitor. Also provided are methods of inhibiting an epithelial to mesenchymal transition (EMT) of a cell by contacting the cell with a CypD inhibitor. Also provided are methods of treating cells that express p53Ψ by contacting the cells with a CypD inhibitor. Also provided are methods of identifying cells that will undergo EMT by detecting expression of p53Ψ. Inhibitors of p53Ψ and/or inhibitors of ROS may also be used in the methods. Further, the present disclosure provides methods of predicting that an individual will develop cancer or that an individual's cancer will relapse.

A "cell" refers to a single cell or to multiple cells (at least one, one or more cells). In some embodiments, the cell or cells are within a population of cells. In some embodiments, the cell is a cancer cell. The cell(s) can be in an individual or obtained from an individual.

P53

P53 is an evolutionarily conserved transcription factor that plays a central role in regulating many fundamental aspects of cellular stress responses, genome surveillance, angiogenesis, and suppression of oncogenic transformation [1]. In response to strong cellular stresses such as DNA damage, oxidative stress, osmotic shock, or oncogenic signals, p53 regulates the expression of a large number of genes that affect cell-cycle arrest, senescence, and apoptosis [1]. Under basal physiological conditions, p53 has additional roles in the cell, including regulation of development, reproduction, metabolism, and self-renewal capacity [2],[3], [4], [5]. The factors that influence the diversity and duration of p53 responses are poorly understood.

Figure 3:
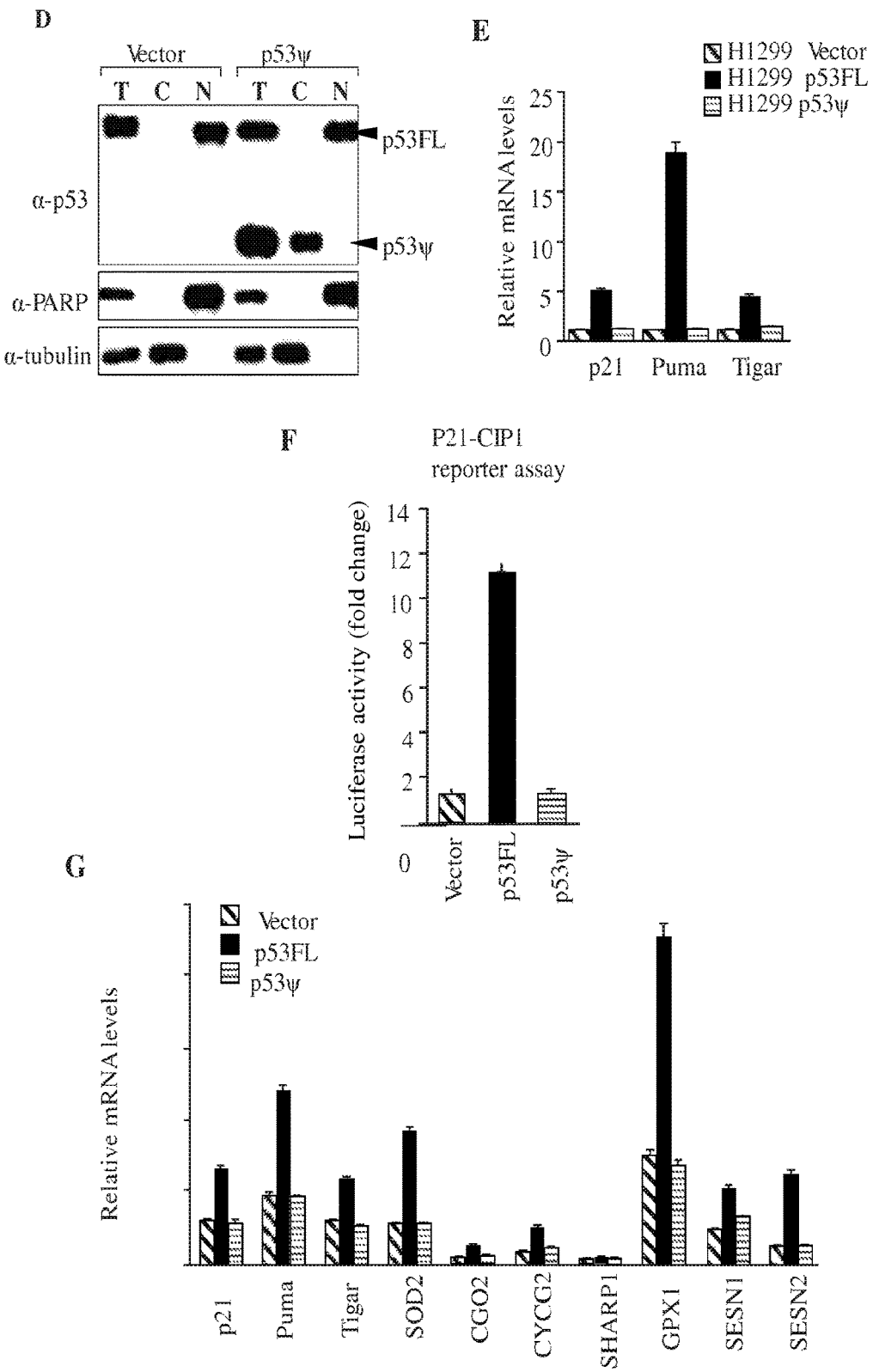
FIG. 3A-G shows that p53Ψ is devoid of transcriptional activity.

The term "p53FL" refers to full length p53 protein. In humans, p53FL is encoded by the gene TP53 on chromosome 7 and comprises 11 exons. Orthologs of human p53FL can be found in most mammals. p53FL contains an N-terminal transactivation domain that is involved in regulating downstream target genes, such as PUMA, TIGAR, p21, SOD2, SGO2, CYCG2, SHARP1, GPX1, SENS1, AND SENS2. P53FL also contains a central DNA binding domain that mediates the transcriptional regulation functions of p53FL, several nuclear localization sequences, and a C-terminal oligomerization domain that promotes dimerization of p53FL (FIG. 3A). Upon activation, for example by an oncogenic signal, p53FL is phosphorylated, resulting in increased stability and half-life of the protein. Activated p53FL accumulates in the cell, and undergoes a conformational change that allows the protein to regulate transcription (activation and inhibition) of a large number of genes (e.g., PUMA, TIGAR, p21, SOD2, SGO2, CYCG2, SHARP1, GPX1, SENS1, AND SENS2).

Under basal physiological conditions, p53FL resides in the nucleus of the cell; in conditions of cellular stress or apoptotic stimuli, p53FL localizes to the mitochondria with the help of chaperone protein Tid1. There, p53FL modulates the activity of factors including Bcl-XL, Bcl-2, BAK, BAX, and regulates the integrity of the mitochondrial membrane. In the mitochondrial matrix, p53FL interacts with MnSOD, the primary antioxidant enzyme, and cyclophilin D (CypD), a mitochondrial matrix peptidyl-prolyl isomerase that modulates opening of the mitochondrial permeability transition pore (mPTP). In normal, healthy cells, the mPTP remains closed, but under conditions in which p53FL is activated, the mPTP is induced to open.

Described herein is a novel mode of p53 regulation that involves alternative splicing of the TP53 gene. Use of the alternative 3' splice site in intron 6 of TP53 results in production of a p53 isoform referred to as p53Ψ (the protein product of this alternative splicing event). Splicing of p53 to produce p53FL requires a conserved "AG" intronic dinucleotide at the boundary of intron 6 and exon 7. Many mutations or alterations may result in production of p53Ψ or a p53Ψ-like truncated variant of p53. As used herein, "p53Ψ" refers to p53Ψ or any p53Ψ-like isoform that results from alternative splicing or mutation in intron 6 of the TP53 gene For example, an alteration of the "AG" dinucleotide such that the guanosine nucleotide at position −1 relative to the splice junction (e.g., position c.673−1G) is a cytosine, thymine, or adenine, favors the use of the alternative splice acceptor site in intron 6 and generates p53Ψ. Similarly, alteration of the adenine at position −2 relative to the splice junction (e.g., position c.673−2A) to a cytosine, thymine, or guanosine, favors the alternative splice acceptor site and generates p53Ψ. Similarly, alteration of the guanosine at position +1 relative to the splice junction (e.g., position c.672+1G) to a cytosine, thymine, or adenine, favors the alternative splice acceptor site and generates p53Ψ. Alteration of the thymine at position +2 relative to the splice junction (e.g., position c.672+2T) to a cytosine, guanosine, or adenine, favors the alternative splice acceptor site and generates p53Ψ. Alteration of the guanosine at position −1 relative to the splice junction (e.g., position c.672−1G) to a cytosine, thymine, or adenine, favors the alternative splice acceptor site and generates p53Ψ. Alteration of the adenine at position −2 relative to the splice junction (e.g., position c.672−2A) to a cytosine, thymine, or guanosine, also favors the alternative splice acceptor site and generates p53Ψ. Other mutations, for example any alteration in intron 6 or alterations that result in a premature stop codon in the protein coding sequence in exon 6, may result in production of a p53Ψ truncated variant of p53. Example sites for nucleotide mutation or alteration that may result in production of a p53Ψ truncated variant of p53 are shown in FIG. 14. Additional examples of nonsense mutations that may result in production of p53Ψ include, without limitation, mutations at the nucleotide position selected from the group consisting of c.574, c.585_586, c.586, c.591_592, c.592, c.602, c.609_610, c.610, c.615, c.617, c.625, c.637, c.660, c.658_659, c.660, c.661, and c.670 of the TP53 gene. In some embodiments, the mutation at nucleotide position c.574 is a mutation of a cytosine (e.g., position c.574C) to a thymine. In some embodiments, the mutation at nucleotide position c.585_586 is a mutation of two cytosine nucleotides (e.g., position c.585_586CC) to two thymine nucleotides. In some embodiments, the mutation at nucleotide position c.586 is a mutation of a cytosine (e.g., position c.586C) to a thymine. In some embodiments, the mutation at nucleotide position c.591_592 is a mutation of two guanosine nucleotides (e.g., position c.591_592GG) to two thymine nucleotides. In some embodiments, the mutation at nucleotide position c.592 is a mutation of a guanosine (e.g., position c.592G) to a thymine. In some embodiments, the mutation at nucleotide position c.602 is a mutation of a thymine (e.g., position c.602T) to an adenine. In some embodiments, the mutation at nucleotide position c.609_610 is a mutation of two guanosine nucleotides (e.g., position c.609_610) to two thymine nucleotides. In some embodiments, the mutation at nucleotide position c.610 is a mutation of a guanosine (e.g., position c.610G) to a thymine. In some embodiments, the mutation at nucleotide position c.615 is a mutation of a thymine (e.g., position c.615T) to an adenine. In some embodiments, the mutation at nucleotide position c.617 is a mutation of a thymine (e.g., position c.617T) to an adenine. In some embodiments, the mutation at nucleotide position c.625 is a mutation of an adenine (e.g., position c.625A) to a thymine. In some embodiments, the mutation at nucleotide position c.637 is a mutation of a cytosine (e.g., position c.637C) to a thymine. In some embodiments, the mutation at nucleotide position c.660 is a mutation of a thymine (e.g., position c.660T) to a guanosine or an adenine. In some embodiments, the mutation at nucleotide position c.658_659 is an insertion mutation (e.g., position c.658_659). In some embodiments, the mutation at nucleotide position c.661 is a mutation of a guanosine (e.g., position c.661G) to a thymine. In some embodiments, the mutation at nucleotide position c.670 is a mutation of a guanosine (e.g., position c.670) to a thymine.

Unlike p53FL, p53Ψ, including p53Ψ-like proteins, lacks portions of the DNA-binding domain, the nuclear-localization sequence, and the oligomerization domain (FIG. 3A). As encompassed by the term "p53Ψ," p53Ψ-like proteins, like p53Ψ, are truncated and lack at least a portion of the DNA binding domain of the p53 sequence, as well as the nuclear-localization sequence and oligomerization domain. Because it lacks portions of the DNA-binding domain, p53Ψ is incapable of sequence-specific DNA binding and does not transcriptionally regulate p53 target genes (e.g., PUMA, TIGAR, p21, SOD2, SGO2, CYCG2, SHARP1, GPX1, SENS1, AND SENS2). In contrast to p53FL, p53Ψ is localized to the mitochondria and through its interaction with CypD, constitutively increases production of reactive oxygen species (ROS) and increases mPTP permeability.

Aspects of the disclosure relate to the recognition that p53Ψ regulates EMT of a cell, as well as regulates the growth of a cell (e.g., proliferation, survival). As described herein, cells that express p53Ψ exhibit different characteristics compared to cells that express p53FL. For example, cells that express p53Ψ may exhibit one or more characteristics, including increased motility, invasive capacity, resistance to chemotherapeutic agents, mPTP permeability, ROS production, increased accumulation of de novo mutations and altered gene expression. In some embodiments, cells that express p53Ψ have characteristics of mesenchymal cells. Any of the foregoing characteristics may be assessed by methods known in the art or provided herein.

The nucleotide sequence of p53FL is provided by SEQ ID NO: 1.
ATGGAGGAGCCGCAGTCAGATCCTAGCGTCGAGCCCCCTCTGAGTCAGGA

AACATTTTCAGACCTATGGAAACTACTTCCTGAAAACAACGTTCTGTCCC

CCTTGCCGTCCCAAGCAATGGATGATTTGATGCTGTCCCCGGACGATATT

GAACAATGGTTCACTGAAGACCCAGGTCCAGATGAAGCTCCCAGAATGCC

AGAGGCTGCTCCCCCCGTGGCCCCTGCACCAGCAGCTCCTACACCGGCGG

CCCCTGCACCAGCCCCTCCTGGCCCCTGTCATCTTCTGTCCCTTCCCAG

AAAACCTACCAGGGCAGCTACGGTTTCCGTCTGGGCTTCTTGCATTCTGG

GACAGCCAAGTCTGTGACTTGCACGTACTCCCCTGCCCTCAACAAGATGT

TTTGCCAACTGGCCAAGACCTGCCCTGTGCAGCTGTGGGTTGATTCCACA

CCCCCGCCCGGCACCCGCGTCCGCGCCATGGCCATCTACAAGCAGTCACA

GCACATGACGGAGGTTGTGAGGCGCTGCCCCCACCATGAGCGCTGCTCAG

ATAGCGATGGTCTGGCCCCTCCTCAGCATCTTATCCGAGTGGAAGGAAAT

TTGCGTGTGGAGTATTTGGATGACAGAAACACTTTTCGACATAGTGTGGT

GGTGCCCTATGAGCCGCCTGAGGTTGGCTCTGACTGTACCACCATCCACT

ACAACTACATGTGTAACAGTTCCTGCATGGGCGGCATGAACCGGAGGCCC

ATCCTCACCATCATCACACTGGAAGACTCCAGTGGTAATCTACTGGGACG

GAACAGCTTTGAGGTGCGTGTTTGTGCCTGTCCTGGGAGAGACCGGCGCA

CAGAGGAAGAGAATCTCCGCAAGAAGGGGAGCCTCACCACGAGCTGCCC

CCAGGGAGCACTAAGCGAGCACTGCCCAACAACACCAGCTCCTCTCCCCA

GCCAAAGAAGAAACCACTGGATGGAGAATATTTCACCCTTCAGATCCGTG

GGCGTGAGCGCTTCGAGATGTTCCGAGAGCTGAATGAGGCCTTGGAACTC

AAGGATGCCCAGGCTGGGAAGGAGCCAGGGGGGAGCAGGGCTCACTCCAG

CCACCTGAAGTCCAAAAAGGGTCAGTCTACCTCCCGCCATAAAAAACTCA

TGTTCAAGACAGAAGGGCCTGACTCAGACTGA

The amino acid sequence of p53FL is provided by SEQ ID NO: 2.
MEEPQSDPSVEPPLSQETFSDLWKLLPENNVLSPLPSQAMDDLMLSPDDI

EQWFTEDPGPDEAPRMPEAAPPVAPAPAAPTPAAPAPAPSWPLSSSVPSQ

KTYQGSYGFRLGFLHSGTAKSVTCTYSPALNKMFCQLAKTCPVQLWVDST

PPPGTRVRAMAIYKQSQHMTEVVRRCPHHERCSDSDGLAPPQHLIRVEGN

LRVEYLDDRNTFRHSVVVPYEPPEVGSDCTTIHYNYMCNSSCMGGMNRRP

ILTIITLEDSSGNLLGRNSFEVRVCACPGRDRRTEEENLRKKGEPHHELP

-continued
PGSTKRALPNNTSSSPQPKKKPLDGEYFTLQIRGRERFEMFRELNEALEL

KDAQAGKEPGGSRAHSSHLKSKKGQSTSRHKKLMFKTEGPDSD

The nucleotide sequence of p53Ψ is provided by SEQ ID NO: 3.
ATGGAGGAGCCGCAGTCAGATCCTAGCGTCGAGCCCCCTCTGAGTCAGGA

AACATTTTCAGACCTATGGAAACTACTTCCTGAAAACAACGTTCTGTCCC

CCTTGCCGTCCCAAGCAATGGATGATTTGATGCTGTCCCCGGACGATATT

GAACAATGGTTCACTGAAGACCCAGGTCCAGATGAAGCTCCCAGAATGCC

AGAGGCTGCTCCCCCCGTGGCCCCTGCACCAGCAGCTCCTACACCGGCGG

CCCCTGCACCAGCCCCTCCTGGCCCCTGTCATCTTCTGTCCCTTCCCAG

AAAACCTACCAGGGCAGCTACGGTTTCCGTCTGGGCTTCTTGCATTCTGG

GACAGCCAAGTCTGTGACTTGCACGTACTCCCCTGCCCTCAACAAGATGT

TTTGCCAACTGGCCAAGACCTGCCCTGTGCAGCTGTGGGTTGATTCCACA

CCCCCGCCCGGCACCCGCGTCCGCGCCATGGCCATCTACAAGCAGTCACA

GCACATGACGGAGGTTGTGAGGCGCTGCCCCCACCATGAGCGCTGCTCAG

ATAGCGATGGTCTGGCCCCTCCTCAGCATCTTATCCGAGTGGAAGGAAAT

TTGCGTGTGGAGTATTTGGATGACAGAAACACTTTTCGACATAGTGTGGT

GGTGCCCTATGAGCCGCCTGAGGTCTCCCCAAGGCGCACTGGCCTCATCT

TGGGCCTGTGTTATCTCCTGGGTTGGCTCTGA

The amino acid sequence of p53Ψ is provided by SEQ ID NO: 4.
MEEPQSDPSVEPPLSQETFSDLWKLLPENNVLSPLPSQAMDDLMLSPDDI

EQWFTEDPGPDEAPRMPEAAPPVAPAPAAPTPAAPAPAPSWPLSSSVPSQ

KTYQGSYGFRLGFLHSGTAKSVTCTYSPALNKMFCQLAKTCPVQLWVDST

PPPGTRVRAMAIYKQSQHMTEVVRRCPHHERCSDSDGLAPPQHLIRVEGN

LRVEYLDDRNTFRHSVVVPYEPPEVSPRRTGLILGLCYLLGWL

One embodiment described here is a method of determining whether a cell, referred to as a cell to be assessed or a test cell, expresses p53Ψ. Determining whether a cell expresses p53Ψ can be assessed by a variety of methods, including, but not limited to, DNA sequencing; reverse transcription followed by sequencing to attain the sequence of the spliced mRNA; detection of p53Ψ RNA by any method such as fluorescence in situ hybridization; detection of p53Ψ protein with an antibody, compound, small molecule, or other ligand able to bind p53Ψ; localization of p53Ψ in the cell, such as by fluorescent microscopy or presence of the protein in a fractionated portion of a cell; or expression level of specific genes, such as decreased expression of p53 regulated genes (e.g. CDKN1A, Triap1, Sens1, Sens2, Pgam1, Pgam2, Sco1, Sco2, Tigar, Puma, p21 Gpx1, and CD44). In some embodiments, the cell in which p53 is detected is in an individual. In some embodiments, the presence of p53Ψ indicates that a cell is a cancer cell or is predicted (likely) to become a cancer cell. In some embodiments, the presence of p53Ψ identifies a cell that will undergo EMT. In some embodiments, the presence of p53Ψ identifies an individual suffering from cancer as a candidate for treatment. In some embodiments, the presence of p53Ψ predicts whether an individual will develop cancer. In some embodiments, the presence of p53Ψ indicates that (predicts whether) an individual with cancer will relapse.

In some embodiments, the presence of p53Ψ is determined by detecting a mutation (an alteration in the nucleic acid present) at position c.673−2A (e.g., c.673-2A>T). In some embodiments, the mutation at position c.673−2A is a substitution of an adenine with a guanosine, a cytosine, or a thymine. In some embodiments, the presence of p53Ψ is determined by detection of a mutation at position c.673−1G. In some embodiments, the mutation at position c.673−1G is a substitution of a guanosine with an adenine, a cytosine, or a thymine. In some embodiments, the presence of p53Ψ is determined by detection of a mutation at position c.672+1G. In some embodiments, the mutation at position c.672+1G is a substitution of a guanosine with an adenine, a cytosine, or a thymine. In some embodiments, the presence of p53Ψ is determined by detection of a mutation at position c.672+2T. In some embodiments, the mutation at position c.672+2T is a substitution of a thymine with an adenine, a cytosine, or a guanosine. In some embodiments, the presence of p53Ψ is determined by detection of a mutation at position c.673−2A. In some embodiments, the mutation at position c.673−2A is a substitution of an adenine with a guanosine, a cytosine, or a thymine. In other embodiments, the presence of p53 is determined by detection of a nonsense mutation in the nucleotide sequence that encodes the DNA binding domain, as described herein.

In some embodiments, a characteristic or property of a cell to be assessed is compared to characteristics or properties of a cell that expresses p53FL (to a control cell, such as a cell, of the same type as that being assessed, that expresses p53FL and does not express p53Ψ) to determine whether p53Ψ is expressed in the test cell, as p53Ψ is generated at the expense of p53FL. For example, the expression level of p53-regulated gene(s) in a test cell may be compared with the expression level(s) of the same p53-regulated gene(s) in an appropriate control (e.g., the same type of cell as the cell being assessed that expresses p53FL. For example, decreased expression in the test cell of one or more genes activated by p53 (relative to expression of the same p53-regulated gene(s) in the same cell type that expresses p53FL) is indicative of the expression of p53Ψ. Examples of p53-regulated genes include, but are not limited to, CDKN1A, Triap1, Sens1, Sens2, Pgam1, Pgam2, Sco1, Sco2, Tigar, Puma, p21 Gpx1, and CD44. Furthermore, p53Ψ regulated genes can also be assessed; examples of which include, without limitation, CCL2, IL-1β, IL-1α, and IL1Rα.

The present disclosure also provides methods in which cells are contacted with a (at least one, one or more) CypD inhibitor. In some embodiments, the cell is contacted with more than one CypD inhibitor. In some embodiments, a CypD inhibitor reduces production of CypD, reduces the activity of CypD, or disrupts or inhibits interaction with p53Ψ, resulting in closure of the mPTP. In some embodiments, the CypD inhibitor is a pharmacologic inhibitor of CypD. In some embodiments, the CypD inhibitor is an RNA interference (RNAi) molecule that targets CypD mRNA. Examples of pharmacologic inhibitors of cyclophilin include, but are not limited to, cyclosporine, cyclosporine A (CsA), SYC-635, SYC-465, SYC-641, NIM811, Debio 025 (Alisporivir), sanglifehrin A, and derivatives of any of the foregoing molecules. Additional examples of pharmacologic inhibitors of cyclophilin are provided in PCT Publication No WO 2012/097123 A2, WO 1998/025950 A, WO 2011/076784 A2, and WO 2012/103520 A1.

The present disclosure also provides methods in which cells are contacted with a (at least one, one or more) p53Ψ inhibitor. Cells may be contacted with a p53Ψ inhibitor, alone or in combination with a CypD inhibitor or a ROS inhibitor or in combination with both a CypD inhibitor and a ROS inhibitor. In some embodiments, the p53Ψ inhibitor reduces (partially or completely) expression or activity of p53Ψ. In some embodiments, the p53Ψ inhibitor is a pharmacologic inhibitor of p53Ψ. In some embodiments, the p53Ψ inhibitor is an RNA interference (RNAi) molecule that targets p53Ψ mRNA (e.g., is complementary to all or a portion of p53Ψ mRNA. In some embodiments, the p53Ψ inhibitor reduces mitochondrial permeability. In some embodiments, the p53Ψ inhibitor inhibits interaction of p53Ψ with CypD. In some embodiments, the p53Ψ inhibitor reduces production of ROS.

As used herein, the term "ROS inhibitor" refers to any molecule that reduces (partially or completely) production of ROS or neutralizes (all or some of) ROS activity (e.g. a ROS scavenger). Examples of ROS inhibitors that may result in decreased production of ROS include RNA interference (RNAi) molecules that target and reduce expression of an enzyme that produces a ROS, such as superoxide, hydrogen peroxide, hydroxyl radical, or hydroxyl ion. The present disclosure also provides methods in which cells are contacted with a (at least one, one or more) ROS inhibitor. In some embodiments, cells are contacted with more than one ROS inhibitor. Examples of enzymes that may be expressed in a cell to reduce or neutralize ROS in a cell include, but are not limited to, alpha-1-microglobulin, superoxide dismutase, catalase, lactoperoxidases, glutathione peroxidases and peroxiredoxins. Small molecules, referred to as ROS scavengers, that may be contacted with a cell to reduce or neutralize ROS include, but are not limited to, ascorbic acid (vitamin C), tocopherol (vitamin E), uric acid, glutathione, polyphenol antioxidants, N-acetyl cysteine, Tempol, sodium pyruvate, mannitol, carboxyl-PTIO, Ebselen, sodium azide, MnTBAP, Tiron, Edaravone, catalase, polyethylene glycol-superoxide dismutase (PEG-SOD), manganese (III) tetrakis(1-methyl-4-pyridyl)porphyrin (MnT-MPyP), 6-hydroxy-2,5,7,8-tetramethylchroman-2-carboxylic acid (Trolox), deferoxamine, and U-74389G. Additional examples of ROS scavengers are provided in U.S. Pat. Nos. 6,900,338 B1 and 8,487,079 B2.

In some embodiments, contacting a cell with a p53Ψ inhibitor or a CypD inhibitor results in decreased mPTP permeability. The mPTP permeability can be assessed by any method known in the art, for example, a calcein AM assay.

In some embodiments, contacting a cell with a p53Ψ inhibitor or a ROS inhibitor results in decreased ROS in the cell. The amount of ROS in a cell can be assessed by, for example, using a MitoSOX reagent.

Epithelial to Mesenchymal Transition

As used herein, "epithelial to mesenchymal transition" or "EMT" refers to transformation of a cell that has one or more characteristics of an epithelial cell to a cell that has one or more characteristics of a mesenchymal cell. Described are methods of inhibiting epithelial to mesenchymal transition (EMT) of a cell. Cells that have undergone EMT display properties of a mesenchymal cell, such as increased migratory and invasive ability (e.g., pro-metastatic properties), self-renewal capacity, tumorigenicity, increased resistance to chemotherapeutic agents, increased expression of cell markers (e.g. cell biomarkers) associated with the mesenchymal state, and decreased expression of cell markers (e.g. cell biomarkers) associated with the epithelial state. In many cases, individuals with cells displaying properties of mesenchymal cells have a poor prognosis, including a decrease in disease-free survival and/or a decrease in overall survival. Therefore, it may be advantageous to inhibit EMT of a cell by the methods described. In some embodiments, contacting a cell that is undergoing or has undergone EMT results in reversion of the cell to an epithelial state or epithelial-like state. The state of a cell (whether it is epithelial or mesenchymal) can be assessed by any method known in the art or described herein.

The term a "mesenchymal-like" state refers to a state of a cell that is characterized by at least one cell marker (e.g. cell biomarker) or characteristic associated with the mesenchymal state. The term an "epithelial-like" state refers to a state of a cell that is characterized by at least one cell marker (e.g. cell biomarker) or characteristic associated with the epithelial cell. In some embodiments, the state of a cell may be compared to the state of another cell. In some embodiments, a cell may be described as mesenchymal-like or having a mesenchymal-like state as compared to another cell that has fewer cell markers or characteristics of mesenchymal cells. In other embodiments, a cell may be described as epithelial-like or having an epithelial-like state as compared to another cell that has fewer cell markers or characteristics of epithelial cells. A "cell marker" or "cell biomarker" may be used interchangeably throughout the present disclosure. Both terms refer to a molecule (e.g., a protein) that can serve as an indicator of the cell state and/or the cell type. In some embodiments, the cell biomarker is a protein expressed on the surface of a cell that can be detected by any method known in the art or described herein.

Examples of characteristics of epithelial cells or epithelial-like cells include, but are not limited to, increased expression of one or more cell biomarkers associated with the epithelial state, such as E-cadherin, CD24, CD104, MUC-1, MUC-4, MUC16, A33, CD143, CD166, PD-L1, B7-H2, B7-H3, Nectin-1, Nectin-2, Nectin-3, Nectin-4, cytokeratin, ZO-1, Laminin-1, Entactin, collagen, one or more miR200 family microRNA, or mir-335; phenotypic properties of an epithelial cell, such as cellular morphology; sensitivity to chemotherapeutic agents; and any additional functional property as described herein. Epithelial cells or epithelial-like cells are also characterized by decreased expression of one or more proteins associated with the mesenchymal state, such as CD44, CD45, N-cadherin, Fibronectin, Snail, Slug, Twist, Zeb1, CD44, and Vimentin, or a reduction in any phenotype, morphology or functional property associated with mesenchymal cells. Any characteristic of the cell, including expression of a cell biomarker, may be evaluated prior to, during or after administration of an inhibitor described herein.

Examples of characteristics of mesenchymal cells or mesenchymal-like cells include, without limitation, increased expression of one or more mesenchymal protein, such as CD44, CD45, N-cadherin, Fibronectin, Snail, Slug, Twist, Zeb1, CD44, and Vimentin; phenotypic properties of a mesenchymal cell, such as cellular morphology; resistance to chemotherapeutic agents, and any additional functional property as described herein. Mesenchymal cells or mesenchymal-like cells are also characterized by decreased expression of one or more proteins associated with the epithelial state, such as E-cadherin or CD24, or a reduction in any phenotype, morphology, of functional property associated with epithelial cells. In some embodiments, a cell, specifically a cell in the mesenchymal state, is characterized by high expression of CD44 ($CD44^{high}$) and low expression of CD24 ($CD24^{low}$)

Properties of cells may be assessed by methods known in the art. Cellular morphology can be evaluated by microscopy methods including, for example, bright field, confocal, electron, and fluorescence microscopy. The expression level of cell markers associated with the epithelial state or the mesenchymal state can be measured by methods including quantitative RT-PCR, flow cytometry, cell staining, antibody detection of cell markers, Western blotting, fluorescence microscopy and mass spectrometry. The migratory ability of cells can be assessed, for example, by a wound closure assay. The invasion and metastatic abilities of a cell can be evaluated, for example, by Matrigel invasion. Cells can be further evaluated for sensitivity to chemotherapeutic agents. Following exposure of the cell to a chemotherapeutic agent, its viability can be assessed by methods known in the art, including proliferation, metabolic activity, and live/dead staining.

Also described here are methods and compositions for inhibiting EMT of a cell. The present disclosure also provides methods and compositions for treating cancer characterized by $p53\Psi$ expression. In some embodiments, the methods provided herein comprise contacting cells with a CypD inhibitor. In some embodiments, the methods comprise contacting cells with an inhibitor of $p53\Psi$. In some embodiments, the methods comprise contacting cells with a ROS signaling inhibitor. In some embodiments, the methods comprise contacting cells with any combination of two, three or four of a (one or more) CypD inhibitor, a (one or more) inhibitor of $p53\Psi$, a (one or more) ROS Signaling inhibitor). In some embodiments, cells are contacted with a combination of a CypD inhibitor and a ROS inhibitor. In some embodiments, the methods comprise contacting cells with a combination of a CypD inhibitor and a $p53\Psi$ inhibitor. In some embodiments, the methods comprise contacting cells with a combination of a CypD inhibitor, a ROS inhibitor and a $p53\Psi$ inhibitor or with a combination of a CypD inhibitor, a ROS inhibitor, a $p53\Psi$ inhibitor and a ROS signaling inhibitor. The state of cells can be evaluated before, during or after they are contacted with one or more inhibitor.

In some embodiments, methods are provided for reverting the state of a cancer cell that expresses one or more cell markers of the mesenchymal state. As used herein, "reverting" a cell refers altering or redirecting a developmental pathway of the cell. In some embodiments, a cell that is undergoing an EMT or has undergone an EMT is reverted to become epithelial cell-like. In some embodiments, reverting a cell refers to halting the EMT of the cell. In some embodiments, methods of reverting a cell involve contacting the cell with a CypD inhibitor. In some embodiments, the methods involve contacting the cell with an inhibitor of $p53\Psi$. In some embodiments, the methods comprise contacting cells with a ROS signaling inhibitor. In some embodiments, the methods involve contacting the cell with any combination of two, three or four of a (one or more) CypD inhibitor, a (one or more) inhibitor of $p53\Psi$, a (one or more) ROS inhibitor and a (one or more) ROS signaling inhibitor. In some embodiments, cells are contacted with the combination of a CypD inhibitor and a ROS inhibitor. In some embodiments, the methods involve contacting the cell with a combination of a CypD inhibitor and a $p53\Psi$ inhibitor. In some embodiments, the methods involve contacting the cell with a combination of a CypD inhibitor, a ROS inhibitor and a $p53\Psi$ inhibitor or with a combination of a CypD inhibitor, a ROS inhibitor, a $p53\Psi$ inhibitor and a ROS signaling inhibitor. The state of the cell (e.g., mesenchymal-like, epithelial-like) can be evaluated before, during or after contacting the cell with any of the molecules or compositions provided herein. Moreover, any of the properties of the cell may be evaluated to determine the extent to which the cell has transitioned from an epithelial cell to a mesenchymal cell, or transitioned from a mesenchymal cell to an epithelial cell. In some embodiments, the state of the cell is evaluated relative to the state of another cell. In such embodiments, the cell may be more or less epithelial-like compared to another cell, or more or less mesenchymal-like compared to another cell.

Methods of Treatment

Methods of treating a cell, a cancer, or an individual are provided herein. In some aspects, methods are provided for treating a cell that expresses p53Ψ. In some embodiments, the cell comprises any one of the mutations described herein that results in the generation of p53Ψ. In some embodiments, the cell has a nonsense mutation in the TP53 gene that results in production of a p53Ψ-like protein. In some embodiments, the cell is contacted cell with a CypD inhibitor in an effective amount. In some embodiments, the cell is contacted cell with an inhibitor of p53Ψ in an effective amount. In some embodiments, the cell is contacted cell with a ROS signaling inhibitor in an effective amount. In some embodiments, the methods involve contacting the cell with the combination of a CypD inhibitor and a ROS inhibitor. In some embodiments, the methods involve contacting the cell with a combination of a CypD inhibitor and a p53Ψ inhibitor or a combination of a CypD inhibitor and a ROS signaling inhibitor. In some embodiments, the methods involve contacting the cell with any combination of three inhibitors, such as a CypD inhibitor, a ROS inhibitor and a p53Ψ inhibitor or with four inhibitors, such as at least a (one or more, at least one) CypD inhibitor; at least a (one or more, at least one) ROS inhibitor and a (one or more, at least one) ROS signaling inhibitor; and a (one or more, at least one) p53Ψ inhibitor. In those embodiments in which the cell is contacted with a combination of inhibitors, the inhibitors can be administered simultaneously or sequentially.

In other aspects, methods are provided for treating a cancer that is characterized by p53Ψ expression. Also provided are method for inhibiting, in an individual, EMT of cells that comprise a mutation that results in production of p53Ψ. In some embodiments, a CypD inhibitor is administered to the individual with cancer in an effective amount via a suitable route of administration. In some embodiments, the cell is contacted cell with an inhibitor of p53Ψ in an effective amount. In some embodiments, the methods involve administering to the individual with cancer the combination of a CypD inhibitor and a ROS inhibitor. In some embodiments, the methods involve administering to the individual with cancer a combination of a CypD inhibitor and a p53Ψ inhibitor. In some embodiments, the methods involve administering to the individual with cancer a combination of a CypD inhibitor, a ROS inhibitor and a p53Ψ inhibitor or with at least a (one or more, at least one) CypD inhibitor and a (one or more, at least one) ROS signaling inhibitor; at least a (one or more, at least one) ROS inhibitor and a (one or more, at least one) ROS signaling inhibitor; or at least a (one or more, at least one) ROS signaling inhibitor and a (one or more, at least one) p53Ψ inhibitor.

Some aspects of the disclosure provide methods for identifying a cell that will undergo an EMT. In some embodiments, method are provided for predicting whether a cell will become a cancer cell. In some embodiments, the methods provided predict whether a cell will become a mesenchymal cancer cell. The methods may involve determining whether the cell expresses p53Ψ. In some embodiments, the methods involve determining the state (e.g., epithelial or mesenchymal) of the cell.

In some embodiments, methods for identifying whether the individual is a candidate for a particular treatment, to monitor progression of the cancer, or to monitor effectiveness of the treatment. The methods may involve obtaining a sample of the cancer from the individual and determining if one or more cells of the cancer express p53Ψ. In some embodiments, the methods involve determining the state of a cell of the cancer (e.g., epithelial or mesenchymal). In some embodiments, the presence of p53Ψ or one or more characteristics of a mesenchymal cell indicates that the individual is a candidate for treatment. In some embodiments, the methods may involve obtaining a blood sample from the individual and determining whether one or more blood biomarkers of a cancer are present in the sample. A blood biomarker of a cancer may be the presence of circulating or cell-free DNA from a cancer cell. In some embodiments, circulating or cell-free DNA may be assessed for the presence of any one more mutations described herein, indicating the presence of p53Ψ. The presence and/or quantity of circulating or cf-DNA may be indicative of the efficacy of the treatment. Methods of quantifying and genotyping circulating or cf-DNA can be found, for example, in Newman et al. Nat. Med. (2014) 20(5):548-554; Diaz and Bardelli J. Clin. Oncol. (2014) 32(6): 579-586; and Maheswaran et al. N. Engl. J. Med. (2008) 369(4): 366-377.

In some embodiments, methods are provided for treating an individual having a cancer. In some embodiments, the cancer is evaluated for one or more markers of an epithelial cell and/or a mesenchymal cell. The cell may be evaluated prior to administration of a compound, during administration, or after administration. For example, the cell may be assessed to determine whether it expresses p53Ψ. Following administration of the compound, any one or more mesenchymal or epithelial property of the cell, as described herein, may be evaluated to determine whether the treatment was effective.

In some embodiments, methods for assessing an individual having a cancer or an individual previously having a cancer are provided. The methods may be used to identify whether the cancer may relapse. The methods may involve obtaining a sample from the individual and determining if one or more cells express p53Ψ. In some embodiments, the methods involve determining the epithelial or mesenchymal state of a cell. In some embodiments, the presence of p53Ψ indicates that the individual will relapse. In some embodiments, the methods involve obtaining a blood sample from the individual and determining whether one or more blood biomarkers of a cancer are present in the sample. A blood biomarker of a cancer may be the presence of circulating or cell-free DNA from a cancer cell. In some embodiments, circulating or cell-free DNA may be assessed for the presence of any one more mutations described herein, indicating the presence of p53Ψ. The presence and/or quantity of circulating or cf-DNA may be indicative of the cancer stage, prognosis, or likelihood of relapse. Methods of quantifying and genotyping circulating or cf-DNA can be found, for example, in Newman et al. Nat. Med. (2014) 20(5):548-554; Diaz and Bardelli J. Clin. Oncol. (2014) 32(6): 579-586; and Maheswaran et al. N. Engl. J. Med. (2008) 369(4): 366-377.

In some embodiments, methods for predicting that an individual will develop a cancer are provided. The methods may involve obtaining a sample from the individual and determining if one or more cells express p53Ψ. In some embodiments, the methods involve determining the epithelial or mesenchymal state of a cell. In some embodiments, the presence of p53Ψ or properties of a mesenchymal cell indicates the individual will develop cancer.

In some embodiments, methods for predicting that an individual will develop a cancer are provided. The methods may involve evaluating whether the individual consumed aristolochic acid. In some embodiments, the method involves obtaining a sample from the individual and determining if one or more cells express p53Ψ. In some embodiments, the methods involve determining the epithelial or mesenchymal state of a cell. In some embodiments, the method involves both evaluating whether the individual consumed aristolochic acid and obtaining a sample from the individual and determining if one or more cells express p53Ψ. In some embodiments, the consumption of aristolochic acid and the presence of p53Ψ indicates the individual will develop cancer.

As used herein, an individual may be a mammal, such as a human, and also including, but not limited to a dog, cat or horse. The human may be a child or an adult. In some embodiments the human is a geriatric individual. In some embodiments, if the compound is one that has been previously (prior to the instant disclosure) administered to individuals for purposes other than treating cancer, e.g., for treatment of a condition other than cancer, the individual is not one to whom the compound would normally be administered for such other purpose and/or the compound is administered in a formulation or at a dose distinct from that known in the art to be useful for such other purpose.

Moreover, as used herein treatment or treating includes amelioration, cure, and/or maintenance of a cure (the prevention or delay of relapse) of a disorder (e.g., a tumor). Treatment after a disorder has started aims to reduce, ameliorate or altogether eliminate the disorder, and/or its associated symptoms, to prevent it from becoming worse, to slow the rate of progression, or to prevent the disorder from re-occurring once it has been initially eliminated (i.e., to prevent a relapse). Alleviating or ameliorating a target disease/disorder includes delaying the development or progression of the disease, or reducing disease severity. Alleviating the disease does not necessarily require curative results. A suitable dose and therapeutic regimen may vary depending upon the specific compound used, the mode of delivery of the compound, and whether it is used alone or in combination.

As used herein, an effective amount generally refers to an amount of a compound (e.g., an inhibitor) that inhibits formation, progression, growth and/or spread (e.g., metastasis) of a tumor or a cell. In some embodiments, the effective amount is an amount of a compound the enters a cell and inhibits CypD. In some embodiments, the effective amount of a CypD inhibitor is sufficient to inhibit an EMT of the cell, tumor formation, progression, growth, and/or spread of a tumor or cell. In some embodiments, the effective amount of a p53Ψ inhibitor is an amount of a compound the enters a cell and inhibits p53Ψ expression or activity. In some embodiments, the effective amount is an amount of a compound the enters a cell and inhibits ROS. In some embodiments, the effective amount of a ROS inhibitor is sufficient to inhibit an EMT of the cell, tumor formation, progression, growth, and/or spread of a tumor or cell.

Methods for establishing an effective amount for any compounds (e.g., CypD inhibitor, p53Ψ inhibitor, ROS inhibitor, or a combination of two or more of a CypD inhibitor, a p53Ψ inhibitor, and a ROS inhibitor) described herein are known to those of ordinary skill in the art. As used herein, pharmacological compositions comprise compounds or compositions that have therapeutic utility and a pharmaceutically acceptable carrier that facilitates delivery of compounds or compositions, in an effective amount. The effective amount for any particular application can also vary depending on such factors as the cancer being treated, the particular compound being administered, the size of the subject, or the severity of the disease or condition. One of ordinary skill in the art can empirically determine the effective amount of a particular molecule without undue experimentation. Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned with the goal of avoiding substantial toxicity and providing effective to treat the particular individual. In some embodiments a useful compound increases the average length of overall survival, increases the average length of disease-free survival, and/or reduces the rate of recurrence (e.g., relapse), of individuals treated with the compound in a statistically significant manner.

Individual doses of the compounds described herein typically range from about 0.1 µg to 10,000 mg, more typically from about 1 µg to 8000 mg, e.g., from about 10 µg to 100 mg once or more per day, week, month, or other time interval. Stated in terms of individual body weight, typical dosages in certain embodiments of the disclosure range from about 0.1 µg to 20 mg/kg/day, e.g., from about 1 to 10 mg/kg/day, e.g., from about 1 to 5 mg/kg/day. The absolute amount will depend upon a variety of factors, including the concurrent treatment, the number of doses and the individual patient parameters, such as age, physical condition, size and weight. These are factors well known to those of ordinary skill in the art and can be addressed with no more than routine experimentation. In some embodiments, a maximum dose is used, that is, the highest safe dose according to sound medical judgment.

The dose used may be the maximum tolerated dose or a sub-therapeutic dose or any dose there between. When more than one dose of an inhibitor is administered (e.g., more than one dose in a time period, such as more than one dose in a 24 hour period), the amount given at each administration is less than that given if a single dose were administered in the same time period. If more than one type of inhibitor is administered (e.g., a CypD inhibitor and a ROS inhibitor), the amount of each type of inhibitor is selected such that the combination produces the desired effect. For example, if two types of inhibitors (e.g., a CypD inhibitor and a ROS inhibitor) are administered, a smaller amount of each will be administered than would be administered if either was administered alone.

Cancer

The methods described are useful to treat cancer characterized by p53Ψ expression. A cancer characterized by p53Ψ expression may be a solid cancer (e.g., a tumor, a carcinoma) or a blood cancer. In preferred embodiments, the cancer is a non-small cell lung carcinoma (NSCLC), upper urinary tract transitional cell carcinoma (UUTCC) or breast cancer. Methods described can used to treat other cancers characterized by p53Ψ expression, which may include biliary tract cancer; bladder cancer; brain cancer including glioblastomas and medulloblastomas; cervical cancer; choriocarcinoma; colon cancer; endometrial cancer; esophageal cancer; gastric cancer; hematological neoplasms including acute lymphocytic and myelogenous leukemia; T-cell acute lymphoblastic leukemia/lymphoma; T cell lymphoma; B cell lymphoma; hairy cell leukemia; chronic myelogenous leukemia, large cell lymphoma, multiple myeloma; AIDS-associated leukemias and adult T-cell leukemia/lymphoma; intraepithelial neoplasms including Bowen's disease and Paget's disease; liver cancer; lung cancer, including non-small cell lung carcinoma (NSCLC); lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Merkel cell carcinoma, Kaposi's sarcoma, basal cell carcinoma, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; renal cancer including adenocarcinoma and Wilms tumor; and upper urinary tract transitional cell carcinoma (UUTCC).

Some aspects of the disclosure are methods for treating an individual having, or suspected of having, cancer comprising administering to the individual an effective amount of a CypD inhibitor. In some embodiments, methods are provided for treating an individual having, or suspected of having, cancer comprising administering to the individual an effective amount of a p53Ψ inhibitor. In some embodiments, the methods involve administering to the individual a combination of two or more inhibitors selected from a CypD inhibitor, a p53Ψ inhibitor and a ROS inhibitor. Other aspects of the disclosure are methods for treating an individual having, or suspected of having, cancer characterized by p53Ψ expression comprising administering to the subject an effective amount of a cancer chemotherapeutic (e.g., doxorubicin, paclitaxel, actinomycin D, camptothecin, and staurosporine) in combination with a CypD inhibitor or a p53Ψ inhibitor.

Pharmaceutical Compositions

Inhibitors described herein (e.g., CypD inhibitors, p53Ψ inhibitors, and/or ROS inhibitors) can be mixed with a pharmaceutically acceptable carrier (excipient), including buffer, to form a pharmaceutical composition for use in treating a target disease such as a cancer. In some embodiments, a chemotherapeutic drug is also mixed or combined with a CypD inhibitors and a pharmaceutically acceptable carrier. In some embodiments, a chemotherapeutic drug is also mixed or combined with a p53Ψ inhibitors and a pharmaceutically acceptable carrier. "Acceptable" means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., Remington: The Science and Practice of Pharmacy 20th Ed. (2000) Lippincott Williams and Wilkins, Ed. K. E. Hoover.

The inhibitors disclosed herein may be administered by any suitable route, such as orally, intranasally, subcutaneously, intramuscularly, intravenously, intra-arterially, parenterally, intraperitoneally, intrathecally, intratracheally, ocularly, sublingually, vaginally, rectally, dermally, or as an aerosol. Depending upon the type of cancer to be treated, compounds may, for example, be inhaled, ingested or administered by systemic routes. Thus, a variety of administration modes, or routes, are available. The particular mode selected will depend upon the particular inhibitor selected, the particular condition being treated and the dosage required for therapeutic efficacy.

According to the methods of the disclosure, inhibitors (e.g., CypD inhibitors, p53Ψ inhibitors, ROS inhibitors, or any combination thereof) may be administered in a pharmaceutical composition. Administering the pharmaceutical composition of the present disclosure may be accomplished by any means known to the skilled artisan. In addition to the active agent, the pharmaceutical compositions of the present disclosure typically comprise a pharmaceutically-acceptable carrier. The term "pharmaceutically-acceptable carrier", as used herein, means one or more compatible solid or liquid filler diluents or encapsulating substances which are suitable for administration to a human or lower animal.

General Techniques

The practice of the present disclosure employs, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, fourth edition (Green and Sambrook et al., 2012) Cold Spring Harbor Press; Oligonucleotide Synthesis (M. J. Gait, ed., 1990); Methods in Molecular Biology, Humana Press; Cell Biology: A Laboratory Notebook (J. E. Cellis, ed., 1998) Academic Press; Animal Cell Culture fifth edition (Rarid and Freshney, 1998); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C C. Blackwell, eds.); Gene Transfer Vectors for Mammalian Cells (J. M. Miller and M. P. Calos, eds., 1987); Current Protocols in Molecular Biology (F. M. Ausubel et al., eds., 2013 J. Wiley & Sons); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999 Janeway's; Immunobiology $8^{th}$ edition (K. Murphy, 2011); Antibodies (P. Finch, 1997); Antibodies: a practical approach (D. Catty., ed., IRL Press, 1988-1989); Monoclonal antibodies: a practical approach (P. Shepherd and C Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995); and Cancer: Principles and Practice of Oncology (V. T. De Vita et al., eds., J. B. Lippincott Company, 7th ed., 2004 or 8th ed., forthcoming in 2008). Further information on cancer may be found in The Biology of Cancer, Weinberg, R A, et al., Garland Science, 2006.

All references described herein are incorporated in their entirety by reference.

EXAMPLES

Figure 1:
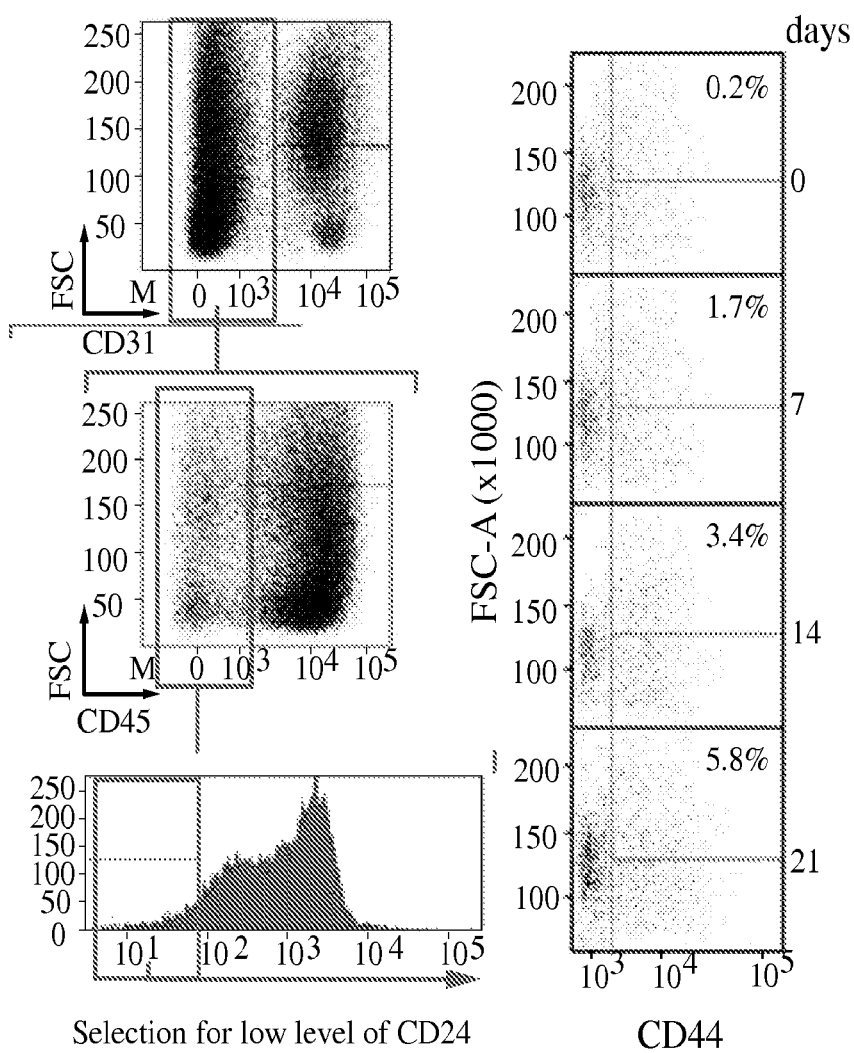
FIG. 1A-H shows that expression of p53Ψ, novel p53 isoforms generated by the use of an alternative 3' splice site, is enriched in CD44high/CD24low cells.
Figure 1:
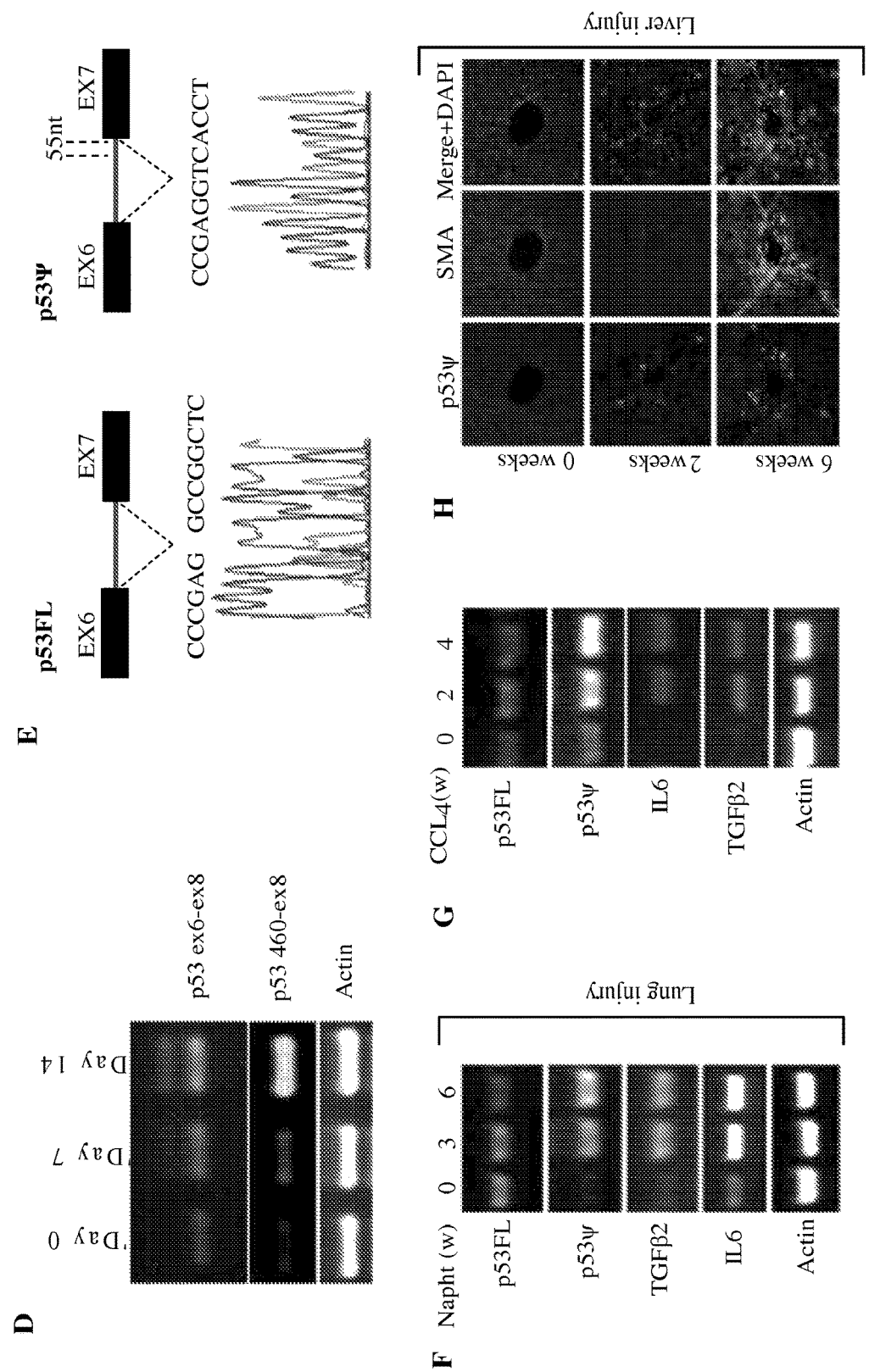
Figure 8:
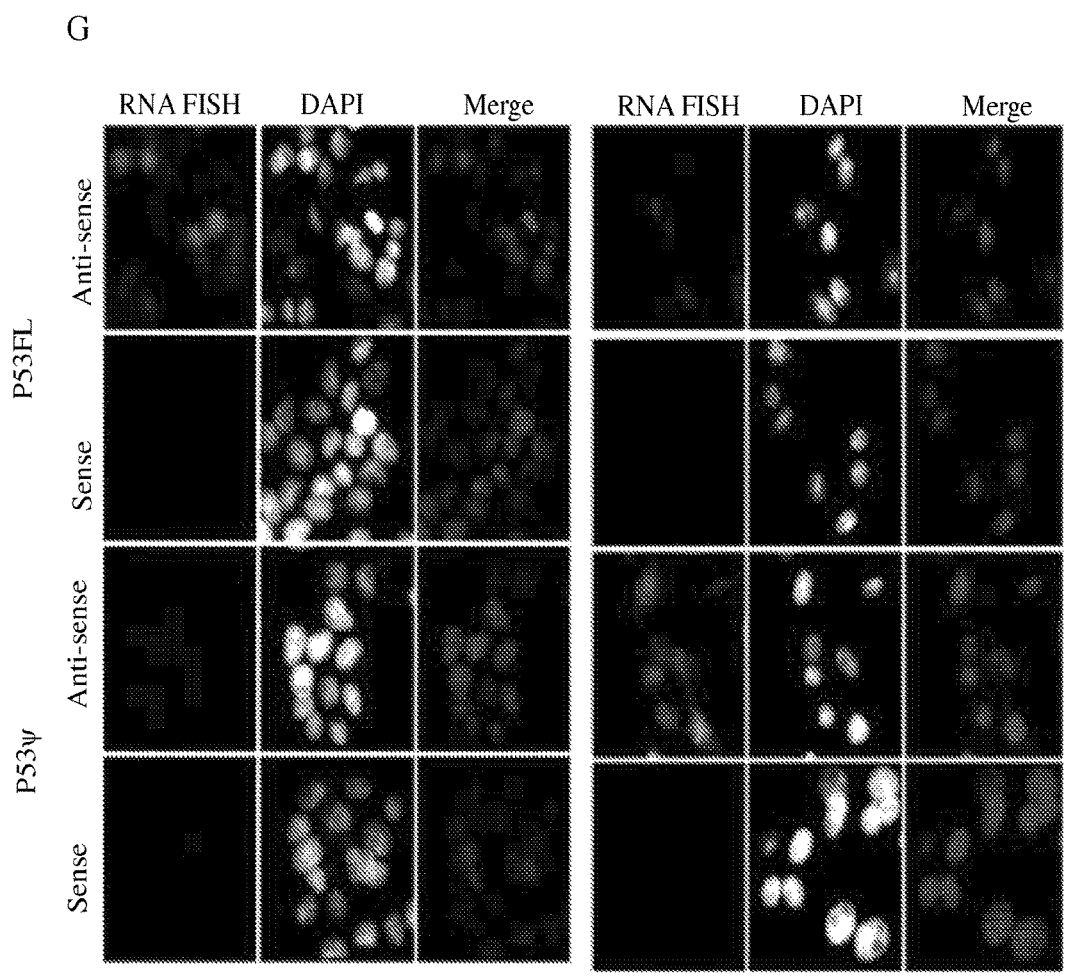
FIG. 8A-G shows expression of p53Ψ in various cells and tissue samples.

Example 1: P53Ψ is a Transcriptionally Inactive Isoform Able to Reprogram Cells Toward a Metastatic-Like State p53Ψ is a Novel p53 Isoform Generated from Use of an Alternative 3' Splice Site In response to strong cellular stresses such as DNA damage or oncogenic signals, p53 regulates the expression of a large cohort of genes that affect cell-cycle arrest, senescence, and apoptosis [1]. It has been uncovered that p53 has essential roles under basal physiological conditions such as regulation of development, reproduction, metabolism, and self-renewal capacity [2], [4], [6], [5]. Interestingly, increased expression of CD44 has been observed in $CD24^{low}$, non-marrow derived cells in tissues upon injury. To investigate whether p53 activity was deregulated upon tissue injury in $CD44^{high}/CD24^{low}$ cells, a murine lung injury model was employed using intra-peritoneal naphthalene administration (FIG. 1A). Naphthalene treatment results in rapid necrotic changes within Clara cells of the terminal and respiratory bronchioles due to conversion of the drug into a toxic form by the cell-specific microsomal enzyme Cyp2F2 [11]. As shown in FIG. 1B, upon single intra-peritoneal injection of naphthalene, an expansion of $CD44^{high}/CD24^{low}$ non-marrow derived ($CD45^-$) and non-endothelial ($CD31^-$) cells was observed in the lung in a time-dependent manner after injury. The population $CD44^{high}/CD24^{low}$ cells increased from near undetectable levels in the vehicle-treated animals to almost 6% of total $CD31^-/CD45^-$ cells by day 21 following naphthalene treatment. Gene expression analysis of fluorescence-activated cell sorted (FACS) cells following injury revealed a reduction in the expression of known p53-regulated genes such as CDKN1A, Triap1, Sens1, Sens2, Pgam1, Pgam2, Sco1, Sco2, Tigar, and Gpx1 in $CD44^{high}/CD24^{low}/CD31^-/CD45^-$ cells compared to $CD44^{low}/C24^{high}/CD31^-/CD45^-$ cells (FIG. 1C and FIG. 8A).

Expression of p53 was evaluated in total lung tissue homogenates taken from naphthalene-treated and untreated animals. RT-PCR analysis using primers spanning exon 6 to exon 8 indicated a slower migrating p53 band in cell extracts obtained from injured lungs, which intensified in the days following naphthalene injection (FIG. 1D). Sequence analysis revealed no mutations in exons 6, 7, or 8 or in intron 6, but indicated that this band was a novel p53 mRNA variant generated by the usage of an alternative 3' splice acceptor site within intron 6 (FIG. 1E and FIG. 8B). This p53 variant is referred to as p53Ψ. Comparison across species revealed that the sequence surrounding the alternative 3' splice acceptor site in intron 6 is highly conserved (FIG. 8C). This observation is surprising given that intronic sequences are usually highly divergent [12]. Using p53Ψ specific primers, enrichment of p53Ψ was verified in $CD44^{high}/CD24^{low}/CD31^-/CD45^-$ cells compared to $CD44^{low}/C24^{high}/CD31^-/CD45^-$ cells upon lung injury (FIGS. 8D and 8E).

To determine if p53Ψ was unique to the naphthalene lung injury model, additional organs and tissue injury models were analyzed. Specifically, expression of p53Ψ was detected in the thymus, salivary gland, small intestine, brain, heart, kidney, skeletal muscle, spleen, stomach, liver, and lung as well as in the livers [13] by RT-PCR analysis, using primers designed to amplify p53Ψ and p53FL mRNAs (FIG. 8D). Expression of p53Ψ was not detected in any of the organs at steady state (FIG. 8F). Similar to what was observed in the lungs of naphthalene-treated mice (FIGS. 1D and 1F), p53Ψ was observed in CCL4 injured livers (FIG. 1G). Using RNA fluorescence in situ hybridization (FISH) expression of p53Ψ in CCL4-treated livers was confirmed and found to be localized in the proximity of tissue lesions (i.e. the SMA-α-positive areas) (FIG. 1H and FIG. 8G).

In sum, these observations indicate the existence of a novel p53 isoform generated through an alternative splicing event that is conserved across species and whose expression appears particularly enriched upon tissue injury.

p53Ψ is Expressed in Human Tumors and Tumor-Derived Cell Lines

Figure 2:
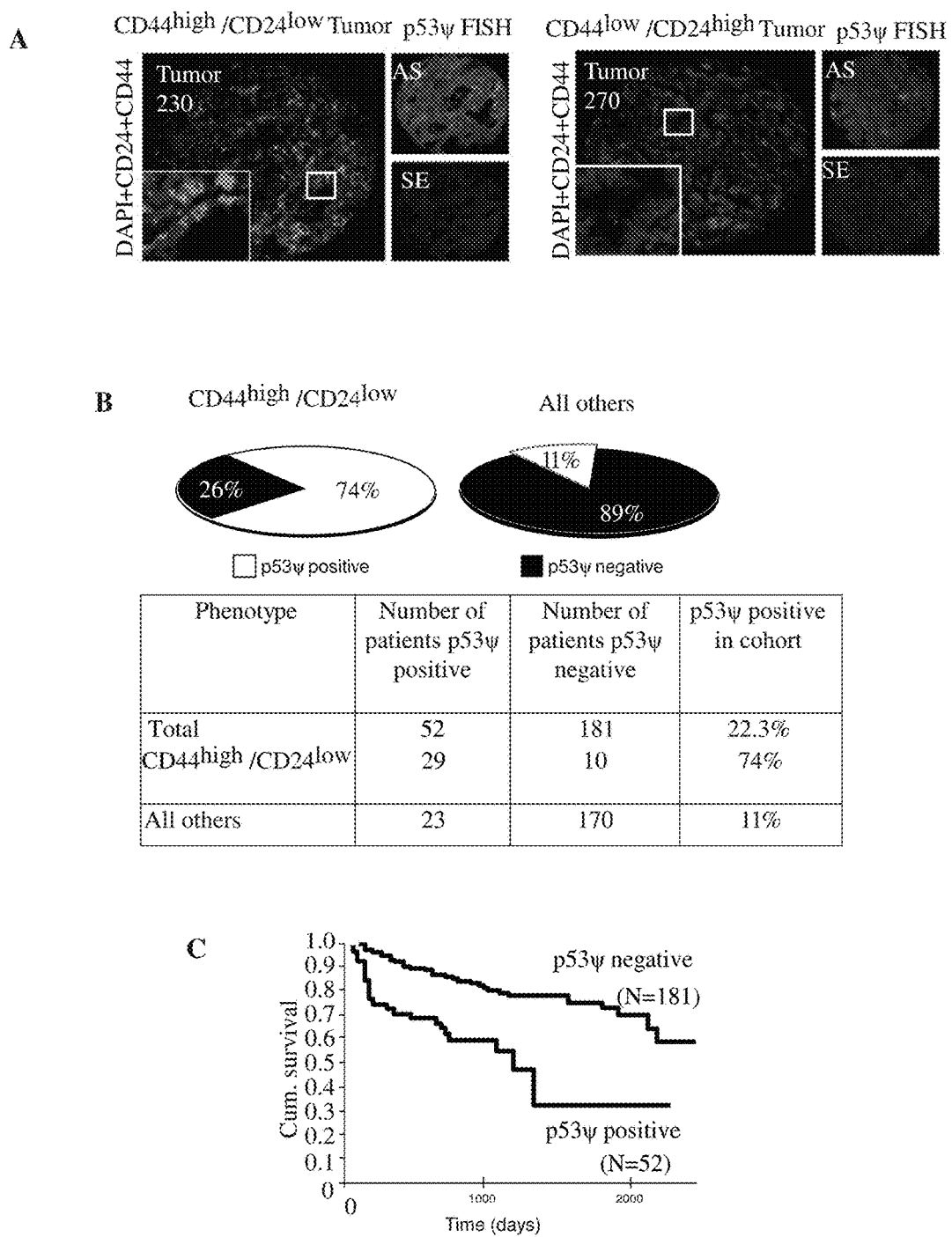
FIG. 2A-L presents p53Ψ expression in tumors and tumor-derived cell lines.
Figure 9:
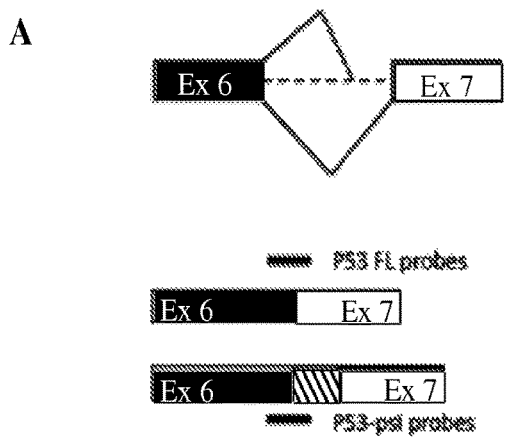
FIG. 9A-N shows the frequency of p53 in a collection of NSCLC tissue samples.
FIG. 9B presents patient demographics for the collection of NSCLC tissues from 233 patient cases that was analyzed for expression of p53Ψ, CD44 and CD24.
FIG. 9C shows lung tumor samples stained for p53Ψ. Significant heterogeneity of staining was observed with certain tumors clearly enriched for p53Ψ. The micrographs represent examples of tumor cores stained with a p53Ψ specific RNA probe by FISH, or immunohistochemically with a p53 N-terminal antibody (P53 DO1). Of note the tumor core in the bottom panels is comprised of both p53Ψ positive and negative cells. A p53 cytoplasmic staining is clearly visible in p53Ψ positive cells.
FIG. 9D presents the CD44 and CD24 staining frequency across the 233 tumor tissue cohort.
FIG. 9E shows that expression of the CD44high/CD24low phenotype was co-linear with p53Ψ staining.
FIG. 9F shows the frequency of p53 relative to the stage of cancer. Enrichment of p53Ψ in early stage tumors is not statistically significant.
FIG. 9G shows the effect of p53Ψ on patient survival. Cox proportional hazards regression analysis for p53Ψ status indicated a HR 1.76, CI 1.074-5.405 with a p=0.001 in p53Ψ tumors.
FIG. 9H shows expression of p53Ψ in FACS-sorted CD44+CD24− A549 cells as evaluated by RT-PCR. The right panel presents sequence analysis of the p53Ψ and p53FL RT-PCR products, indicating the existence of an alternative splice junction in intron 6 that is the human orthologue of p53Ψ identified in murine samples. The sequences in FIG. 9H, from left to right, correspond to SEQ ID NO: 24 and SEQ ID NO: 25.
FIG. 9I shows a representative Western blot analysis of unsorted A549 cells and sorted CD44+CD24− A549 cells. An anti-p53 N-terminal antibody (DO1) was used to determine expression of p53; a tubulin antibody was used for normalization.
FIG. 9J shows a histogram of the frequency of c.673−2A to G/T/C substitution mutations in tumors annotated in the IARC p53 database. Brackets indicate the absolute number of c.673−2A>G/T/C mutations found in a particular tumor type.
FIG. 9K shows a histogram of the frequency of intronic mutations in 28,581 human tumors as reported in the IARC p53 database. The frequency of c.673−2A>G/T/C mutations is shown with the dark gray bar.
FIG. 9L shows analysis of mutations in the TP53 gene in a collection of UUTC tumors from 172 patient cases. Available patients and tumor information are presented.
FIG. 9M shows sequence analysis of the intron 6/exon7 boundary in Hop62 cells indicating the presence of a c.673−2A>G mutation. The sequences in FIG. 9M, from top to bottom, correspond to SEQ ID NO: 16, SEQ ID NO: 17, and SEQ ID NO: 26.
Figure 9:
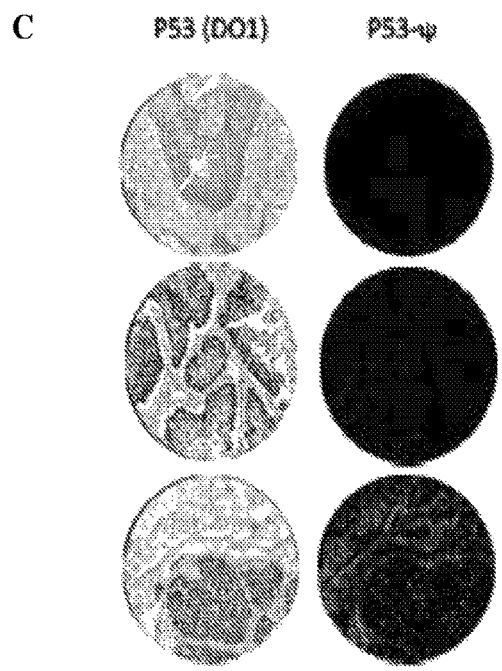
Figure 9:
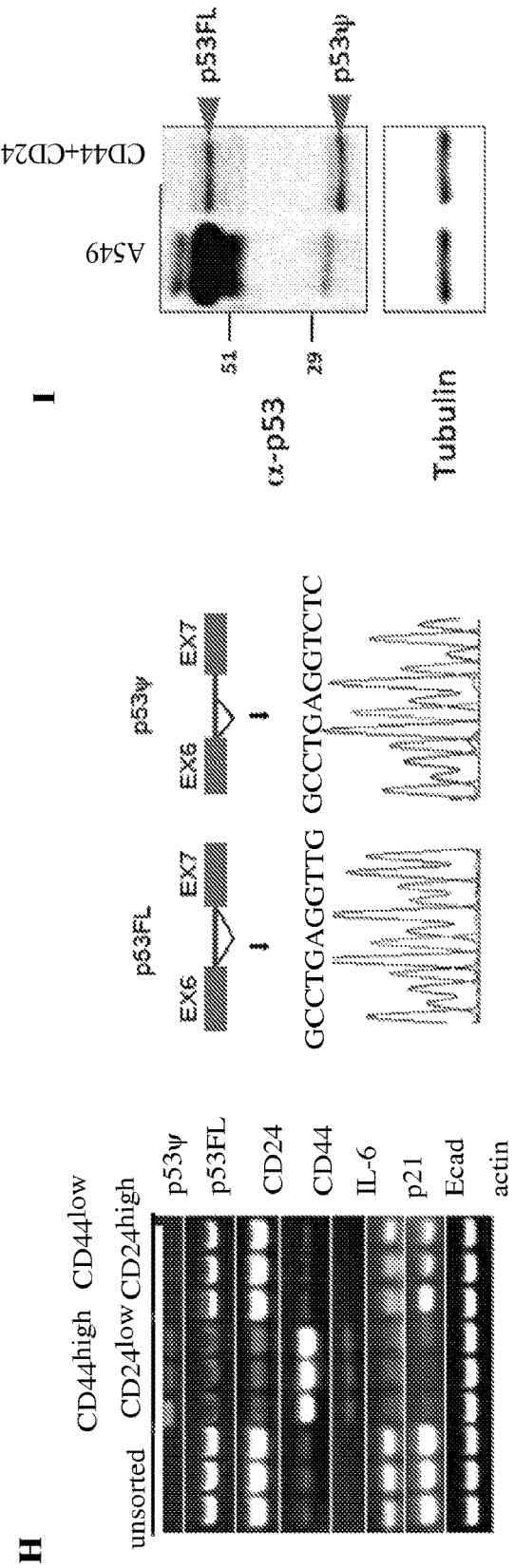
Figure 9:
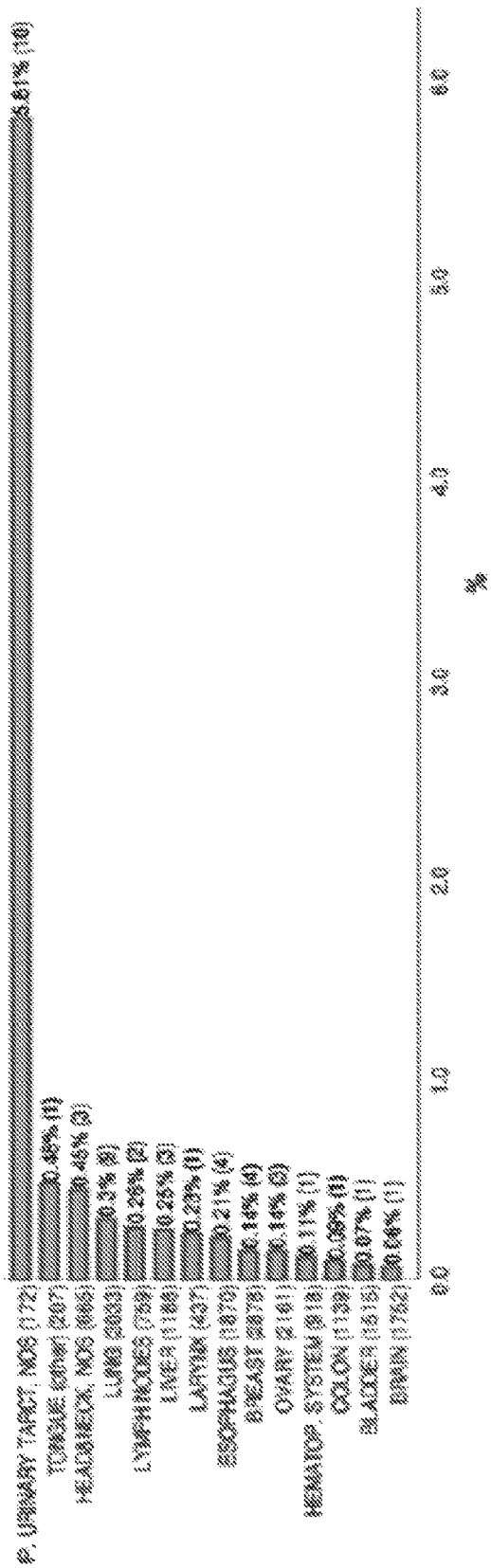
Figure 9:
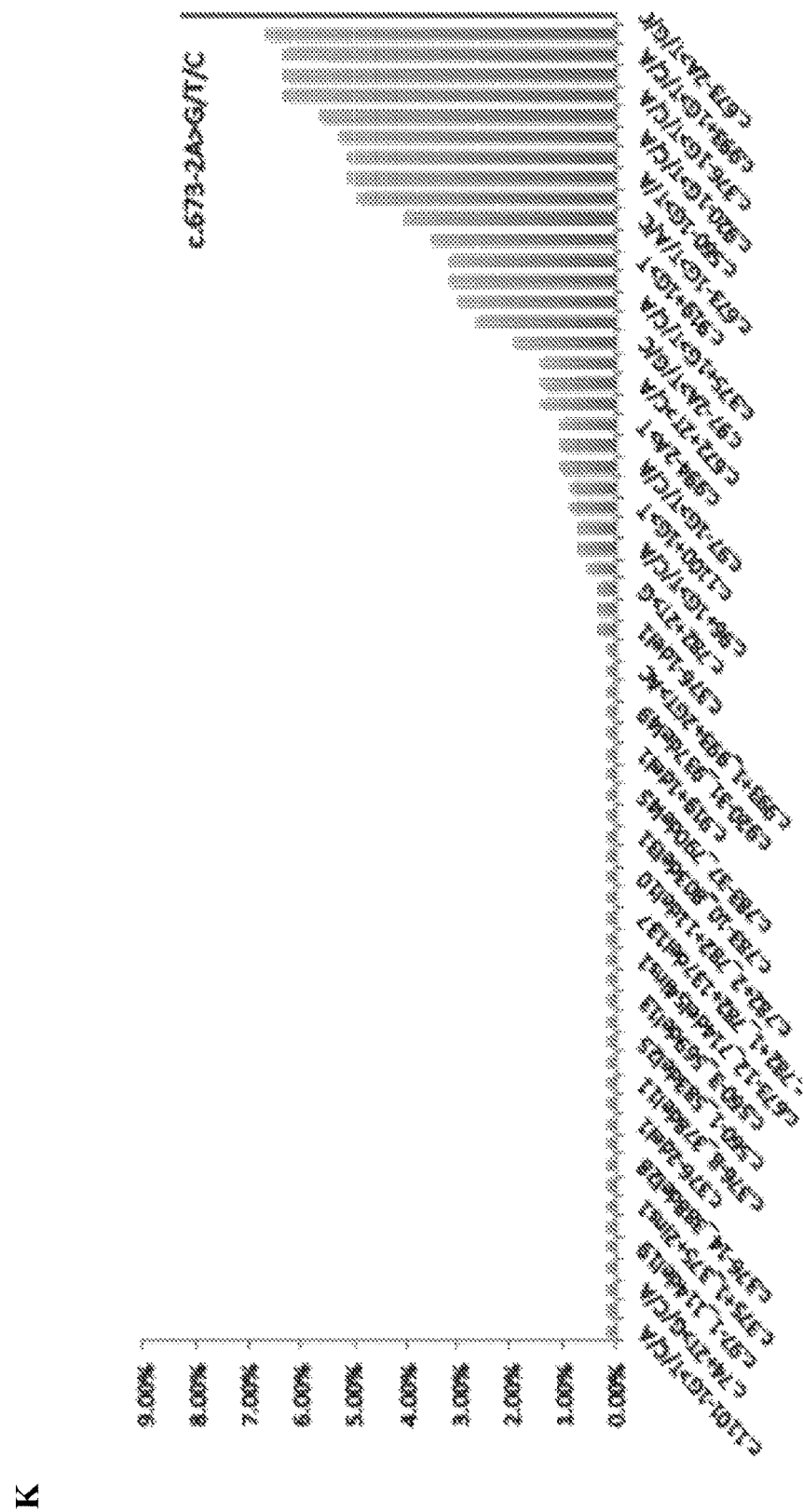
Figure 9:
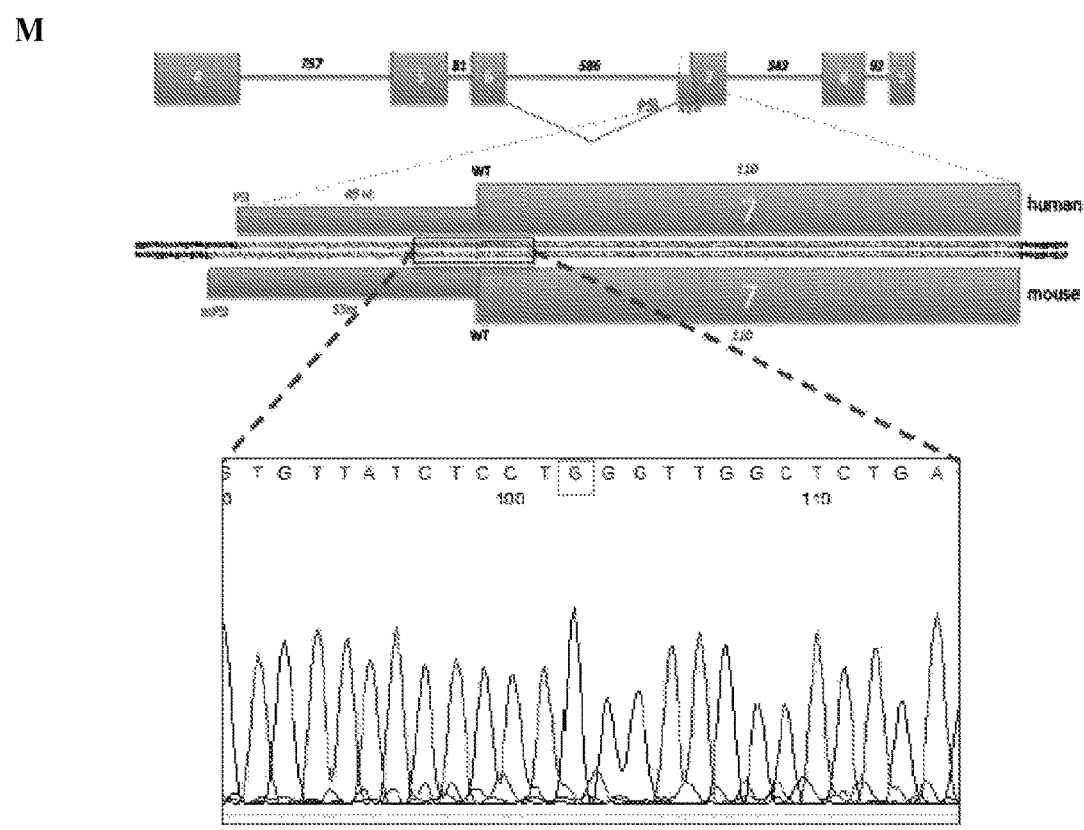
Figure 9:
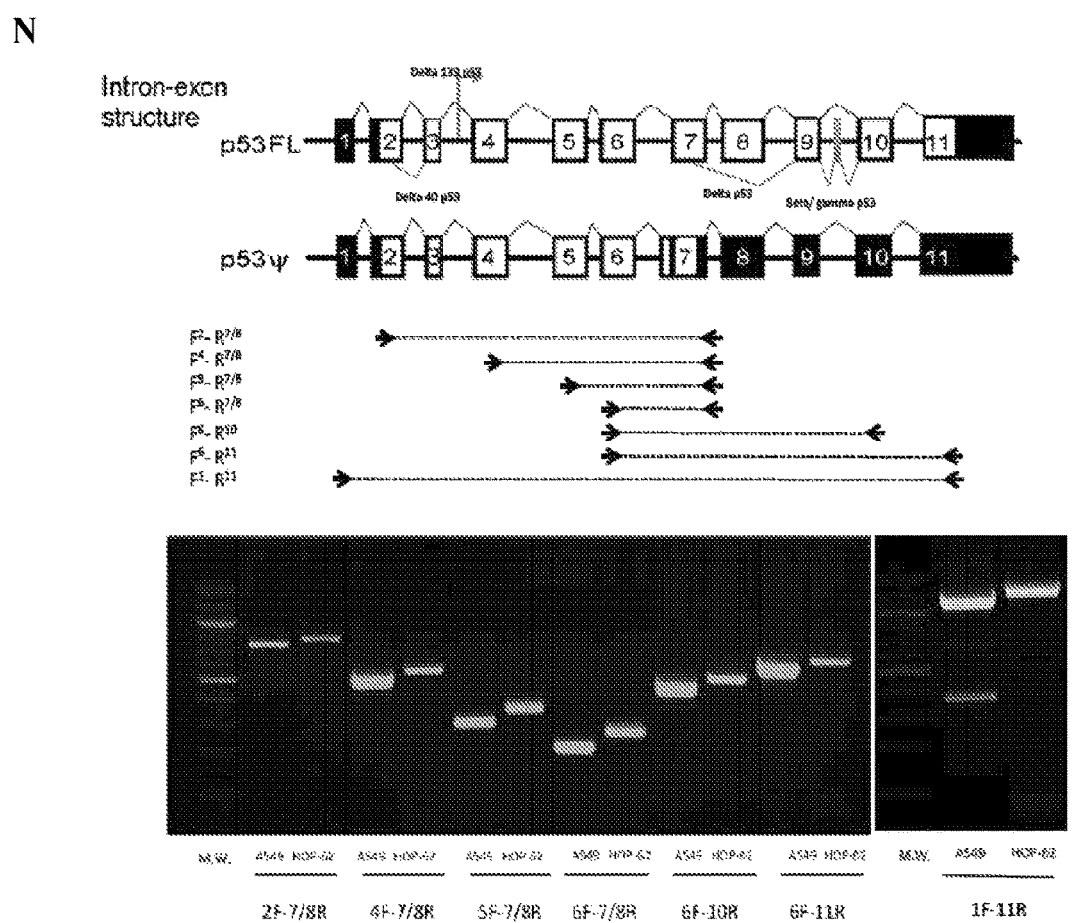

Human tumor analyses have shown that TP53 is mutated in approximately half of all cancers [14]. Somatic p53 mutations occur in almost every type of tumor, at rates ranging from 30% to 50% depending on tumor type [14]. Mutations are more frequent in advanced-stage cancers or in cancer subtypes that are highly metastatic [14]. Generation of p53Ψ could represent an alternative mode of p53 regulation in tumorigenesis. To investigate this, expression levels of p53Ψ and p53FL were evaluated using RNA-FISH on a human tissue microarray (TMA) comprised of non-small cell lung carcinoma (NSCLC) tissues from 233 patients primarily with early-stage adenocarcinomas (FIGS. 9A and 9B). Lung tumor samples were stained with p53Ψ-specific probes. Approximately 22% of tumors clearly expressed p53Ψ (FIG. 2A and FIGS. 9C-9F). Interestingly, the majority of tumor cores that were positive for p53Ψ were constituted primarily of $CD44^{high}/CD24^{low}$ cells (FIG. 2B and FIG. 9E). Uni-variate Kaplan-Meier survival analysis indicated that patients with tumors expressing p53Ψ displayed a decrease in overall survival when compared to the p53Ψ-low group and to p53-null tumors (FIG. 2C and FIG. 9G). In principle this suggests that the generation of p53Ψ does more than create a p53-null state.

It has recently been shown that tumor cells characterized by a $CD44^{high}/CD24^{low}$ immune type can be generated through epigenetic/stochastic events in nearly every tumor-derived cell lines and primary tumors [15]. Given the high abundance of p53Ψ in cells of this immune type in NSCLC and in injured normal tissues, the presence of stochastically generated $CD44^{high}/CD24^{low}$ cells also expressing p53Ψ was evaluated. RT-PCR analysis of FACS-sorted cells from multiple tumor-derived human cell lines using primers specific for p53FL and p53Ψ revealed that p53Ψ was expressed predominantly in the $CD44^{high}CD24^{low}$ cell fraction (FIG. 2D). Sequence analysis confirmed the identity of this presumed p53 isoform as an ortholog of the murine p53Ψ gene (FIG. 9H). In addition, western blot analysis revealed the presence of a band of the expected p53Ψ size in $CD44^{high}/CD24^{low}$ cell extracts (FIG. 9I).

Splicing is carried out by the spliceosome, a massive structure comprised of five small nuclear ribonucleoprotein particles (snRNPs) and a large number of auxiliary proteins that accurately recognizes the splice sites and catalyzes the two steps of the splicing reaction [16]. The decision as to which splice sites are used and which exons are included involve intronic and exonic RNA sequence elements (cis-regulatory elements) and their cognate protein regulators (trans-regulatory factors) [16]. The data presented herein indicates that a regulated switch in p53FL/p53Ψ splice site selection occurs in stochastically generated $CD44^{high}/CD24^{low}$ cells and in injured normal tissues. This suggests that in physiological conditions, controlled changes in abundance or activity of trans-acting factors modulate the p53Ψ alternative splicing events. In tumors, in addition to the deregulation of the proper splicing-factor balance, the occurrence of genetic aberrations affecting cis-regulatory elements could also result in aberrant p53Ψ expression. The splicing reaction requires the presence of a highly conserved AG intronic dinucleotide at the intron/exon boundary at the 3' acceptor site. Hence, mutations in the normal acceptor site at the intron 6/exon 7 boundary (−1G to A/T/C or −2A to G/T/C with respect to the splice junction) could favor the use of the cryptic acceptor site in intron 6 generating the p53Ψ isoform. The IARC TP53 database was probed for mutations at the intron 6/exon 7 boundary and revealed that the G/T/C mutations at position c.673−2A indeed occur in multiple tumors including NSCLC (FIG. 2E and FIG. 9L). These were the most frequent intronic mutations observed in the TP53 gene (FIG. 9M). Among different tumor types, these mutations were also found to be particularly enriched in upper urinary tract transitional cell carcinoma (UUTCC) (FIG. 9L). Mutation analysis of 172 UUTCC samples (FIG. 9L) indicated these are the most frequent TP53 mutations in this type of cancer (FIG. 2F). Given the conservation of AG residues at all splicing sites, the high frequency of mutations at the intron 6/exon 7 boundary acceptor site indicates a functional selection of this particular mutation.

Several studies have demonstrated a significant correlation between the spectrum of p53 mutation and exposure to certain types of carcinogens. For example, transversions in codon 157, though uncommon in other types of cancer, are mutation hotspots in lung, breast, and head and neck cancers and are associated with smoking in lung cancer patients. In the case of UUTCC, the occurrence of carcinoma in this highly unusual location has been associated with dietary exposure to aristolochic acid [17], [18]. Following metabolic activation, aristolochic acid reacts with genomic DNA to form aristolactam-DNA adducts that generate with high frequency A to T transversions in the p53 gene [18]. Since all patients with tissues part of the cohort analyzed had been exposed to aristolochic acid, this could explain the prevalence of c.673−2A mutations observed in this tumor compared to others.

To verify that the presence of mutation at position c.673−2A alters p53 splicing, a mini-gene was generated that contains the genomic fragment from exons 5 to 8 under CMV promoter control (FIG. 2G). Detection and analysis of minigene-derived transcripts were achieved by RT-PCR. Consistent with the observation that normal cells preferentially express p53FL, the minigene expressed the expected transcript with the expected sequence at the exon/intron junction (FIG. 2H). However, mutation of the invariant A residue to G at the 3' acceptor site of intron 6 resulted in the generation of a p53Ψ isoform (FIG. 2H).

To provide further evidence that the presence of intron 6 mutations could result in the generation of a p53Ψ-like transcript, a NSCLC derived cell line (HOP62) that was reported to harbor a c.673−2A to G mutation was also analyzed. Sequence analysis verified the presence of the mutation (FIG. 9O). The expression of a p53Ψ-like transcript was confirmed by RT-PCR analysis using primers complementary to sequences in exon 4 and exon 7 (FIG. 2I). Western blot analysis of HOP62 cell extracts with a p53 N-terminal antibody also indicated the presence of a protein of 27 kDa, the size of the p53Ψ protein (FIG. 2L).

Several alternative p53 isoforms generated by alternative splicing mechanisms have been previously described (FIG. 9P) [19]. To determine whether p53Ψ co-occurs with any of these p53 splicing isoforms, RT-PCR analysis was performed utilizing oligonucleotides spanning the entire p53 coding sequence in cells harboring a p53FL allele compare to cells harboring a homozygous c.673−2A mutation (FIG. 9P). The TA p53Ψ-alpha isoform was the main isoform expressed in HOP62 cells.

p53Ψ is Devoid of Transcriptional Activity

Figure 10:
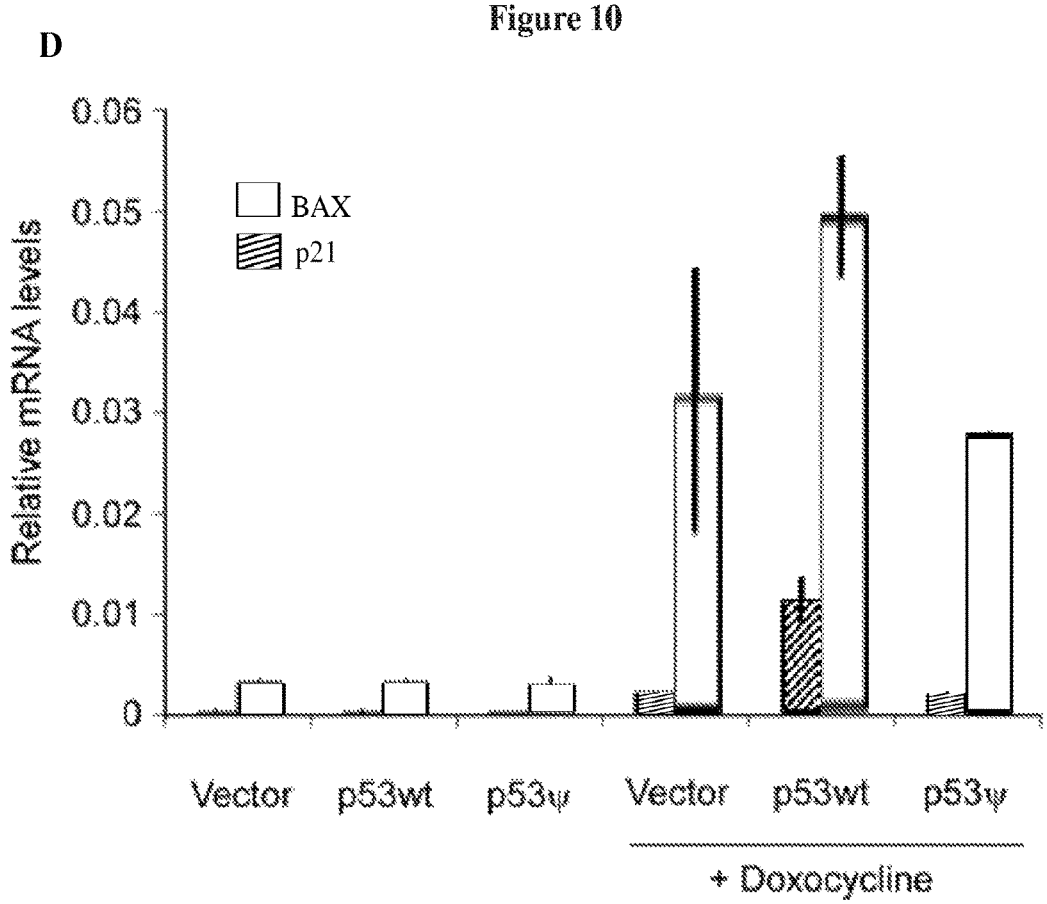
FIG. 10A-D shows p53ψ is devoid of transcriptional activity and does not modify the transcription activity of p53FL (lacks dominant-negative activity).

Due to the generation of an early stop codon, the p53Ψ isoform encodes a p53 protein that is devoid of critical residues required for DNA binding, oligomerization, and localization to the nucleus (FIGS. 3A, B). The cellular distribution of p53FL and p53Ψ evaluated by immunofluorescence in HOP62 cells and in p53-null cells (H1299) expressing either isoform, showed remarkable differences (FIG. 3C and FIG. 10A). Whereas p53FL was mainly localized in the nucleus, p53Ψ was excluded from the nucleus and predominantly localized in the cytoplasm in a partly punctate pattern. These observations were confirmed by biochemical fractionation in A549 cells ectopically expressing p53Ψ and p53FL (FIG. 3D). Similar to the results from immunofluorescence, p53FL was found in nuclear fractions and p53Ψ in cytoplasmic fractions.

To explore whether the absence of the nuclear localization sequence and oligomerization-domain and truncation of the DNA binding-domain affected transcriptional activity of p53Ψ, p53FL and p53Ψ were ectopically expressed in p53-null cells (H1299) and expression of known p53 targets was measured. Although overexpression of p53FL was sufficient to augment PUMA, TIGAR and p21 mRNA (FIG. 3E) and p21 protein levels (FIG. 10B), overexpression of p53Ψ failed to elicit such a response. To directly compare p53Ψ and p53FL transcriptional activity, the activation of a p53-responsive promoter was measured in cells ectopically expressing either p53FL or p53Ψ. As shown in FIG. 3F, luciferase reporter assays using a synthetic p21CIP1 promoter (e.g. p21CIP1-luc) confirmed that p53Ψ was transcriptionally inactive.

To determine whether ectopic expression of p53Ψ could affect p53 target gene transcription by acting in a dominant negative fashion (e.g. by titrating p53 interacting proteins), p53Ψ was ectopically expressed in cells expressing p53FL (A549). In principle a putative dominant negative effect of p53Ψ could be promoter-specific. Thus, in addition to PUMA, BAX and p21, the analysis was extended to a broader array of p53 targets (i.e. tiger, sod2, sgo2, cycg2, sharp1, gpx1, send and sens2). However, no differences in the expression of any of these p53 target genes were observed in cells harboring wild-type p53FL upon overexpression of p53Ψ, neither in basal conditions (FIG. 10D) nor upon stimulation with doxorubicin (FIG. 3G).

Figure 4:
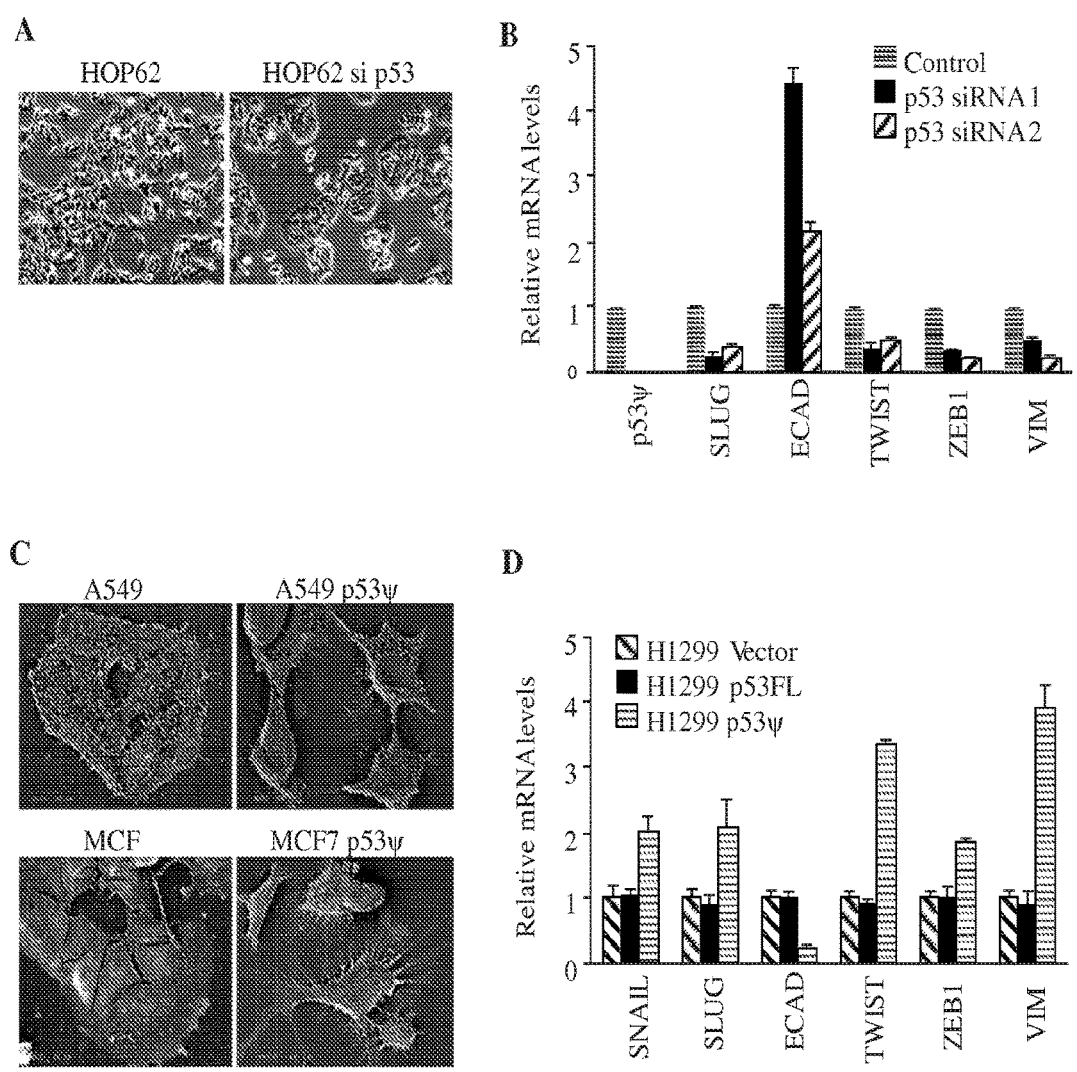
FIG. 4A-F shows that the p53 splice variant, p53Ψ, is sufficient to reprogram cells towards the acquisition of pro-metastatic features.
Figure 11:
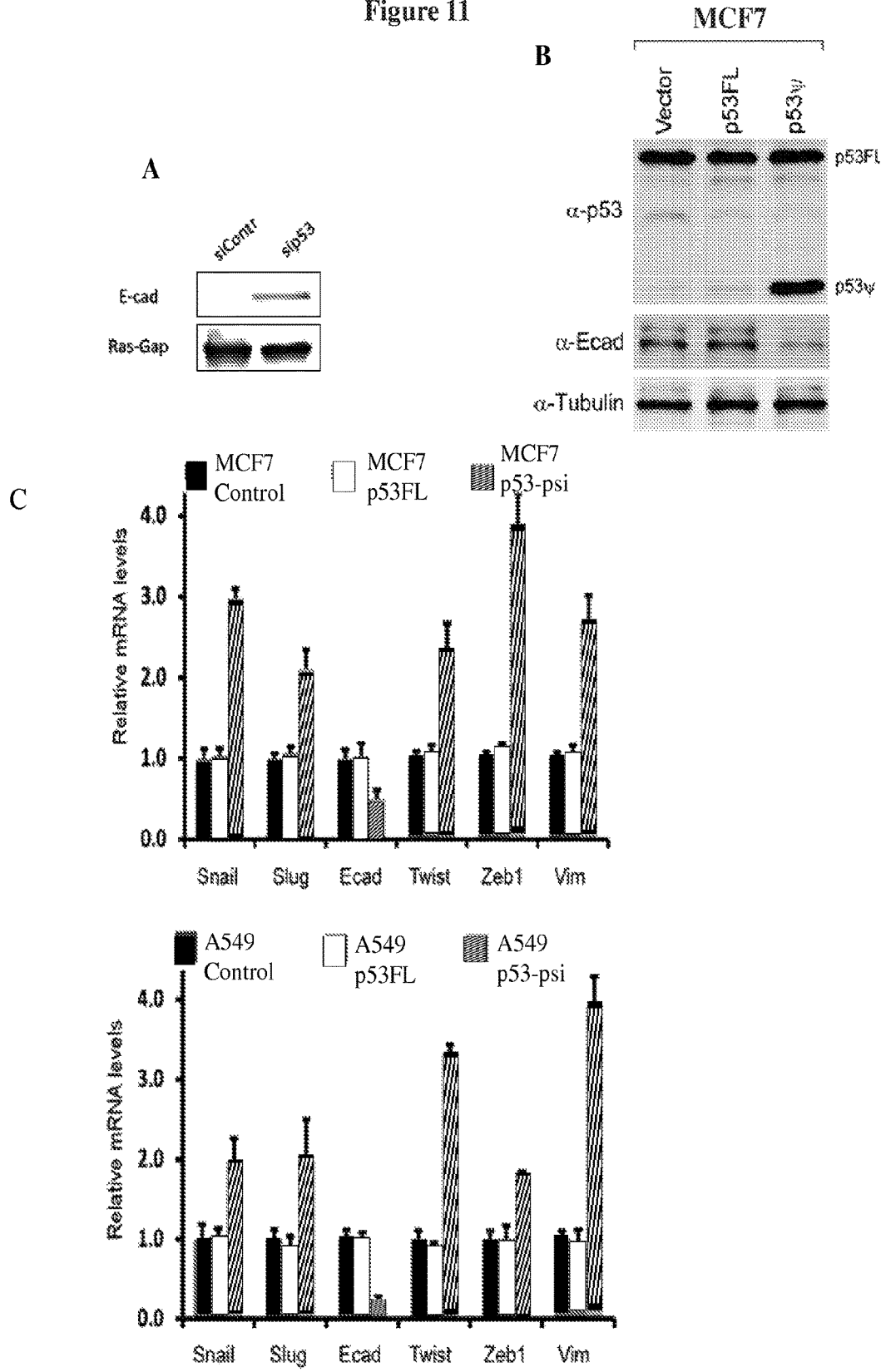
FIG. 11A-E shows that ectopic expression of p53ψ results in the acquisition of mesenchymal-like characteristics.
Figure 11:
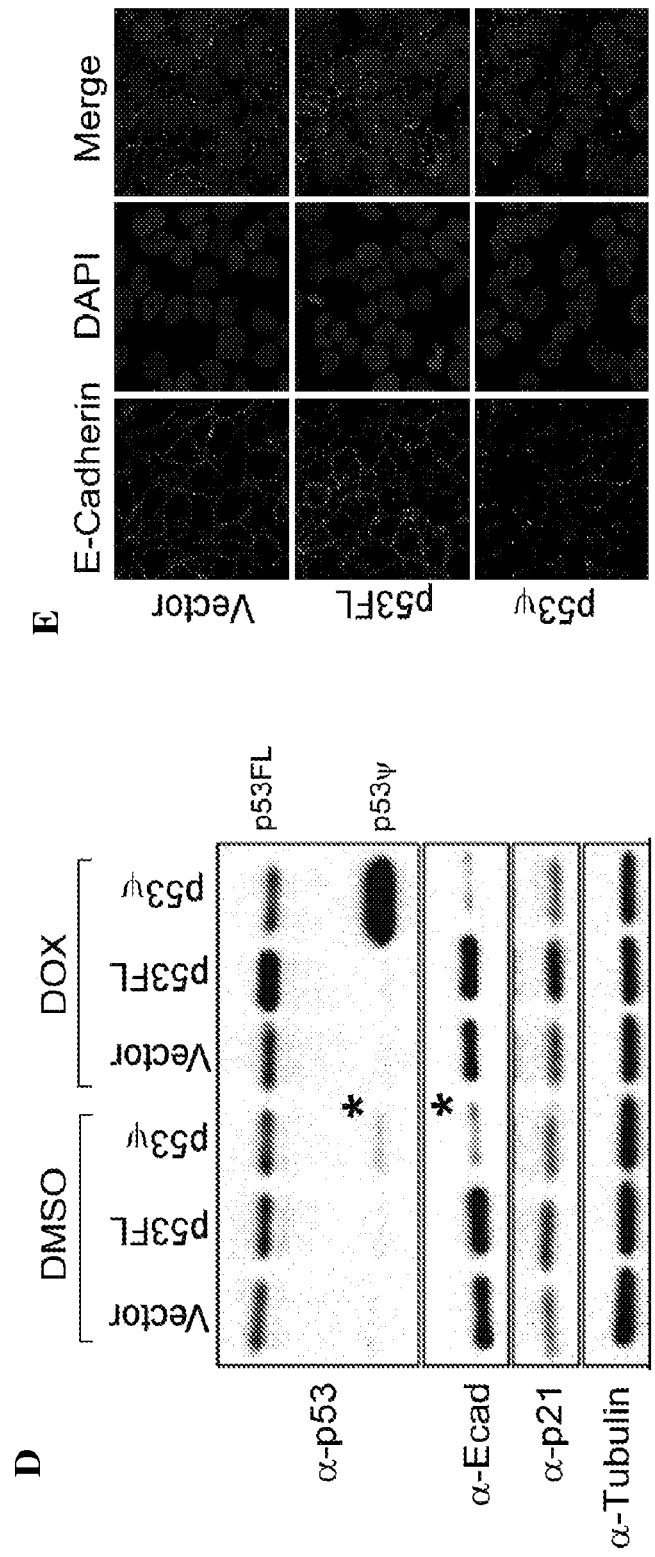

In sum, this demonstrates that p53Ψ is devoid of transcriptional activity. Promoting the generation of p53Ψ at the expense of p53FL represents a novel physiologically relevant mode to limit p53 tumor suppression function. Indeed, decreased expression of p53 target genes and increased expression of genes repressed by p53 is consistently observed in cells expressing p53Ψ (FIG. 1C).

p53Ψ, Like Certain p53 Gain-of-Function Mutations, is Sufficient to Reprogram Epithelial Cells Towards the Acquisition of Pro-Metastatic Features Somatic alterations of the p53 tumor suppressor gene located on chromosome 17p often occur in cancers and are associated with poor prognosis [21]. In these tumors, p53 mutations disable p53-mediated inhibition of proliferation and promotion of apoptosis in response to stress [21]. In addition, missense p53 mutations may have gain-of-function activities that lead to an increased metastatic spread [22]. The observed decrease in average disease-free and overall survival times in patients with tumors expressing p53Ψ (FIG. 9G) and the high frequency of the c.673−2A to G mutation in cancer patients and in patients with upper urinary tract transitional carcinoma (FIG. 2F and FIG. 9M) suggest that cancer-associated p53Ψ does more than create a p53-null state. To test this hypothesis p53Ψ expression was silenced in HOP62 cells. These mesenchymal cells are homozygous for the c.673−2A to G mutation and inherently express exclusively a p53Ψ-like isoform (FIG. 2I and FIG. 9O). Knockdown of p53Ψ in these cells resulted in phenotypic and molecular changes distinctive of cells undergoing mesenchymal to epithelial transition. Cells in which p53Ψ expression was silenced lost the elongated appearance typical of mesenchymal-like cells and instead acquired a cobblestone morphology characteristic of epithelial cells (FIG. 4A). At the molecular level, these changes were associated with increased expression of E-cadherin and diminished expression of vimentin and the "master regulators" of the EMT program Zeb1, Twist and Slug (FIG. 4B and FIG. 11A).

Conversely, ectopic expression of p53Ψ was sufficient to induce morphological (FIG. 4C) and molecular changes (FIG. 4D and FIG. 11A-11E) typical of cells undergoing EMT. This was independent of their pre-existing p53 status, as cells that expressed p53FL (MCF7) and p53-null cells (H1299) both showed decreased expression of E-cadherin but enhanced expression of Vimentin, Snail, Zeb1, Twist and Slug upon p53Ψ expression (FIG. 4D and FIG. 11C).

TP53 is a tumor suppressor whose full length ectopic expression transcriptionally activates stress responses. Although p53Ψ is devoid of transcriptional activity, to further exclude the possibility that the observed phenotypes were due a selection mechanism in response to cellular stress, the effect of p53Ψ expression was tested in a tetracycline inducible A549-based cell line. Like cells that constitutively express p53Ψ, transient expression of p53Ψ in these cells was also able to reduce the expression of E-cadherin (FIGS. 11C and 11D). Of note, changes in E-cadherin were also apparent when analyzing its distribution. Whereas in A549 cells at confluence, E-cadherin was mostly localized at cell-cell junctions, in A549 cells ectopically expressing p53Ψ, E-cadherin was mainly localized in the cytoplasm (FIG. 11E).

In general, cells acquiring mesenchymal-like features tend to be more motile and more invasive. When cell migration was scored in vitro in a standard wound-healing assay, A549 cells expressing p53Ψ closed the cell monolayer opening more rapidly than cells expressing p53FL (FIG. 4E). Similarly, A549 cells expressing p53Ψ had enhanced capability to migrate through a complex extracellular matrix compared to cells expressing p53FL (FIG. 4F). In the EMT transition, increased motility and cell invasion are important hallmarks of metastatic cells [23], [24]. Hence, the observed decrease in average disease-free and overall survival times in patients with tumors expressing p53Ψ (FIG. 2C) supports a general relevance of p53Ψ in reprogramming cells towards the acquisition of pro-metastatic features.

Figure 5:
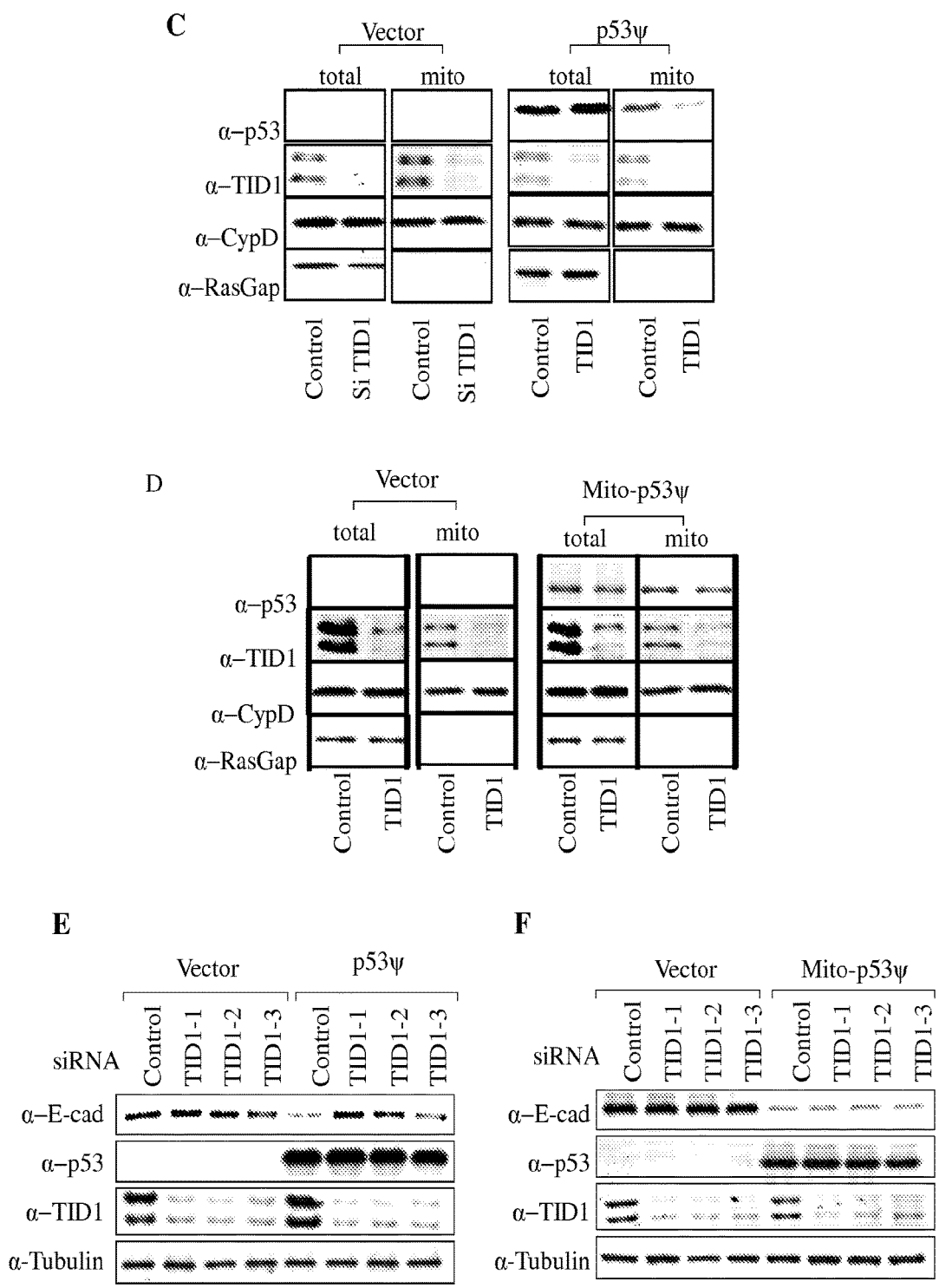
FIG. 5A-F shows that mitochondrial localization of p53Ψ is required for the p53Ψ-induced epithelial to mesenchymal transition (EMT).

Mitochondrial Localization of p53Ψ is Required for Induction of the Epithelial to Mesenchymal Transition In the case of endogenous p53FL, p53 mitochondrial localization has been observed under stress conditions and upon MDM2-induced p53 ubiquitination [27], [28]. The mitochondrial localization of p53 is important in mediating certain transcription-independent activities [25], [26], [27]. Since p53Ψ was entirely excluded from the nucleus and devoid of transcriptional activity, the localization of p53Ψ to the mitochondria was explored and, if so, whether this was required for the p53Ψ-induced epithelial to mesenchymal transition. Of note, when the sub-cellular distribution of p53Ψ was evaluated by immunofluorescence and biochemical fractionation, p53Ψ was partially localized into the mitochondrial matrix under basal growing conditions (FIGS. 5A and 5B).

In eukaryotic organisms, about 10 to 15% of nuclear genes encode mitochondrial proteins [29]. These proteins are synthesized in the cytosol and are then translocated to the mitochondrial inner or outer membranes or to the mitochondrial intermembrane space or matrix [29]. Although many proteins that translocate to the mitochondrial matrix possess an N-terminal targeting sequence called matrix-targeting sequence (MTS), many mitochondrial precursors do not contain an MTS. For precursors without an MTS, chaperone proteins may stabilize and assist in their transport to mitochondria [29], [30]. In the case of p53, the chaperone protein Tid1 has been shown to interact with the N-terminal domain of p53 and to mediate its translocation into the mitochondrial matrix [31,32]. Tid1, also known as mitochondrial Hsp40 (mtHsp40), is the mammalian homolog of the *Drosophila* tumor suppressor Tid56 [33]. Tid1 contains a conserved DnaJ domain through which it interacts with the cytosolic Hsp70 family of chaperone proteins that are also engaged in mitochondrial transport of MTS-deficient proteins [33]. DnaJ-like proteins function as co-chaperones with DnaK-like ATPases to promote the (un)folding and translocation of polypeptides.

To determine whether Tid1 is involved in the translocation of p53Ψ to mitochondria, Tid1 was silenced and its effect on the sub-cellular localization of p53Ψ was assessed. Biochemical fractionation indicated that decreased expression of Tid1 was sufficient to reduce the amount of p53Ψ transported into the mitochondria without affecting the localization of cyclophilin D (CypD), a protein localized in the mitochondrial matrix via an MTS (FIG. 5C). In further support of Tid1-mediated p53Ψ mitochondrial localization, a p53Ψ construct was generated that was constitutively localized to the mitochondria independent of Tid1 by the presence of an N-terminal MTS tag (mito-p53Ψ). As predicted, the presence of an MTS sequence was sufficient to overcome the effect of Tid1 silencing (FIG. 5D).

Next, it was determined whether the translocation of p53Ψ into the mitochondrial matrix was required for p53Ψ-induced EMT. Indeed, silencing of Tid1 in cells expressing p53Ψ resulted in a failure of p53Ψ to decrease the expression of E-cadherin and in a decreased p53Ψ-mediated increase in cell motility (FIG. 5E and FIG. 12A). Notably, no difference in E-cadherin expression was observed in cells in which Tid1 was silenced but p53Ψ was not expressed (i.e. vector-transfected cells). Because the effect of Tid1 silencing on the regulation of EMT could be independent of p53Ψ, constitutive mitochondrial localization of p53Ψ was induced in a Tid1-independent manner (i.e. using mito-p53Ψ). Even in the absence of Tid1, mito-p53Ψ expressing cells were characterized by decreased E-cadherin levels (FIG. 5F). This evidence indicates that p53Ψ is partially localized to the mitochondrial matrix in a Tid1-dependent fashion, and that localization to the mitochondria is both necessary and sufficient for induction of an EMT phenotype by p53Ψ.

p53Ψ Interaction with Cyclophilin D is Sufficient to Increase Mitochondrial Pore Permeability and Reactive Oxygen Production When localizing to the mitochondria under apoptotic conditions, p53 modulates the activities of anti-apoptotic (Bcl-xL and Bcl-2) and pro-apoptotic (BAK/BAX) members of the Bcl-2 family to regulate the integrity of the outer mitochondrial membrane [26]. p53FL interactions with Bcl-xL/Bcl-2 and BAK resulting in BAK oligomerization with subsequent outer membrane permeabilization (MOMP) and release of cytochrome C and other pro-apoptotic factors into the cytoplasm, mediating apoptosis [26]. Within the matrix, p53 has been shown to interact with MnSOD, the primary antioxidant enzyme in mitochondria, and with CypD, an obligatory activator of the mitochondrial permeability transition pore (mPTP) that is closed in healthy cells. To determine if p53Ψ interacts with any of these proteins, immunoprecipitation experiments were performed. Because CypD is localized in the mitochondrial matrix, the input materials for the immunoprecipitation experiments were fractions containing outer mitochondrial membrane/intermembranous space and inner mitochondrial membrane/matrix. We found that mitochondrial p53Ψ was unable to bind to BAX, BAK and MnSOD (FIG. 12A) but reproducibly interacted with CypD (FIG. 6A). Consistent with a failure to interact with BAX and BAK, cells expressing p53Ψ were viable and did not release cytochrome C from their mitochondria (FIG. 12E).

Previous studied have shown that the interaction between p53 and CypD is mediated by a portion of the DNA binding domain of p53 [27]. This portion of p53 is fully retained in p53Ψ. To determine whether the residual DNA binding domain (amino acids 102-243) can mediate p53Ψ interaction with CypD and determine whether the interaction is direct, pull-down experiments were performed. As shown in FIG. 12C, GST-tagged CypD selectively precipitated recombinant p53Ψ, hence the interaction appears to be direct.

Having shown that p53Ψ was able to bind directly to CypD, a functional role for the p53Ψ/CypD interaction in cells was explored. Because the only known activity of CypD is regulation of the mPTP opening, the effect of p53Ψ on the mitochondrial permeability transition pore was measured using calcein release, a highly selective indicator of sustained PTP opening in situ [34] [35]. Of note, MOMP and the Bax/Bak lipid pore are completely incompetent for calcein release [36]. In this assay, cells are loaded with Calcein (acetomethylester) together with its quencher Cobalt ions. Calcein freely diffuses throughout the cell including into the mitochondrial matrix. But the Cobalt quencher cannot diffuse across the inner mitochondrial membrane, therefore quenching Calcein fluorescence everywhere except in the mitochondrial matrix. Thus, Calcein fluorescence comes only from the matrix. Only upon PTP opening will Cobalt ions gain access to the matrix and quench Calcein, resulting in a sharp drop of mitochondrial fluorescence, which can be measured by FACS or microscopy (FIG. 6B). Notably, cells expressing p53Ψ exhibited increased mPTP permeability relative to cells that did not express this p53 isoform (FIGS. 6C and 6D). This effect was CypD-dependent, since treatment with Cyclosporine A (CsA), a highly selective pharmacological inhibitor of CypD, reduced $CoCl_2$-mediated quenching of calcein fluorescence (FIGS. 6C and 6D). Although CsA also inhibits other cytosolic cyclophilins in addition to mitochondrial matrix-specific CypD, none play any role in the regulation of the mPTP pore opening. As a control, cells that had been loaded with calcein AM were treated with the ionophore ionomycin. In the presence of ionomycin, we observed a rapid loss of mitochondria calcein fluorescence in all experimental settings (FIGS. 6C and 6D).

An increase in the time that the mPTP is in the open state will result in an increased outflow of electrons with increased accumulation of ROS inside the mitochondria [37]. To assess levels of superoxide in the mitochondria of live cells, the fluorogenic dye MitoSOX was used [38]. When added to cells, the MitoSOX reagent is rapidly and selectively targeted to mitochondria, where MitoSOX is oxidized by superoxide. When exited with a light at 390 nm frequencies, it emits red fluorescence. Upon loading with MitoSOX, cells expressing p53Ψ exhibited increased MitoSOX staining when compared to p53FL-expressing cells and/or vector control (FIGS. 6E and 6F). Consistent with increased mPTP opening mediated by the interaction of p53Ψ with CypD, the increased MitoSOX fluorescence was again decreased upon inhibition of CypD with CsA (FIGS. 6E and 6F).

Recently it was reported that upon oxidative stress, p53FL translocates to the mitochondrial matrix and triggers sustained mPTP opening by engaging in a physical interaction with CypD, thereby inducing necrotic cell death [27]. Confirming these data, when p53FL was forced into the mitochondrial matrix by generating an N-terminal MTS fusion protein, massive cell death was observed. This was not the case when either mitochondria-targeted p53 gain-of-function mutants or p53Ψ were expressed either in p53-null cells or in cells expressing p53FL (FIG. 12D). There were no major observable differences in CypD binding or in mitochondrial permeability when p53FL, p53Ψ, and p53 gain-of-function mutants were compared, suggesting that interaction with CypD and/or an increased mitochondrial permeability, although required for mitochondrial p53FL-mediated cell death, is not sufficient but also requires oxidative damage.

Figure 7:
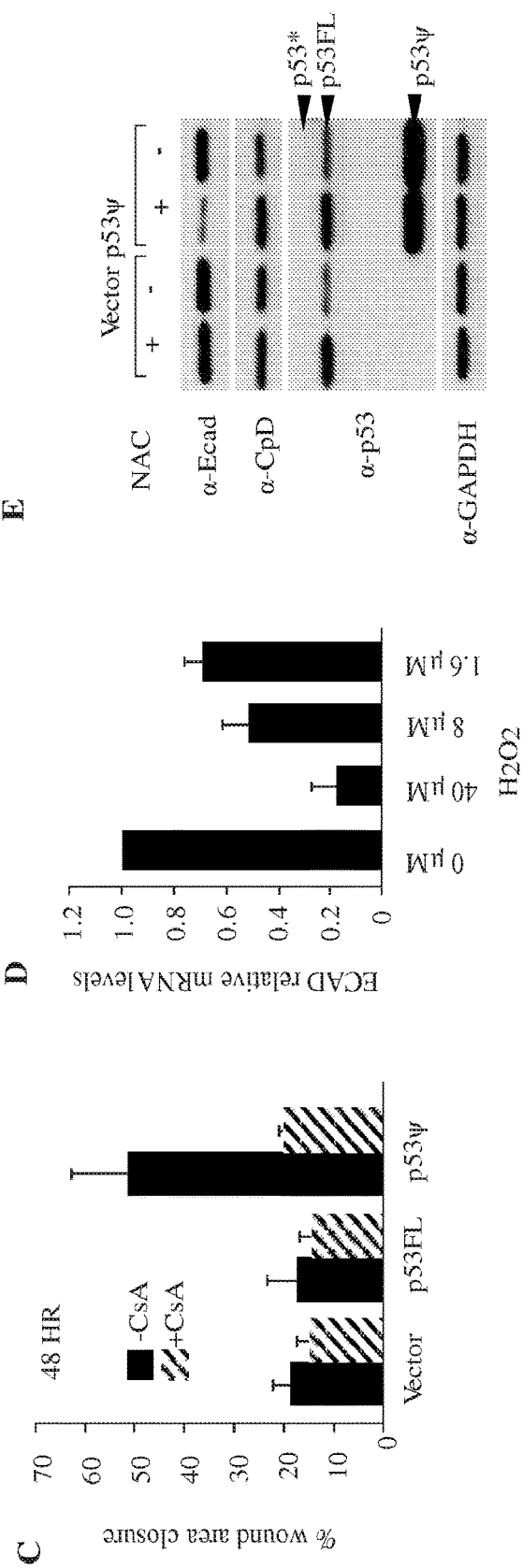
FIG. 7A-F shows that CypD and reactive oxygen species are required for EMT induction by p53Ψ.
Figure 7:
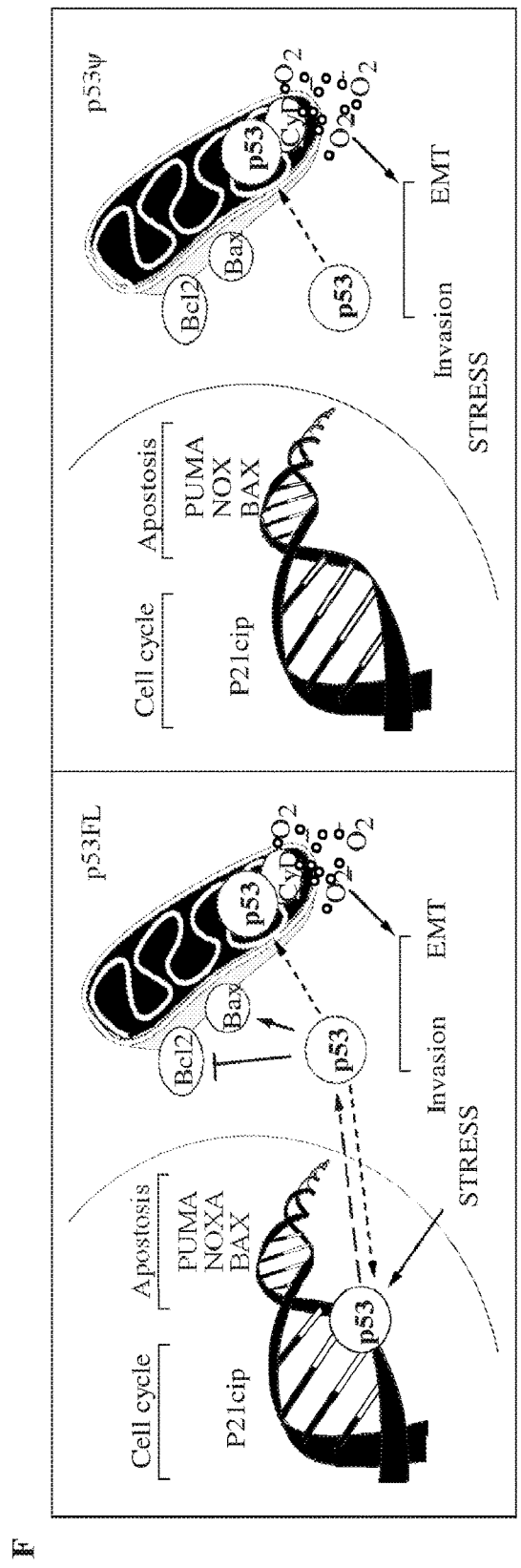

Cyclophilin D and Reactive Oxygen Species are Required for EMT Induction by p53Ψ and p53 Gain-of-Function Mutants To determine whether CypD and ROS have a causative role in EMT mediated by p53Ψ, CypD and ROS levels were modulated in cells ectopically expressing p53Ψ (A549, MCF7, H1299) and their effects on expression of EMT markers and cell invasion were assessed. Silencing CypD with either of two siRNAs (FIG. 7A) or pharmacologically inhibiting CypD by treating cells with CsA (FIG. 7B and FIG. 13A) was sufficient to prevent EMT and to diminish cell motility in cells expressing p53Ψ (FIG. 7C). As in the case of CypD, inhibition of ROS production with N-acetyl cysteine (NAC) or Tempol, two well-known ROS scavengers, augmented expression of E-cadherin (FIG. 7E and FIG. 13C) and decreased invasive capabilities of p53Ψ-expressing cells compared to control cells (FIG. 13D). In contrast, low doses of $H_2O_2$ decreased the expression of E-cadherin without compromising cell viability (FIG. 7D).

To exclude the possibility that ROS-induced EMT was independent of CypD in p53Ψ-expressing cells, epistasis experiments were performed. Specifically, E-cadherin expression was measured upon manipulation of ROS levels (e.g. by NAC treatment) in cells ectopically expressing p53Ψ in the presence and absence of CypD (FIG. 13B). If CypD and p53Ψ act on parallel pathways, an additive effect of CypD silencing and ROS inhibition would be predicted. In contrast, if p53Ψ acts solely through CypD, then CypD silencing would be sufficient to reduce ROS levels and no additive effect would be observed. Silencing of CypD blocked p53Ψ-induced EMT, and treatment of cells with NAC did not increase E-cadherin expression in cells in which CypD was silenced (FIG. 13B). Together these data strongly support a model in which the p53Ψ interaction with CypD increases mPTP permeability and increases ROS production. This in turn is necessary and sufficient for p53Ψ-induced EMT (FIG. 7F, right panel).

DISCUSSION

In summary, described is a novel, evolutionarily conserved mode of p53 regulation involving alternative splicing of the TP53 mRNA. The use of an alternative 3' splice site in intron 6 generates a previously uncharacterized p53 isoform, p53Ψ. The protein product of this alternatively spliced mRNA is incapable of sequence-specific DNA binding and transactivation of canonical p53 target genes, but does induce the acquisition of mesenchymal-like characteristics. Because p53Ψ is still capable of binding to CypD and regulating the mitochondria pore permeability, it appears that p53Ψ encodes a "separation-of-function" isoform. Importantly, the data also indicate that the cytoplasmic p53 activity is sufficient to reprogram cells towards acquisition of features associated with pro-metastatic phenotypes.

At the molecular level, this evidence shows that p53Ψ-induced EMT does not depend on p53 transcriptional activity, but instead relies on its mitochondrial matrix localization and its physical interaction with mPTP regulator CypD. In particular, reactive oxygen species play a pivotal role as second messengers in mediating p53Ψ-induced EMT.

Although p53Ψ ectopic expression failed to modify the expression of any of these genes, that p53Ψ is generated at the expense of p53FL indicates that in cells in which p53Ψ is generated as a result of an alternative splicing events, ROS production can be attributed to both a CypD-dependent mechanism and to changes in the expression of these p53FL target genes. Indeed, in cells that inherently express p53Ψ ($CD44^{high}/CD24^{low}$ cells sorted from injured lung), decreased expression of these p53 targets was observed.

MATERIALS AND METHODS

Cell Culture.

A549, H3H1299 (NCI-H1299), MCF7, PC9, H460 (NCI-H460), H4006 (NCI-H4006), and Phoenix-AMPHO cells were obtained from the American Type Culture Collection (ATCC) repository. The Hop62 cells were obtained from the NCI repository. All the cell lines except for Phoenix-AMPHO, HEK293T, and MCF7 were cultured in RPMI supplemented with 5% FBS, glutamine, penicillin, and streptomycin. Phoenix-AMPHO, HEK293, and MCF7 were cultured in DMEM containing 10% FBS, penicillin, streptomycin, and sodium pyruvate.

Antibodies and Reagents.

The following antibodies were used in this study: mouse anti-E-cadherin antibody (BD Transduction Laboratories), anti-p53 antibody (DO-1,Calbiochem), mouse anti-β-tubulin antibody (2-28-33, Santa Cruz Biotechnology), rabbit anti-PARP antibody (46D11, Cell Signaling Technology), rabbit anti-BAX antibody (D2E11, Cell Signaling Technology), rabbit anti-PUMA antibody (#4976, Cell Signaling Technology), rabbit anti-p21waf1/cip1 antibody (12D1, Cell Signaling Technology), anti-CpD (ab110324, Abcam), anti-CD31 (clone 390, EBioscience), anti-CD45 (Clone 30-F11 EBioscience), anti-CD24 (Clone MI-69 EBioscience), anti-CD44 (Clone IM-7 Biolegend), Tid-1 (MS-1564-PO). The chemical reagents used for cell treatment were cyclosporin A from Sigma-Aldrich (30024), calcein AM and MitoSox from Molecular Probes/Life Technologies, and $H_2O_2$ and doxorubicin hydrochloride from Sigma-Aldrich (#D1515), NAC from Sigma-Aldrich (A9165) and Tempol from Tocris (cat no 3082). P53 SiRNA (GGGTTAGTTTACAATCAGC (SEQ ID NO:5); GGTGAACCTTAGTACCTAA (SEQ ID NO:6)) and Tid1 siRNA (CTACATCCACATCAAGATA (SEQ ID NO:7); GAAAGCCTATTATCAGCTT (SEQ ID NO:8); AGCGAGTGATGATCCCTGT (SEQ ID NO:9)) and CypD siRNA (AGGCAGATGTCGTCCCAAA (SEQ ID NO:10); CGACTTCACCAACCACAAT (SEQ ID NO:11)) were purchased from Invitrogen.

REFERENCES

1. Junttila M R, Evan G I (2009) p53-a Jack of all trades but master of none. Nature Reviews Cancer 9: 821-829.
2. Hu W, Feng Z, Teresky A K, Levine A J (2007) p53 regulates maternal reproduction through LIF. Nature 450: 721-724.
3. Aldaz C M, Hu Y, Daniel R, Gaddis S, Kittrell F, et al. (2002) Serial analysis of gene expression in normal p53 null mammary epithelium. Oncogene 21: 6366-6376.
4. Matoba S, Kang J G, Patino W D, Wragg A, Boehm M, et al. (2006) p53 regulates mitochondrial respiration. Science 312: 1650-1653.
5. Meletis K, Wirta V, Hede S M, Nister M, Lundeberg J, et al. (2006) p53 suppresses the self-renewal of adult neural stem cells. Development 133: 363-369.
6. Godar S, Ince T A, Bell G W, Feldser D, Donaher J L, et al. (2008) Growth-inhibitory and tumor-suppressive functions of p53 depend on its repression of CD44 expression. Cell 134: 62-73.
7. Aruffo A, Stamenkovic I, Melnick M, Underhill C B, Seed B (1990) CD44 is the principal cell surface receptor for hyaluronate. Cell 61: 1303-1313.
8. Jin L, Hope K J, Zhai Q, Smadja-Joffe F, Dick J E (2006) Targeting of CD44 eradicates human acute myeloid leukemic stem cells. Nature medicine 12: 1167-1174.
9. Weber G F, Bronson R T, Hagan J, Cantor H, Schmits R, et al. (2002) Absence of the CD44 gene prevents sarcoma metastasis. Cancer research 62: 2281-2286.
10. Ponta H, Sherman L, Herrlich P A (2003) CD44: from adhesion molecules to signalling regulators. Nature reviews Molecular cell biology 4: 33-45.
11. Buckpitt A, Boland B, Isbell M, Morin D, Shultz M, et al. (2002) Naphthalene-induced respiratory tract toxicity: metabolic mechanisms of toxicity. Drug metabolism reviews 34: 791-820.
12. Kloek A P, McCarter J P, Setterquist R A, Schedl T, Goldberg D E (1996) *Caenorhabditis* globin genes: rapid intronic divergence contrasts with conservation of silent exonic sites. Journal of molecular evolution 43: 101-108.
13. Plaa G L, Larson R E (1964) Ccl-4-Induced Liver Damage. Current Concepts Regarding Mechanisms of Action. Archives of environmental health 9: 536-543.
14. Rivlin N, Brosh R, Oren M, Rotter V (2011) Mutations in the p53 Tumor Suppressor Gene: Important Milestones at the Various Steps of Tumorigenesis. Genes & cancer 2: 466-474.
15. Gupta P B, Fillmore C M, Jiang G, Shapira S D, Tao K, et al. (2011) Stochastic state transitions give rise to phenotypic equilibrium in populations of cancer cells. Cell 146: 633-644.
16. Black D L (2003) Mechanisms of alternative pre-messenger RNA splicing. Annual review of biochemistry 72: 291-336.
17. Chen C H, Dickman K G, Moriya M, Zavadil J, Sidorenko V S, et al. (2012) Aristolochic acid-associated urothelial cancer in Taiwan. Proceedings of the National Academy of Sciences of the United States of America 109: 8241-8246.
18. Grollman A P, Shibutani S, Moriya M, Miller F, Wu L, et al. (2007) Aristolochic acid and the etiology of endemic (Balkan) nephropathy. Proceedings of the National Academy of Sciences of the United States of America 104: 12129-12134.
19. Bourdon J C, Fernandes K, Murray-Zmijewski F, Liu G, Diot A, et al. (2005) p53 isoforms can regulate p53 transcriptional activity. Genes & development 19: 2122-2137.
20. Batinac T, Gruber F, Lipozencic J, Zamolo-Koncar G, Stasic A, et al. (2003) Protein p53—structure, function, and possible therapeutic implications. Acta dermatovenerologica *Croatica*: ADC 11: 225-230.
21. Muller P A, Vousden K H (2013) p53 mutations in cancer. Nature cell biology 15: 2-8.
22. Hanel W, Marchenko N, Xu S, Xiaofeng Yu S, Weng W, et al. (2013) Two hot spot mutant p53 mouse models display differential gain of function in tumorigenesis. Cell death and differentiation 20: 898-909.

23. Wu Y, Zhou B P (2008) New insights of epithelial-mesenchymal transition in cancer metastasis. Acta biochimica et biophysica *Sinica* 40: 643-650.
24. Nguyen D X, Bos P D, Massague J (2009) Metastasis: from dissemination to organ-specific colonization. Nature reviews Cancer 9: 274-284.
25. Mihara M, Erster S, Zaika A, Petrenko O, Chittenden T, et al. (2003) p53 has a direct apoptogenic role at the mitochondria. Molecular cell 11: 577-590.
26. Vaseva A V, Moll U M (2009) The mitochondrial p53 pathway. Biochimica et biophysica acta 1787: 414-420.
27. Vaseva A V, Marchenko N D, Ji K, Tsirka S E, Holzmann S, et al. (2012) p53 opens the mitochondrial permeability transition pore to trigger necrosis. Cell 149: 1536-1548.
28. Marchenko N D, Wolff S, Erster S, Becker K, Moll U M (2007) Monoubiquitylation promotes mitochondrial p53 translocation. The EMBO journal 26: 923-934.
29. Neupert W, Herrmann J M (2007) Translocation of proteins into mitochondria. Annual Review of Biochemistry 76: 723-749.
30. Yogev O, Pines O (2011) Dual targeting of mitochondrial proteins: mechanism, regulation and function. Biochimica et biophysica acta 1808: 1012-1020.
31. Trinh D L, Elwi A N, Kim S W (2010) Direct interaction between p53 and Tid1 proteins affects p53 mitochondrial localization and apoptosis. Oncotarget 1: 396-404.
32. Ahn B Y, Trinh D L, Zajchowski L D, Lee B, Elwi A N, et al. (2010) Tid1 is a new regulator of p53 mitochondrial translocation and apoptosis in cancer. Oncogene 29: 1155-1166.
33. Lu B, Garrido N, Spelbrink J N, Suzuki C K (2006) Tid1 isoforms are mitochondrial DnaJ-like chaperones with unique carboxyl termini that determine cytosolic fate. Journal of Biological Chemistry 281: 13150-13158.
34. Kroemer G, Galluzzi L, Brenner C (2007) Mitochondrial membrane permeabilization in cell death. Physiol Rev 87: 99-163.
35. Gillessen T, Grasshoff C, Szinicz L (2002) Mitochondrial permeability transition can be directly monitored in living neurons. Biomedicine & Pharmacotherapy 56: 186-193.
36. Petronilli V, Miotto G, Canton M, Colonna R, Bernardi P, et al. (1998) Imaging the mitochondrial permeability transition pore in intact cells. Biofactors 8: 263-272.
37. Batandier C, Leverve X, Fontaine E (2004) Opening of the mitochondrial permeability transition pore induces reactive oxygen species production at the level of the respiratory chain complex I. Biochimica Et Biophysica Acta-Bioenergetics 1658: 217-217.
38. Robinson K M, Janes M S, Pehar M, Monette J S, Ross M F, et al. (2006) Selective fluorescent imaging of superoxide in vivo using ethidium-based probes. Proceedings of the National Academy of Sciences of the United States of America 103: 15038-15043.
39. Le Belle J E, Orozco N M, Paucar A A, Saxe J P, Mottahedeh J, et al. (2011) Proliferative Neural Stem Cells Have High Endogenous ROS Levels that Regulate Self-Renewal and Neurogenesis in a PI3K/Akt-Dependant Manner. Cell Stem Cell 8: 59-71.
40. Sena L A, Chandel N S (2012) Physiological roles of mitochondrial reactive oxygen species. Molecular cell 48: 158-167.
41. Hurd T R, DeGennaro M, Lehmann R (2012) Redox regulation of cell migration and adhesion. Trends in cell biology 22: 107-115.
42. Gomes L R, Terra L F, Sogayar M C, Labriola L (2011) Epithelial-Mesenchymal Transition: Implications in Cancer Progression and Metastasis. Current Pharmaceutical Biotechnology 12: 1881-1890.
43. Egeblad M, Nakasone E S, Werb Z (2010) Tumors as Organs: Complex Tissues that Interface with the Entire Organism. Developmental Cell 18: 884-901.
44. Yao Z, Fenoglio S, Gao D C, Camiolo M, Stiles B, et al. (2010) TGF-beta IL-6 axis mediates selective and adaptive mechanisms of resistance to molecular targeted therapy in lung cancer. Proceedings of the National Academy of Sciences of the United States of America 107: 15535-15540.

Having thus described several aspects of at least one embodiment of this disclosure, it is to be appreciated various alterations, modifications, and improvements will readily occur to those skilled in the art. Such alterations, modifications, and improvements are intended to be part of this disclosure and are intended to be within the spirit and scope of the disclosure. Accordingly, the foregoing description and drawings are by way of example only. All references described herein are incorporated by reference for the purposes described herein. The use of "including," "comprising," "or "having," "containing," "involving," and variations thereof herein, is meant to encompass the items listed thereafter and equivalents thereof as well as additional items.

What is claimed is:

1. A method of inhibiting cancer cells, comprising:
    (a) determining whether cancer cells express p53Ψ, wherein the cancer cells are in a population of cells; and
    (b) if the cancer cells in (a) express p53Ψ, administering a cyclophilin D (CypD) inhibitor in an effective amount that results in inhibition of p53Ψ protein activity.

2. The method of claim 1, wherein the population of cells is in an individual.

3. The method of claim 1, wherein the cancer cells are in a mammal.

4. The method of claim 3, wherein the mammal is a human.

5. The method of claim 1, wherein the CypD inhibitor is a pharmacologic inhibitor, a RNA interference (RNAi) molecule, an antisense oligonucleotide (ASO) or a CRISPR/Cas9 system that mediates gene editing.

6. The method of claim 5, wherein the pharmacologic inhibitor is cyclosporine.

7. The method of claim 1, further comprising administering a ROS inhibitor.

8. The method of claim 7, wherein the ROS inhibitor is a ROS scavenger or an inhibitor that reduces production of ROS and activity of one or more ROS-mediated signaling component required for p53Ψ activity.

9. The method of claim 8, wherein the ROS scavenger is N-acetyl cysteine or Tempol.

10. The method of claim 1, further comprising evaluating one or more characteristics of the cancer cells prior to, during, or after administering the inhibitor, wherein the one or more characteristics of the cancer cells is selected from: morphology, invasive ability, motility, and expression of a cell biomarker.

11. The method of claim 10, wherein increased expression of at least one cell biomarker selected from E-cadherin, CD24, CD104, MUC-1, MUC-4, MUC16, A33, CD143, CD166, PD-L1, B7-H2, B7-H3, Nectin-1, Nectin-2, Nectin-3, Nectin-4, cytokeratin, ZO-1, Laminin-1, Entactin, collagen, and miR200 family microRNAs indicates that a cell is epithelial cell-like.

12. The method of claim 10, wherein decreased expression of a cell biomarker selected from CD44, CD45, N-cadherin, Vimentin, Zeb1, Twist, Slug, or Fibronectin indicates that a cell is epithelial cell-like.

13. The method of claim 1, wherein the cancer cells in (a), also express one or more cell biomarkers of the mesenchymal state.

14. A method of inhibiting growth of cancer cells in an individual, comprising:
    (a) assessing cells in a population of cells obtained from an individual for expression of p53Ψ;
    (b) identifying the cells from (a) that express p53Ψ; and
    (c) if the cells assessed in (a) express p53Ψ, administering to the individual from whom the population of cells was obtained, a cyclophilin D (CypD) inhibitor in an effective amount that inhibits growth of cancer cells in the individual.

15. The method of claim 14, further comprising (d) assessing the cells in a population of cells for expression of the one or more cell markers of the mesenchymal state, expression of one or more markers of the epithelial state, or both expression of the one or more cell markers of the mesenchymal state and expression of one or more markers of the epithelial state, wherein if there is a decrease in expression of the one or more markers of the mesenchymal state, an increase in expression of one or more markers of the epithelial state, or both a decrease in expression of the one or more cell markers of the mesenchymal state and an increase in expression of one or more markers of the epithelial state, cancer cell growth is inhibited.

16. The method of claim 15, wherein markers of epithelial cell state and markers of mesenchymal cell state are selected from E-cadherin, CD24, CD104, CD44, CD45, N-cadherin, MUC-1, MUC-4, MUC16, A33, CD143, CD166, PD-L1, B7-H2, B7-H3, Nectin-1, Nectin-2, Nectin-3, Nectin-4, Vimentin, Zeb1, Twist, Slug, Fibronectin, cytokeratin, ZO-1, Laminin-1, Entactin, collagen, and a miR200 family microRNA.

17. The method of claim 14, wherein the CypD inhibitor is a pharmacologic inhibitor, a RNA interference (RNAi) molecule, an antisense oligonucleotide (ASO) or a CRISPR/Cas9 system that mediates gene editing.

18. The method of claim 17, wherein the pharmacologic inhibitor is cyclosporine.

19. The method of claim 14, wherein increased expression of at least one of E-cadherin, CD24, CD104, MUC-1, MUC-4, MUC16, A33, CD143, CD166, PD-L1, B7-H2, B7-H3, Nectin-1, Nectin-2, Nectin-3, Nectin-4, cytokeratin, ZO-1, Laminin-1, Entactin, collagen, and miR200 family microRNAs indicates that a cell is epithelial cell-like.

20. The method of claim 14, wherein decreased expression of CD44, CD45, N-cadherin, Vimentin, Zeb1, Twist, Slug, or Fibronectin indicates that a cell is epithelial cell-like.

21. The method of claim 14, wherein the cells assessed in (a) that express p53Ψ also express one or more cell markers of the mesenchymal state.

22. A method of treating an individual who has cancer cells that express p53Ψ, comprising administering to the individual in need thereof a CypD inhibitor in an effective amount that results in inhibition of p53Ψ.

23. A method of identifying an individual suffering from cancer as a candidate for treatment with a CypD inhibitor, comprising
    (a) determining whether cancer cells from the individual are CD44+ and CD24−;
    (b) determining whether the cancer cells from the individual express p53Ψ;
    (c) identifying the individual as a candidate for treatment if the cancer cells in (a) and (b) are CD44+ and CD24− and express p53Ψ; and
    (d) administering to the individual who has been identified as a candidate for treatment, a CypD inhibitor in an effective amount that results in inhibition of p534Ψ activity.

24. The method of claim 23, further comprising administration of a reactive oxygen species (ROS) inhibitor, wherein administration of the ROS inhibitor results in inhibition of signaling mediated by ROS required for the manifestation of p53Ψ mediated phenotypes.

25. The method of claim 24, further comprising administering an inhibitor of p53Ψ in an effective amount by route that results in entry of a sufficient amount of the p53Ψ inhibitor into the cell and inhibition of p53Ψ.

* * * * *

UNITED STATES PATENT AND TRADEMARK OFFICE
CERTIFICATE OF CORRECTION

PATENT NO. : 10,501,741 B2
APPLICATION NO. : 15/321561
DATED : December 10, 2019
INVENTOR(S) : Raffaella Sordella et al.

It is certified that error appears in the above-identified patent and that said Letters Patent is hereby corrected as shown below:

On the Title Page

Item (72) should be corrected to read:
Inventors: Raffaella Sordella, Cold Spring Harbor, NY (US); Serif Senturk, Balçova, Izmir (TR); Luca Cartegni, New York, NY (US); Zhan Yao, New York, NY (US)

Signed and Sealed this
Fifth Day of May, 2020

Andrei Iancu
*Director of the United States Patent and Trademark Office*

SEQUENCE LISTING

```
<160> NUMBER OF SEQ ID NOS: 26

<210> SEQ ID NO 1
<211> LENGTH: 1182
<212> TYPE: DNA
<213> ORGANISM: Homo sapiens

<400> SEQUENCE: 1
atggaggagc cgcagtcaga tcctagcgtc gagcccctc tgagtcagga aacattttca      60
gacctatgga aactacttcc tgaaaacaac gttctgtccc ccttgccgtc ccaagcaatg     120
gatgatttga tgctgtcccc ggacgatatt gaacaatggt tcactgaaga cccaggtcca     180
gatgaagctc ccagaatgcc agaggctgct cccccgtgg ccctgcacc agcagctcct      240 acaccggcgg cccctgcacc agcccctcc tggcccctgt catcttctgt cccttccag      300 aaaacctacc agggcagcta cggtttccgt ctgggcttct tgcattctgg gacagccaag     360
```

```
tctgtgactt gcacgtactc ccctgccctc aacaagatgt tttgccaact ggccaagacc      420
tgccctgtgc agctgtgggt tgattccaca cccccgcccg cacccgcgt ccgcgccatg       480
gccatctaca agcagtcaca gcacatgacg gaggttgtga ggcgctgccc ccaccatgag      540
cgctgctcag atagcgatgg tctggcccct cctcagcatc ttatccgagt ggaaggaaat      600
ttgcgtgtgg agtatttgga tgacagaaac acttttcgac atagtgtggt ggtgccctat      660
gagccgcctg aggttggctc tgactgtacc accatccact acaactacat gtgtaacagt      720
tcctgcatgg gcggcatgaa ccggaggccc atcctcacca tcatcacact ggaagactcc      780
agtggtaatc tactgggacg gaacagcttt gaggtgcgtg tttgtgcctg tcctgggaga      840
gaccggcgca cagaggaaga gaatctccgc aagaaagggg agcctcacca cgagctgccc      900
ccagggagca ctaagcgagc actgcccaac aacaccagct cctctcccca gccaaagaag      960
aaaccactgg atggagaata tttcaccctt cagatccgtg ggcgtgagcg cttcgagatg     1020
ttccgagagc tgaatgaggc cttggaactc aaggatgccc aggctgggaa ggagccaggg     1080
gggagcaggg ctcactccag ccacctgaag tccaaaaagg gtcagtctac ctcccgccat     1140
aaaaaaactca tgttcaagac agaagggcct gactcagact ga                       1182
```

<210> SEQ ID NO 2
<211> LENGTH: 393
<212> TYPE: PRT
<213> ORGANISM: Homo sapiens

<400> SEQUENCE: 2

```
Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Gly Thr Arg Val Arg Ala Met
145                 150                 155                 160

Ala Ile Tyr Lys Gln Ser Gln His Met Thr Glu Val Val Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220
```

```
Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
            245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
            325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
            355                 360                 365

Leu Lys Ser Lys Lys Gly Gln Ser Thr Ser Arg His Lys Lys Leu Met
370                 375                 380

Phe Lys Thr Glu Gly Pro Asp Ser Asp
385                 390
```

<210> SEQ ID NO 3
<211> LENGTH: 732
<212> TYPE: DNA
<213> ORGANISM: Artificial Sequence
<220> FEATURE:
<223> OTHER INFORMATION: Synthetic Polynucleotide

<400> SEQUENCE: 3

```
atggaggagc cgcagtcaga tcctagcgtc gagccccctc tgagtcagga acatttttca      60
gacctatgga aactacttcc tgaaaacaac gttctgtccc ccttgccgtc ccaagcaatg     120
gatgatttga tgctgtcccc ggacgatatt gaacaatggt tcactgaaga cccaggtcca     180
gatgaagctc ccagaatgcc agaggctgct ccccccgtgg cccctgcacc agcagctcct     240
acaccggcgg cccctgcacc agccccctcc tggcccctgt catcttctgt cccttcccag     300
aaaacctacc agggcagcta cggtttccgt ctgggcttct gcattctggg acagccaag     360 tctgtgactt gcacgtactc ccctgccctc aacaagatgt tttgccaact ggccaagacc     420
tgccctgtgc agctgtgggt tgattccaca cccccgcccg caccccgcgt ccgcgccatg     480
gccatctaca agcagtcaca gcacatgacg gaggttgtga ggcgctgccc ccaccatgag     540
cgctgctcag atagcgatgg tctggccccct cctcagcatc ttatccgagt ggaaggaaat     600
ttgcgtgtgg agtatttgga tgacagaaac acttttcgac atagtgtggt ggtgccctat     660
gagccgcctg aggtctcccc aaggcgcact ggcctcatct gggcctgtgt tatctcctg     720 ggttggctct ga                                                         732
```

<210> SEQ ID NO 4
<211> LENGTH: 243
<212> TYPE: PRT
<213> ORGANISM: Artificial Sequence
<220> FEATURE:
<223> OTHER INFORMATION: Synthetic Polypeptide

```
<400> SEQUENCE: 4

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65              70                  75                  80

Thr Pro Ala Ala Pro Ala Pro Ala Pro Ser Trp Pro Leu Ser Ser Ser
            85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
            115                 120                 125

Ala Leu Asn Lys Met Phe Cys Gln Leu Ala Lys Thr Cys Pro Val Gln
        130                 135                 140

Leu Trp Val Asp Ser Thr Pro Pro Gly Thr Arg Val Arg Ala Met
145                 150                 155                 160

Ala Ile Tyr Lys Gln Ser Gln His Met Thr Glu Val Val Arg Arg Cys
            165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
            195                 200                 205

Arg Asn Thr Phe Arg His Ser Val Val Val Pro Tyr Glu Pro Pro Glu
        210                 215                 220

Val Ser Pro Arg Arg Thr Gly Leu Ile Leu Gly Leu Cys Tyr Leu Leu
225                 230                 235                 240

Gly Trp Leu

<210> SEQ ID NO 5
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 5
gggttagttt acaatcagc                                              19

<210> SEQ ID NO 6
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 6
ggtgaacctt agtacctaa                                              19

<210> SEQ ID NO 7
<211> LENGTH: 19
<212> TYPE: DNA
<213> ORGANISM: Artificial Sequence
```

```
<220> FEATURE:
<223> OTHER INFORMATION: Synthetic Polynucleotide

<400> SEQUENCE: 7
ctacatccac atcaagata                                                19

<210> SEQ ID NO 8
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 8
gaaagcctat tatcagctt                                                19

<210> SEQ ID NO 9
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 9
agcgagtgat gatccctgt                                                19

<210> SEQ ID NO 10
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 10
aggcagatgt cgtcccaaa                                                19

<210> SEQ ID NO 11
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 11
cgacttcacc aaccacaat                                                19

<210> SEQ ID NO 12
<211> LENGTH: 13
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (6)..(7)
<223> OTHER INFORMATION: Splice junction

<400> SEQUENCE: 12
cccgaggccg gct                                                      13

<210> SEQ ID NO 13
<211> LENGTH: 13
<212> TYPE: DNA
<213> ORGANISM: Artificial Sequence
<220> FEATURE:
<223> OTHER INFORMATION: Synthetic Polynucleotide
```

<400> SEQUENCE: 13
cccgaggtca cct                                                            13

<210> SEQ ID NO 14
<211> LENGTH: 43
<212> TYPE: DNA
<213> ORGANISM: Artificial Sequence
<220> FEATURE:
<223> OTHER INFORMATION: Synthetic Polynucleotide

<400> SEQUENCE: 14
ttatctccta ggttggctct gactgtacca ccatccacta caa                           43

<210> SEQ ID NO 15
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 15

Ser Pro Arg Arg Thr Gly Leu Ile Leu Gly Leu Cys Tyr Leu Leu Gly
1               5                   10                  15

Trp Leu

<210> SEQ ID NO 16
<211> LENGTH: 190
<212> TYPE: DNA
<213> ORGANISM: Homo sapiens

<400> SEQUENCE: 16
ggcctcccct gcttgccaca ggtctcccca aggcgcactg gcctcatctt gggcctgtgt         60
tatctcctag gttggctctg actgtaccac catccactac aactacatgt gtaacagttc        120
ctgcatgggc ggcatgaacc ggaggcccat cctcaccatc atcacactgg aagactccag        180
gtcaggagcc                                                              190

<210> SEQ ID NO 17
<211> LENGTH: 190
<212> TYPE: DNA
<213> ORGANISM: Mus musculus

<400> SEQUENCE: 17
tcccggctgc tgcaggtcac ctgtagtgag gtagggagcg acttcacctg gatcctgtgt         60
cttcccccag gccggctctg agtataccac catccactac aagtacatgt gtaatagctc        120
ctgcatgggg ggcatgaacc gccgacctat ccttaccatc atcacactgg aagactccag        180
gtaggaaggc                                                              190

<210> SEQ ID NO 18
<211> LENGTH: 35
<212> TYPE: DNA
<213> ORGANISM: Homo sapiens

<400> SEQUENCE: 18
aggcctcccc tgcttgccac aggtctcccc aaggc                                   35

<210> SEQ ID NO 19
<211> LENGTH: 35
<212> TYPE: DNA
<213> ORGANISM: Pan troglodytes

<400> SEQUENCE: 19
aggcctcccc tgcttgccac aggtctcccc aaggc         35

<210> SEQ ID NO 20
<211> LENGTH: 34
<212> TYPE: DNA
<213> ORGANISM: Mus musculus

<400> SEQUENCE: 20
agccattccc ggctgctgca ggtcacctgt agtg          34

<210> SEQ ID NO 21
<211> LENGTH: 41
<212> TYPE: DNA
<213> ORGANISM: Canis familiaris

<400> SEQUENCE: 21
agccctgtga ggagtgcaga ggcaggtggg tcatcccatt c  41

<210> SEQ ID NO 22
<211> LENGTH: 37
<212> TYPE: DNA
<213> ORGANISM: Bos taurus

<400> SEQUENCE: 22
tgacctccca cagcctgtca ggtgcgcaga gcagtgg       37

<210> SEQ ID NO 23
<211> LENGTH: 36
<212> TYPE: DNA
<213> ORGANISM: Danio rerio

<400> SEQUENCE: 23
tcggtttcac tatgtgaaca gctctatttt tgatga        36

<210> SEQ ID NO 24
<211> LENGTH: 12
<212> TYPE: DNA
<213> ORGANISM: Homo sapiens

<400> SEQUENCE: 24
gcctgaggtt gg                                  12

<210> SEQ ID NO 25
<211> LENGTH: 11
<212> TYPE: DNA
<213> ORGANISM: Artificial Sequence
<220> FEATURE:
<223> OTHER INFORMATION: Synthetic Polynucleotide

<400> SEQUENCE: 25
cctgaggtct c                                   11

<210> SEQ ID NO 26
<211> LENGTH: 25
<212> TYPE: DNA
<213> ORGANISM: Homo sapiens

<400> SEQUENCE: 26
gtgttatctc ctgggttggc tctga                    25